(12) United States Patent
Hager et al.

(10) Patent No.: US 11,655,258 B2
(45) Date of Patent: May 23, 2023

(54) HETEROCYCLE DERIVATIVES AS PESTICIDES

(71) Applicant: BAYER AKTIENGESELLSCHAFT, Leverkusen (DE)

(72) Inventors: Dominik Hager, Monheim (DE); Ruediger Fischer, Pulheim (DE); Laura Hoffmeister, Duesseldorf (DE); Nina Kausch-Busies, Duesseldorf (DE); Marc Mosrin, Cologne (DE); David Wilcke, Duesseldorf (DE); Matthieu Willot, Duesseldorf (DE); Kerstin Ilg, Cologne (DE); Ulrich Goergens, Ratingen (DE); Andreas Turberg, Haan (DE)

(73) Assignee: Bayer Aktiengesellschaft, Leverkusen (DE)

( * ) Notice: Subject to any disclaimer, the term of this patent is extended or adjusted under 35 U.S.C. 154(b) by 458 days.

(21) Appl. No.: 16/640,656

(22) PCT Filed: Aug. 17, 2018

(86) PCT No.: PCT/EP2018/072308
§ 371 (c)(1),
(2) Date: Feb. 20, 2020

(87) PCT Pub. No.: WO2019/038195
PCT Pub. Date: Feb. 28, 2019

(65) Prior Publication Data
US 2020/0181172 A1 Jun. 11, 2020

(30) Foreign Application Priority Data

Aug. 22, 2017 (EP) .................................... 17187272

(51) Int. Cl.
| *A01N 43/90* | (2006.01) |
|---|---|
| *C07D 519/00* | (2006.01) |
| *C07D 471/04* | (2006.01) |
| *C07D 487/04* | (2006.01) |

(52) U.S. Cl.
CPC .......... *C07D 519/00* (2013.01); *A01N 43/90* (2013.01); *C07D 471/04* (2013.01); *C07D 487/04* (2013.01)

(58) Field of Classification Search
None
See application file for complete search history.

(56) References Cited

U.S. PATENT DOCUMENTS

| 2005/0250829 A1* | 11/2005 | Bressi ..................... A61P 21/00 514/393 |
|---|---|---|
| 2014/0303141 A1 | 10/2014 | Flohr et al. |
| 2015/0181880 A1 | 7/2015 | Takahashi et al. |
| 2018/0079748 A1 | 3/2018 | Jung et al. |
| 2018/0116222 A1 | 5/2018 | Fischer et al. |
| 2020/0223868 A1 | 7/2020 | Kudo et al. |

FOREIGN PATENT DOCUMENTS

| CN | 108884091 A | 11/2018 |
|---|---|---|
| JP | 2016528189 A | 9/2016 |
| JP | 201824657 A | 2/2018 |
| WO | 2010125985 A1 | 11/2010 |
| WO | 2013041472 A1 | 3/2013 |
| WO | 2013191113 A1 | 12/2013 |
| WO | 2015000715 A1 | 1/2015 |
| WO | 2017026384 A1 | 2/2016 |
| WO | 2016091731 A1 | 6/2016 |
| WO | 2016107742 A1 | 7/2016 |
| WO | 2016142326 A1 | 9/2016 |
| WO | 2016142327 A1 | 9/2016 |
| WO | 2016162318 A1 | 10/2016 |
| WO | 2016169882 A1 | 10/2016 |
| WO | 2017061497 A1 | 4/2017 |
| WO | 2016129684 A1 | 11/2017 |

OTHER PUBLICATIONS

International Search Report for PCT/EP2018/072308, dated Oct. 11, 2018.

\* cited by examiner

*Primary Examiner* — Alton N Pryor
(74) *Attorney, Agent, or Firm* — McBee Moore & Vanik IP, LLC

(57) ABSTRACT

The present invention relates to novel fused bicyclic heterocycle derivatives of formula (I)

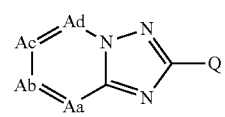

(I)

in which Aa, Ab, Ac, Ad and Q have the meanings mentioned above,
agrochemical formulations containing the compounds of formula (I) and their use as acaricides and/or insecticides for controlling animal pests, particularly arthropods and especially insects and arachnids.

15 Claims, No Drawings

HETEROCYCLE DERIVATIVES AS PESTICIDES

CROSS-REFERENCE TO RELATED APPLICATIONS

This application is the National Stage entry of International Application No. PCT/EP2018/072308, filed 17 Aug. 2018, which claims priority to European Patent Application No. 17187272.4, filed 22 Aug. 2017.

BACKGROUND

Field

The present invention relates to heterocycle derivatives of formula (I), to agrochemical formulations containing the compounds of formula (I) and their use as acaricides and/or insecticides for controlling animal pests, particularly arthropods and especially insects and arachnids.

Description of Related Art

Heterocycle derivatives having insecticidal properties have already been described in the literature, for example in WO 2010/125985, WO 2013/191113, WO 2016/091731, WO 2016/107742, WO 2016/129684, WO 2016/142326, WO 2016/142327, WO 2016/169882, WO 2016/162318, WO2017/061497, WO 2017/001311 and JP 2018-24657.

Modern crop protection compositions have to meet many demands, for example in relation to extent, persistence and spectrum of their action and possible use. Questions of toxicity, sparing of beneficial species and pollinators, environmental properties, application rates, combinability with other active compounds or formulation auxiliaries play a role, as does the question of the complexity involved in the synthesis of an active compound, and resistances can also occur, to mention just a few parameters. For all these reasons alone, the search for novel crop protection compositions cannot be considered complete, and there is a constant need for novel compounds having improved properties compared to the known compounds, at least in relation to individual aspects.

SUMMARY

It was an object of the present invention to provide compounds which broaden the spectrum of the pesticides in various aspects and/or improve their activity.

Novel heterocycle derivatives have now been found, these having advantages over the compounds already known, examples of which include better biological or environmental properties, a wider range of application methods, better insecticidal or acaricidal action, and good compatibility with useful plants. The heterocycle derivatives can be used in combination with further compositions for improving efficacy, especially against insects that are difficult to control.

The subject matter of the present invention is therefore novel compounds of formula (I)

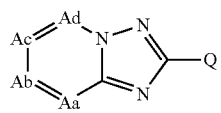

(I)

in which (Configuration 1)
Aa represents nitrogen or $C(R^1)$,
Ab represents nitrogen or $C(R^2)$,
Ac represents nitrogen or $C(R^3)$,
Ad represents nitrogen or $C(R^4)$,
where at most two of the groups Aa, Ab, Ac and Ad represent nitrogen,
$R^1$, $R^2$, $R^3$, $R^4$ independently of one another each represent hydrogen, halogen, cyano, hydroxycarbonyl, SCN, $SF_5$, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl, $(C_1-C_6)$-alkoxy, $(C_1-C_6)$-haloalkoxy, $(C_3-C_8)$-cycloalkyl, halo-$(C_3-C_8)$-cyclo alkyl, $(C_3-C_6)$-cycloalkyl-$(C_1-C_6)$-alkyl, $(C_3-C_6)$-cycloalkyl-$(C_1-C_6)$-halo alkyl, $(C_1-C_6)$-alkyl-$(C_3-C_8)$-cycloalkyl, $(C_1-C_6)$-haloalkyl-$(C_3-C_6)$-cycloalkyl, $(C_3-C_6)$-cycloalkyl-$(C_3-C_6)$-cycloalkyl, spiro-$(C_3-C_6)$-cycloalkyl-$(C_3-C_6)$-cycloalkyl, $(C_4-C_{12})$-bicycloalkyl, $(C_1-C_6)$-cyanoalkyl, cyano-$(C_3-C_6)$-cyclo alkyl, $(C_1-C_6)$-alkylthio, $(C_1-C_6)$-haloalkylthio, $(C_1-C_6)$-alkylsulfinyl, $(C_1-C_6)$-haloalkylsulfinyl, $(C_1-C_6)$-alkylsulfonyl, $(C_1-C_6)$-haloalkylsulfonyl, $(C_1-C_6)$-alkyl sulfonyloxy, amino sulfonyl, $(C_1-C_6)$-alkylaminosulfonyl or di-$(C_1-C_6)$-alkylaminosulfonyl,
where at most two of the radicals $R^1$, $R^2$, $R^3$ and $R^4$ represent a radical other than hydrogen,
Q represents a partially saturated or saturated heterocyclic or heteroaromatic 8-, 9- or 10-membered fused bicyclic ring system which may optionally contain at least one carbonyl group and where the ring system is substituted by a —$S(O)_nR^5$ group and optionally has one or more further substituents, where the substituents independently of one another may be selected from hydrogen, halogen, cyano, nitro, SCN, $SF_5$, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl, $(C_1-C_6)$-haloalkoxy, $(C_1-C_6)$-alkoxy, $(C_3-C_8)$-cycloalkyl, $(C_3-C_8)$-halocycloalkyl, $(C_3-C_6)$-cycloalkyl-$(C_1-C_6)$-alkyl, $(C_3-C_6)$-cyclo alkyl-$(C_1-C_6)$-halo alkyl, $(C_1-C_6)$-alkyl-$(C_3-C_8)$-cycloalkyl, $(C_1-C_6)$-halo alkyl-$(C_3-C_8)$-cyclo alkyl, $(C_3-C_6)$-cycloalkyl-$(C_3-C_6)$-cycloalkyl, spiro-$(C_3-C_6)$-cycloalkyl-$(C_3-C_6)$-cycloalkyl, $(C_4-C_{12})$-bicycloalkyl, $(C_1-C_6)$-cyanoalkyl, $(C_3-C_6)$-cyanocycloalkyl, $(C_1-C_6)$-hydroxy alkyl, $(C_1-C_6)$-alkoxycarbonyl-$(C_1-C_6)$-alkyl, $(C_1-C_6)$-alkoxy-$(C_1-C_6)$-alkyl, $(C_2-C_6)$-cyanoalkenyl, $(C_3-C_6)$-cycloalkyl-$(C_2-C_6)$-alkenyl, $(C_2-C_6)$-cyanoalkynyl, $(C_3-C_6)$-cycloalkyl-$(C_2-C_6)$-alkynyl, $(C_1-C_6)$-halo alkoxy-$(C_1-C_6)$-alkyl, $(C_1-C_6)$-alkylthio-$(C_1-C_6)$-alkyl, $(C_1-C_6)$-alkylsulfinyl-$(C_1-C_6)$-alkyl, $(C_1-C_6)$-alkylsulfonyl-$(C_1-C_6)$-alkyl or $(C_1-C_6)$-alkylcarbonyl-$(C_1-C_6)$-alkyl,
or where the substituents independently of one another may in each case be selected from a phenyl ring or a 3- to 6-membered aromatic, partially saturated or saturated heterocycle, where the heteroatoms are selected from the group consisting of N, S, O and where the phenyl ring or heterocycle may in each case optionally be mono- or polysubstituted by identical or different substituents and where the substituents independently of one another may be selected from halogen, cyano, nitro, hydroxy, SCN, $SF_5$, $(C_1-C_6)$-alkyl, $(C_2-C_6)$-alkenyl, $(C_2-C_6)$-haloalkenyl, $(C_2-C_6)$-alkynyl, $(C_2-C_6)$-haloalkynyl, $(C_3-C_8)$-cycloalkyl, $(C_3-C_8)$-halocycloalkyl, $(C_1-C_6)$-halo alkyl, $(C_1-C_6)$-alkoxy, $(C_1-C_6)$-halo alkoxy $(C_1-C_4)$-alkylthio, $(C_1-C_4)$-alkylsulfinyl, $(C_1-C_4)$-alkylsulfonyl, $(C_1-C_4)$-haloalkylthio, $(C_1-C_4)$-haloalkylsulfinyl, $(C_1-C_4)$-halo alkylsulfonyl, $(C_1-C_4)$-alkyl amino, di-$(C_1-C_4$-alkyl)amino, $(C_3-C_6)$-cycloalkylamino, $(C_1-C_6)$-alkylcarbonyl, $(C_1-C_6)$-alkoxycarbonyl, $(C_1-C_6)$-alkylaminocarbonyl or di-$(C_1-C_4)$-alkylaminocarbonyl,
or where the substituents represent groups independently of one another selected from —C(=O)—$R^{21}$, —C(=S)—$R^{21}$, —C(=O)—$OR^{21}$, —C(=O)—

NR²⁰R²¹, —C(=S)—NR²⁰R²¹, —CH(=N—OR²³), —CH(=N—NR²³R²⁴), —OR²¹, —OC(=O)—NR²⁰R²¹, —NR²⁰R²¹, —N(R²⁰)—NR²¹R²², —N(R²⁰)—C(=O)—R²¹, —N(R²⁰)—C(=S)—R²¹, —N(R²⁰)—C(=O)—OR²¹, —N(R²⁰)—C(=S)—OR²¹, —N(R²⁰)—C(=O)—NR²¹R²², —N(R²⁰)—C(=S)—NR²¹R²² or S(=O)$_m$R²¹, where R⁵ represents (C₁-C₄)-alkyl, (C₁-C₄)-hydroxy alkyl, (C₁-C₄)-halo alkyl, (C₂-C₄)-alkenyl, (C₂-C₄)-haloalkenyl, (C₂-C₄)-alkynyl, (C₂-C₄)-haloalkynyl, (C₃-C₆)-cycloalkyl, (C₃-C₆)-halocycloalkyl, (C₁-C₄)-alkylthio-(C₁-C₄)-alkyl, (C₁-C₄)-alkyl sulfinyl-(C₁-C₄)-alkyl or (C₁-C₄)-alkyl sulfonyl-(C₁-C₄)-alkyl, n represents 0, 1 or 2, R²⁰, R²¹, R²² independently of one another each represent hydrogen or represent (C₁-C₆)-alkyl, (C₁-C₆)-halo alkyl, (C₁-C₆)-alkoxy, (C₁-C₆)-halo alkoxy, (C₂-C₆)-alkenyl, (C₂-C₆)-alkynyl, (C₃-C₈)-halocycloalkyl or (C₃-C₈)-cycloalkyl, each of which is optionally mono- or polysubstituted by identical or different substituents, where the substituents independently of one another may be selected from halogen, cyano, hydroxy, hydroxycarbonyl, (C₁-C₆)-alkyl, (C₁-C₆)-haloalkyl, (C₃-C₈)-cyclo alkyl, (C₁-C₆)-alkoxy, (C₁-C₆)-haloalkoxy, amino, (C₁-C₆)-alkylamino, di-(C₁-C₆)-alkylamino, (C₁-C₆)-alkylcarbonyl, (C₁-C₆)-alkoxycarbonyl, (C₁-C₆)-alkylthio, (C₁-C₆)-alkylsulfinyl, (C₁-C₆)-alkylsulfonyl, (C₁-C₄)-halo alkylthio, (C₁-C₄)-halo alkylsulfinyl, (C₁-C₄)-haloalkylsulfonyl or (C₁-C₆)-alkylsulfonyloxy or R²⁰, R²¹, R²² independently of one another each represent a phenyl ring or a 3- to 6-membered aromatic, partially saturated or saturated heterocycle, where the heteroatoms are selected from the group consisting of N, S, O and where the phenyl ring or heterocycle may in each case optionally be mono- or polysubstituted by identical or different substituents and where the substituents independently of one another may be selected from halogen, cyano, nitro, hydroxy, hydroxycarbonyl, (C₁-C₆)-alkyl, (C₂-C₆)-alkenyl, (C₂-C₆)-alkynyl, (C₃-C₈)-cycloalkyl, (C₁-C₆)-haloalkyl, (C₂-C₆)-haloalkenyl, (C₂-C₆)-haloalkynyl, (C₁-C₆)-alkoxy or (C₁-C₆)-haloalkoxy, R²³, R²⁴ independently of one another each represent hydrogen, (C₁-C₆)-alkyl, (C₂-C₆)-alkenyl, (C₂-C₆)-alkynyl, (C₃-C₈)-cycloalkyl, (C₁-C₆)-haloalkyl, (C₂-C₆)-haloalkenyl or (C₂-C₆)-haloalkynyl and m represents 0, 1 or 2.

DETAILED DESCRIPTION OF A PREFERRED EMBODIMENT

It has additionally been found that the compounds of formula (I) have very good efficacy as pesticides, preferably as insecticides and/or acaricides, and additionally generally have very good plant compatibility, in particular with respect to crop plants.

The compounds according to the invention are defined in general terms by the formula (I). Preferred substituents or ranges of the radicals given in the formulae mentioned above and below are illustrated hereinafter:

Configuration 2

Aa preferably represents nitrogen or C(R¹),
Ab preferably represents nitrogen or C(R²),
Ac preferably represents nitrogen or C(R³),
Ad preferably represents nitrogen or C(R⁴), where at most one of the groups Aa, Ab, Ac and Ad represents nitrogen, R¹, R², R³, R⁴ independently of one another preferably represent hydrogen, halogen, cyano, SF₅, (C₁-C₆)-alkyl, (C₁-C₆)-haloalkyl, (C₂-C₆)-alkenyl, (C₂-C₆)-haloalkenyl, (C₂-C₆)-alkynyl, (C₂-C₆)-haloalkynyl, (C₁-C₆)-alkoxy, (C₁-C₆)-haloalkoxy, (C₃-C₈)-cycloalkyl, halo-(C₃-C₈)-cycloalkyl, (C₁-C₆)-cyanoalkyl, cyano-(C₃-C₆)-cyclo alkyl, (C₁-C₆)-alkylthio, (C₁-C₆)-haloalkylthio, (C₁-C₆)-alkylsulfinyl, (C₁-C₆)-haloalkylsulfinyl, (C₁-C₆)-alkylsulfonyl or (C₁-C₆)-haloalkylsulfonyl, where at most two of the radicals R¹, R², R³ and R⁴ represent a radical other than hydrogen, Q preferably represents a heteroaromatic 8-, 9- or 10-membered fused bicyclic ring system from the group consisting of Q1 to Q9,

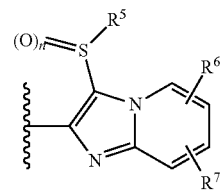

Q1

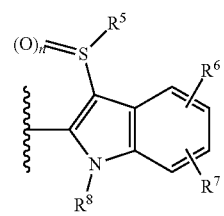

Q2

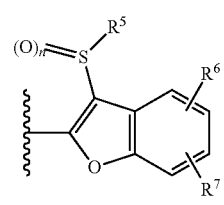

Q3

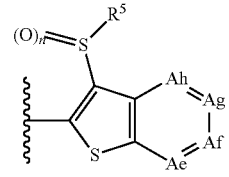

Q4

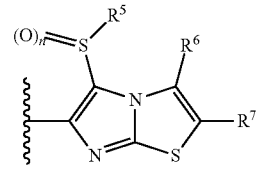

Q5

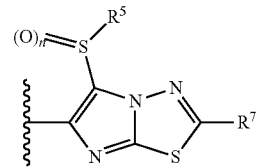

Q6

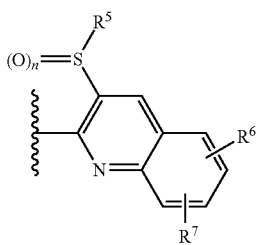

Q7

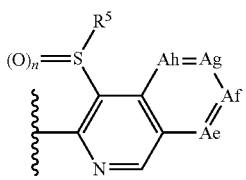

Q8

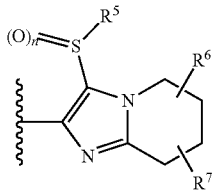

Q9

Ae preferably represents nitrogen, C(R⁶) or C(R⁷),
Af preferably represents nitrogen, C(R⁶) or C(R⁷),
Ag preferably represents nitrogen, C(R⁶) or C(R⁷),
Ah preferably represents nitrogen, C(R⁶) or C(R⁷),
where at most one of the groups Ae, Af, Ag and Ah represents nitrogen and R⁵ preferably represents $(C_1-C_4)$-alkyl, $(C_1-C_4)$-hydroxyalkyl, $(C_1-C_4)$-halo alkyl, $(C_2-C_4)$-alkenyl, $(C_2-C_4)$-haloalkenyl, $(C_2-C_4)$-alkynyl, $(C_2-C_4)$-haloalkynyl, $(C_3-C_6)$-cycloalkyl, $(C_3-C_6)$-halocycloalkyl, $(C_1-C_4)$-alkylthio-$(C_1-C_4)$-alkyl, $(C_1-C_4)$-alkylsulfinyl-$(C_1-C_4)$-alkyl or $(C_1-C_4)$-alkylsulfonyl-$(C_1-C_4)$-alkyl, R⁶, R⁷ independently of one another each preferably represent hydrogen, halogen, cyano, nitro, SCN, SF₅, $(C_1-C_6)$-alkyl, $(C_1-C_6)$-haloalkyl, $(C_1-C_6)$-haloalkoxy, $(C_1-C_6)$-alkoxy, $(C_2-C_6)$-alkenyl, $(C_2-C_6)$-haloalkenyl, $(C_2-C_6)$-alkynyl, $(C_2-C_6)$-haloalkynyl, $(C_3-C_8)$-cycloalkyl, $(C_3-C_8)$-halocycloalkyl, $(C_3-C_6)$-cycloalkyl-$(C_1-C_6)$-alkyl, $(C_3-C_6)$-cyclo alkyl-$(C_1-C_6)$-halo alkyl, $(C_1-C_6)$-alkyl-$(C_3-C_8)$-cycloalkyl, $(C_1-C_6)$-haloalkyl-$(C_3-C_8)$-cycloalkyl, $(C_3-C_6)$-cycloalkyl-$(C_3-C_6)$-cycloalkyl, spiro-$(C_3-C_6)$-cyclo alkyl-$(C_3-C_6)$-cyclo alkyl, $(C_4-C_{12})$-bicycloalkyl, $(C_1-C_6)$-cyanoalkyl, $(C_3-C_6)$-cyanocycloalkyl, $(C_1-C_6)$-hydroxyalkyl, $(C_1-C_6)$-alkoxycarbonyl-$(C_1-C_6)$-alkyl, $(C_1-C_6)$-alkoxy-$(C_1-C_6)$-alkyl, $(C_2-C_6)$-cyano alkenyl, $(C_3-C_6)$-cycloalkyl-$(C_2-C_6)$-alkenyl, $(C_2-C_6)$-cyanoalkynyl, $(C_3-C_6)$-cycloalkyl-$(C_2-C_6)$-alkynyl, $(C_1-C_6)$-haloalkoxy-$(C_1-C_6)$-alkyl, $(C_1-C_6)$-alkylthio-$(C_1-C_6)$-alkyl, $(C_1-C_6)$-alkylsulfinyl-$(C_1-C_6)$-alkyl, $(C_1-C_6)$-alkyl sulfonyl-$(C_1-C_6)$-alkyl, $(C_1-C_6)$-alkylcarbonyl-$(C_1-C_6)$-alkyl or R⁶, R⁷ independently of one another each preferably represent groups selected from —C(=O)—R²¹, —C(=S)—R²¹, —C(=O)—OR²¹, —C(=O)—NR²⁰R²¹, —C(=S)—NR²⁰R²¹, —CH(=N—OR²³), —CH(=N—NR²³R²⁴), —OR²¹, —OC(=O)—NR²⁰R²¹, —NR²⁰R²¹, —N(R²⁰)—NR²¹R²², —N(R²⁰)—C(=O)—R²¹, —N(R²⁰)—C(=S)—R²¹, —N(R²⁰)—C(=O)—OR²¹, —N(R²⁰)—C(=S)—OR²¹, —N(R²⁰)—C(=O)—NR²¹R²², —N(R²⁰)—C(=S)—NR²¹R²² or —S(=O)$_m$—R²¹, where R²⁰, R²¹, R²² independently of one another each represent hydrogen or represent $(C_1-C_6)$-alkyl, $(C_1-C_6)$-halo alkyl, $(C_1-C_6)$-alkoxy, $(C_1-C_6)$-halo alkoxy, $(C_2-C_6)$-alkenyl, $(C_2-C_6)$-alkynyl, $(C_3-C_8)$-halocycloalkyl or $(C_3-C_8)$-cycloalkyl, each of which is optionally mono- or polysubstituted by identical or different substituents, where the substituents independently of one another may be selected from halogen, cyano, hydroxy, hydroxycarbonyl, $(C_1-C_6)$-alkyl, $(C_1-C_6)$-haloalkyl, $(C_3-C_8)$-cyclo alkyl, $(C_1-C_6)$-alkoxy, $(C_1-C_6)$-halo alkoxy, amino, $(C_1-C_6)$-alkylcarbonyl, $(C_1-C_6)$-alkoxycarbonyl, $(C_1-C_6)$-alkylthio, $(C_1-C_6)$-alkyl sulfinyl, $(C_1-C_6)$-alkylsulfonyl, $(C_1-C_4)$-halo alkylthio, $(C_1-C_4)$-halo alkyl sulfinyl, $(C_1-C_4)$-haloalkylsulfonyl or $(C_1-C_6)$-alkyl sulfonyloxy, R²³, R²⁴ independently of one another each preferably represent hydrogen, $(C_1-C_6)$-alkyl, $(C_2-C_6)$-alkenyl, $(C_2-C_6)$-alkynyl, $(C_3-C_8)$-cycloalkyl, $(C_3-C_8)$-halocycloalkyl, $(C_1-C_6)$-haloalkyl, $(C_2-C_6)$-haloalkenyl or $(C_2-C_6)$-haloalkynyl, m preferably represents 0, 1 or 2 and R⁸ preferably represents $(C_1-C_4)$-alkyl, $(C_1-C_4)$-haloalkyl, $(C_1-C_4)$-cyanoalkyl, $(C_1-C_4)$-alkoxy-$(C_1-C_4)$-alkyl, $(C_1-C_4)$-haloalkoxy-$(C_1-C_4)$-alkyl or $(C_3-C_6)$-cycloalkyl and n preferably represents 0, 1 or 2.

Configuration 3

Aa particularly preferably represents nitrogen or C(R¹),
Ab particularly preferably represents nitrogen or C(R²),
Ac particularly preferably represents nitrogen or C(R³),
Ad particularly preferably represents nitrogen or C(R⁴),
where at most one of the groups Aa, Ab, Ac and Ad represents nitrogen, R¹, R², R³, R⁴ each independently of one another particularly preferably represent hydrogen, halogen, cyano, SF₅, $(C_1-C_4)$-alkyl, $(C_1-C_4)$-halo alkyl, $(C_1-C_4)$-haloalkoxy, $(C_3-C_6)$-cyclo alkyl, $(C_1-C_4)$-cyano alkyl, cyano-$(C_3-C_6)$-cyclo alkyl, $(C_1-C_4)$-alkylthio, $(C_1-C_4)$-haloalkylthio, $(C_1-C_4)$-alkylsulfinyl, $(C_1-C_4)$-haloalkylsulfinyl, $(C_1-C_4)$-alkylsulfonyl or $(C_1-C_4)$-haloalkylsulfonyl, where at most two of the radicals R¹, R², R³ and R⁴ represent a radical other than hydrogen, Q particularly preferably represents a heteroaromatic 8-, 9- or 10-membered fused bicyclic ring system from the group consisting of Q1, Q4, Q5, Q7, Q8 and Q9,

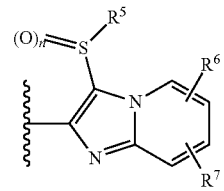

Q1

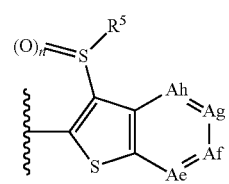

Q4

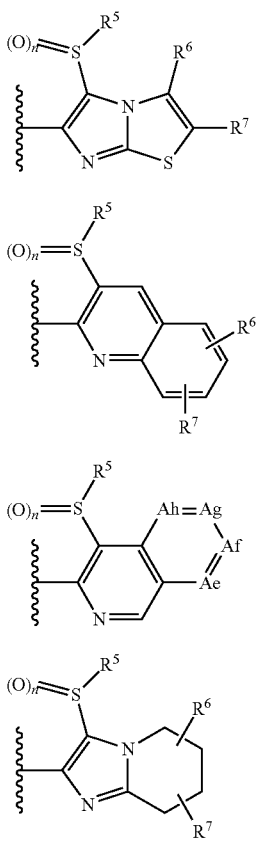

Ae particularly preferably represents nitrogen, $C(R^6)$ or $C(R^7)$,
Af particularly preferably represents nitrogen, $C(R^6)$ or $C(R^7)$,
Ag particularly preferably represents nitrogen, $C(R^6)$ or $C(R^7)$,
Ah particularly preferably represents nitrogen, $C(R^6)$ or $C(R^7)$,
where at most one of the groups Ae, Af, Ag and Ah represents nitrogen,
$R^5$ particularly preferably represents $(C_1-C_4)$-alkyl, $(C_1-C_4)$-haloalkyl or $(C_3-C_6)$-cycloalkyl,
$R^6$ particularly preferably represents hydrogen,
$R^7$ particularly preferably represents hydrogen, halogen, cyano, $SF_5$, $(C_1-C_4)$-alkyl, $(C_1-C_4)$-haloalkyl, $(C_1-C_4)$-haloalkoxy, $(C_1-C_4)$-alkoxy, $(C_3-C_6)$-cycloalkyl, $(C_3-C_6)$-halocycloalkyl, $(C_3-C_6)$-cycloalkyl-$(C_1-C_4)$-alkyl, $(C_3-C_6)$-cycloalkyl-$(C_1-C_4)$-haloalkyl, $(C_1-C_4)$-alkyl-$(C_3-C_6)$-cycloalkyl, $(C_1-C_4)$-haloalkyl-$(C_3-C_6)$-cycloalkyl, $(C_1-C_4)$-cyanoalkyl, cyano-$(C_3-C_6)$-cycloalkyl or
$R^7$ particularly preferably represents a group selected from
—$C(=O)$—$R^{21}$, —$C(=S)$—$R^{21}$, —$C(=O)$—$OR^{21}$, —$C(=O)$—$NR^{20}R^{21}$, —$C(=S)$—$NR^{20}R^{21}$, —$CH(=N$—$OR^{23})$, —$CH(=N$—$NR^{23}R^{24})$, —$OR^{21}$, —$OC(=O)$—$NR^{20}R^{21}$, —$NR^{20}R^{21}$, —$N(R^{20})$—$NR^{21}R^{22}$, —$N(R^{20})$—$C(=O)$—$R^{21}$, —$N(R^{20})$—$C(=S)$—$R^{21}$, —$N(R^{20})$—$C(=O)$—$OR^{21}$, —$N(R^{20})$—$C(=S)$—$OR^{21}$, —$N(R^{20})$—$C(=O)$—$NR^{21}R^{22}$, —$N(R^{20})$—$C(=S)$—$NR^{21}R^{22}$ or —$S(=O)_m$—$R^{21}$, where
$R^{20}$, $R^{21}$, $R^{22}$ each independently of one another particularly preferably represent hydrogen or represent $(C_1-C_4)$-alkyl, $(C_1-C_4)$-haloalkyl, $(C_1-C_4)$-alkoxy, $(C_1-C_4)$-halo alkoxy, $(C_2-C_6)$-alkenyl, $(C_2-C_6)$-alkynyl, $(C_3-C_6)$-halocycloalkyl or $(C_3-C_6)$-cycloalkyl, each of which is optionally mono- or polysubstituted by identical or different substituents, where the substituents independently of one another may be selected from halogen, cyano, $(C_1-C_4)$-alkyl, $(C_1-C_4)$-haloalkyl, $(C_3-C_6)$-cycloalkyl, $(C_1-C_4)$-alkoxy or $(C_1-C_4)$-halo alkoxy,
$R^{23}$, $R^{24}$ each independently of one another particularly preferably represent hydrogen, $(C_1-C_4)$-alkyl, $(C_2-C_6)$-alkenyl, $(C_2-C_6)$-alkynyl, $(C_3-C_6)$-cycloalkyl, $(C_3-C_6)$-halocycloalkyl, $(C_1-C_4)$-haloalkyl, $(C_2-C_6)$-haloalkenyl or $(C_2-C_6)$-haloalkynyl and
m particularly preferably represents 0, 1 or 2 and
n particularly preferably represents 0, 1 or 2.

Configuration 4
Aa very particularly preferably represents nitrogen or $C(R^1)$,
Ab very particularly preferably represents nitrogen or $C(R^2)$,
Ac very particularly preferably represents nitrogen or $C(R^3)$,
Ad very particularly preferably represents nitrogen or $C(R^4)$,
where at most one of the groups Aa, Ab, Ac and Ad represents nitrogen,
$R^1$, $R^2$, $R^3$, $R^4$ independently of one another very particularly preferably represent hydrogen, halogen, cyano, $(C_1-C_4)$-alkyl, $(C_1-C_4)$-haloalkyl, $(C_1-C_4)$-haloalkoxy, $(C_3-C_6)$-cycloalkyl, $(C_1-C_4)$-cyanoalkyl, cyano-$(C_3-C_6)$-cycloalkyl, $(C_1-C_4)$-haloalkylthio, $(C_1-C_4)$-halo alkylsulfinyl or $(C_1-C_4)$-haloalkylsulfonyl,
where at most one of the radicals $R^1$, $R^2$, $R^3$ and $R^4$ represents a radical other than hydrogen,
Q very particularly preferably represents a heteroaromatic 8-, 9- or 10-membered fused bicyclic ring system from the group consisting of Q1, Q4, Q5, Q7, Q8 and Q9,

Q1

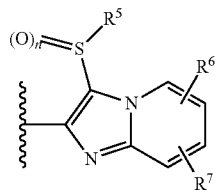

Q4

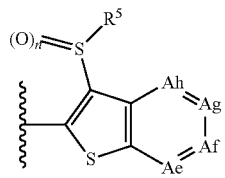

Q5

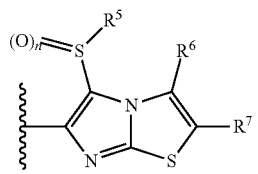

Q7

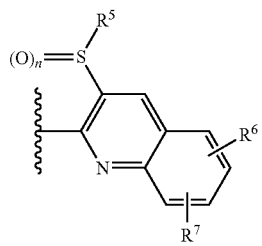

-continued

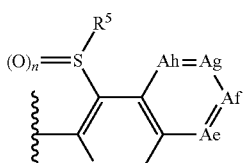
Q8

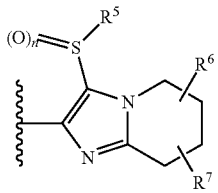
Q9

Ae very particularly preferably represents nitrogen, C(R$^6$) or C(R$^7$),
Af very particularly preferably represents nitrogen, C(R$^6$) or C(R$^7$),
Ag very particularly preferably represents nitrogen, C(R$^6$) or C(R$^7$),
Ah very particularly preferably represents nitrogen, C(R$^6$) or C(R$^7$),
where at most one of the groups Ae, Af, Ag and Ah represents nitrogen,
R$^5$ very particularly preferably represents (C$_1$-C$_4$)-alkyl or (C$_3$-C$_4$)-cycloalkyl,
R$^6$ very particularly preferably represents hydrogen,
R$^7$ very particularly preferably represents hydrogen, halogen, cyano, SF$_5$, (C$_1$-C$_4$)-alkyl, (C$_1$-C$_4$)-haloalkyl, (C$_1$-C$_4$)-haloalkoxy, (C$_1$-C$_4$)-alkoxy, (C$_3$-C$_6$)-cycloalkyl, (C$_3$-C$_6$)-halocycloalkyl, (C$_3$-C$_6$)-cycloalkyl-(C$_1$-C$_4$)-alkyl, (C$_3$-C$_6$)-cycloalkyl-(C$_1$-C$_4$)-haloalkyl, (C$_1$-C$_4$)-alkyl-(C$_3$-C$_6$)-cycloalkyl, (C$_1$-C$_4$)-haloalkyl-(C$_3$-C$_6$)-cycloalkyl, (C$_1$-C$_4$)-cyanoalkyl, cyano-(C$_3$-C$_6$)-cycloalkyl or
R$^7$ very particularly preferably represents a group selected from —C(=O)—R$^{21}$, —C(=S)—R$^{21}$, C(=O)—OR$^{21}$, —C(=O)—NR$^{20}$R$^{21}$, —OR$^{21}$, —NR$^{20}$R$^{21}$, —N(R$^{20}$)—C(=O)—R$^{21}$, —S(=O)$_m$—R$^{21}$ or —N(R$^{20}$)—C(=S)—R$^{21}$,
where
R$^{20}$, R$^{21}$, R$^{22}$ each independently of one another very particularly preferably represent hydrogen or represent (C$_1$-C$_4$)-alkyl, (C$_1$-C$_4$)-haloalkyl, (C$_1$-C$_4$)-alkoxy, (C$_1$-C$_4$)-haloalkoxy, (C$_2$-C$_6$)-alkenyl, (C$_2$-C$_6$)-alkynyl, (C$_3$-C$_6$)-halocycloalkyl or (C$_3$-C$_6$)-cycloalkyl, each of which is optionally mono- or polysubstituted by identical or different substituents, where the substituents independently of one another may be selected from halogen, cyano, (C$_1$-C$_4$)-alkyl, (C$_1$-C$_4$)-haloalkyl, (C$_3$-C$_6$)-cycloalkyl, (C$_1$-C$_4$)-alkoxy or (C$_1$-C$_4$)-haloalkoxy, and
m particularly preferably represents 2 and
n very particularly preferably represents 0, 1 or 2.
Configuration 5-1
Aa with emphasis represents nitrogen or CH,
Ab with emphasis represents nitrogen or C(R$^2$),
Ac with emphasis represents nitrogen or C(R$^3$),
Ad with emphasis represents CH,
where at most one of the groups Aa, Ab and Ac represents nitrogen,
R$^2$, R$^3$ independently of one another with emphasis represent hydrogen or (C$_1$-C$_6$)-haloalkyl, Q with emphasis represents a heteroaromatic 8-, 9- or 10-membered fused bicyclic ring system from the group consisting of Q1, Q7, Q8 and Q9,

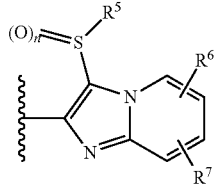
Q1

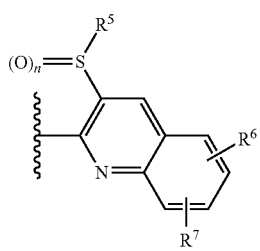
Q7

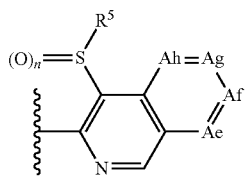
Q8

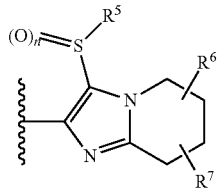
Q9 where
Ae with emphasis represents CH,
Af with emphasis represents CH,
Ag with emphasis represents CH,
Ah with emphasis represents CH,
R$^5$ with emphasis represents (C$_1$-C$_4$)-alkyl,
R$^6$ with emphasis represents hydrogen,
R$^7$ with emphasis represents hydrogen, halogen, (C$_1$-C$_4$)-alkyl, (C$_1$-C$_4$)-haloalkyl, (C$_3$-C$_6$)-cycloalkyl or —N(R$^{20}$)—C(=O)—R$^{21}$, —C(=O)OR$^{21}$, —S(=O)$_m$—R$^{21}$ or (C$_1$-C$_4$)-haloalkoxy,
where R$^{20}$ with emphasis represents hydrogen,
R$^{21}$ with emphasis represents (C$_3$-C$_6$)-cycloalkyl, (C$_1$-C$_4$)-alkyl or (C$_1$-C$_4$)-alkoxy
and m with emphasis represents 2,
preferably R$^7$
in the case that Q=Q1 with emphasis represents 3-halogen, 3-(C$_1$-C$_4$)-haloalkyl, 3-(C$_3$-C$_6$)-cycloalkyl, 3-(C$_1$-C$_4$)-haloalkoxy, 3-S(=O)$_m$—R$^{21}$, —C(=O)—OR$^{21}$ or 3-N(R$^{20}$)—C(=O)—R$^{21}$,
where R$^{20}$ with emphasis represents hydrogen,
R$^{21}$ with emphasis represents (C$_3$-C$_6$)-cycloalkyl, (C$_1$-C$_4$)-alkoxy or (C$_1$-C$_4$)-alkyl
and m with emphasis represents 2,
in the case that Q=Q7, Q8 or Q9 with emphasis represents hydrogen, and
n with emphasis represents 2.
Configuration 6-1
Aa especially represents nitrogen or CH,
Ab especially represents nitrogen or C(R$^2$), Ac especially represents nitrogen or C(R³),
Ad especially represents CH,
where at most one of the groups Aa, Ab and Ac represents nitrogen,
R² especially represents hydrogen or trifluoromethyl,
R³ especially represents hydrogen or trifluoromethyl,
Q especially represents a heteroaromatic 8-, 9- or 10-membered fused bicyclic ring system from the group consisting of Q1, Q7, Q8 and Q9,

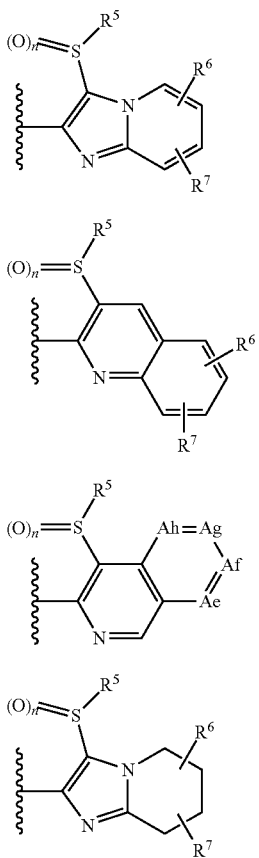

where
Ae especially represents CH,
Af especially represents CH,
Ag especially represents CH,
Ah especially represents CH,
R⁵ especially represents ethyl,
R⁶ especially represents hydrogen,
R⁷ especially represents hydrogen, iodine, cyclopropyl, —SO₂-cyclopropyl, —OCH₂CF₃, —NHCOMe, —NHCOOMe, —COOMe, trifluoromethyl or NHCO-cyclopropyl,
preferably R⁷
in the case that Q=Q1 especially represents 3-iodine, 3-cyclopropyl, 3-SO₂-cyclopropyl, 3-trifluoromethyl, 3-OCH₂CF₃, 3-NHCOMe, 3-NHCOOMe, 3-COOMe or 3-NHCO-cyclopropyl,
in the case that Q=Q7, Q8 or Q9 represents hydrogen, and
n especially represents 2.

Further alternative embodiments of formula (I) are illustrated below:
Configuration 5-2
Aa with emphasis represents CH,
Ab with emphasis represents nitrogen or C(R²),
Ac with emphasis represents nitrogen or C(R³),
Ad with emphasis represents CH,
where at most one of the groups Ab and Ac represents nitrogen,
R², R³ independently of one another with emphasis represent hydrogen or (C₁-C₆)-haloalkyl,
Q with emphasis represents a heteroaromatic 8-, 9- or 10-membered fused bicyclic ring system from the group consisting of Q1, Q4, Q5, Q7 and Q9,

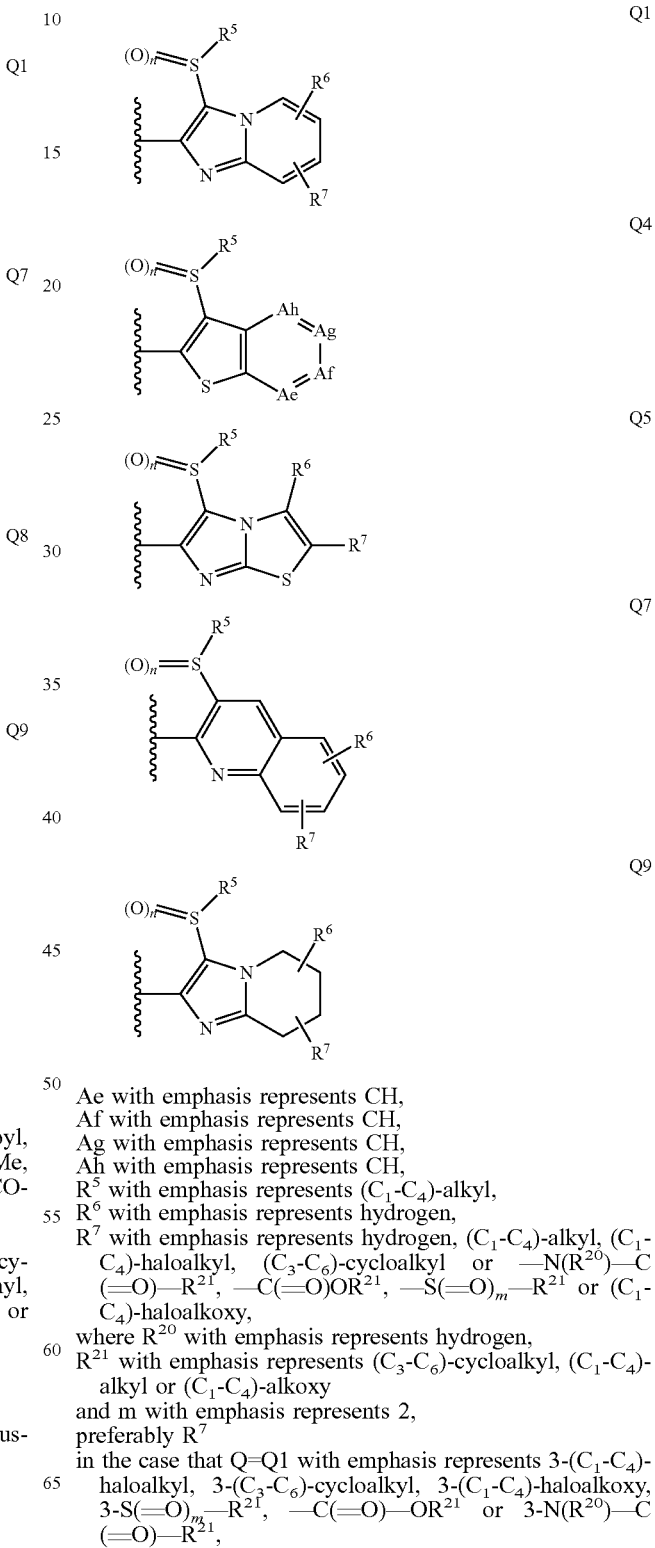

Ae with emphasis represents CH,
Af with emphasis represents CH,
Ag with emphasis represents CH,
Ah with emphasis represents CH,
R⁵ with emphasis represents (C₁-C₄)-alkyl,
R⁶ with emphasis represents hydrogen,
R⁷ with emphasis represents hydrogen, (C₁-C₄)-alkyl, (C₁-C₄)-haloalkyl, (C₃-C₆)-cycloalkyl or —N(R²⁰)—C(=O)—R²¹, —C(=O)OR²¹, —S(=O)ₘ—R²¹ or (C₁-C₄)-haloalkoxy,
where R²⁰ with emphasis represents hydrogen,
R²¹ with emphasis represents (C₃-C₆)-cycloalkyl, (C₁-C₄)-alkyl or (C₁-C₄)-alkoxy
and m with emphasis represents 2,
preferably R⁷
in the case that Q=Q1 with emphasis represents 3-(C₁-C₄)-haloalkyl, 3-(C₃-C₆)-cycloalkyl, 3-(C₁-C₄)-haloalkoxy, 3-S(=O)ₘ—R²¹, —C(=O)—OR²¹ or 3-N(R²⁰)—C(=O)—R²¹, where $R^{20}$ with emphasis represents hydrogen,
$R^{21}$ with emphasis represents $(C_3-C_6)$-cycloalkyl, $(C_1-C_4)$-alkoxy or $(C_1-C_4)$-alkyl
and m with emphasis represents 2,
in the case that Q=Q5 with emphasis represents $(C_1-C_4)$-haloalkyl,
in the case that Q=Q7 with emphasis represents hydrogen and
in the case that Q=Q9 with emphasis represents hydrogen, 2-$(C_1-C_4)$-alkyl or 3-$(C_1-C_4)$-alkyl,
and
n with emphasis represents 2.
Configuration 6-2
Aa especially represents CH,
Ab especially represents nitrogen or $C(R^2)$,
Ac especially represents nitrogen or $C(R^3)$,
Ad especially represents CH,
where at most one of the groups Ab and Ac represents nitrogen,
$R^2$ especially represents hydrogen or trifluoromethyl,
$R^3$ especially represents hydrogen or trifluoromethyl,
Q especially represents a heteroaromatic fused bicyclic ring system from the group consisting of Q1, Q7 and Q9,

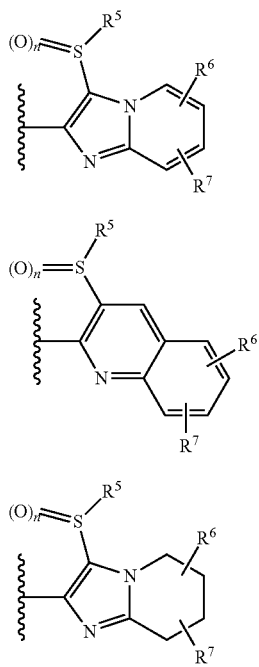

$R^5$ especially represents ethyl,
$R^6$ especially represents hydrogen,
$R^7$ especially represents hydrogen, —OCH$_2$CF$_3$, —NHCOMe, —NHCOOMe, —NHCO-cyclopropyl or trifluoromethyl,
preferably $R^7$
in the case that Q=Q1 especially represents 3-trifluoromethyl, 3-OCH$_2$CF$_3$, 3-NHCOMe, 3-NHCOOMe or 3-NHCO-cyclopropyl,
in the case that Q=Q7 especially represents hydrogen and
in the case that Q=Q9 especially represents hydrogen,
and
n especially represents 2.
Hereinbelow, Configuration (5) is equivalent to Configuration (5-1) or Configuration (5-2) and Configuration (6) is equivalent to Configuration (6-1) or Configuration (6-2).

In a further preferred configuration of the compounds of formula (I)
$R^2$, $R^3$ independently of one another represent hydrogen, $(C_1-C_4)$-haloalkylthio, $(C_1-C_4)$-haloalkylsulfinyl, $(C_1-C_4)$-haloalkylsulfonyl or $(C_1-C_4)$-haloalkyl, in particular trifluoromethyl, trifluoromethylsulfinyl, trifluoromethylsulfonyl or trifluoromethylthio, where only one of the radicals $R^2$ or $R^3$ does not represent hydrogen
and where $R^1$, $R^4$, $R^5$ and Q (including Ae, Af, Ag, Ah, $R^5$, $R^6$, $R^7$, $R^{20}$, $R^{21}$, $R^{22}$, $R^{23}$, $R^{24}$, $R^8$, m and n) have the meanings described above, in particular the meanings described in Configuration (1) or Configuration (2) or Configuration (3) or Configuration (4) or Configuration (5) or Configuration (6).

In a further preferred configuration of the compounds of formula (I)
Aa, Ab, Ac and Ad (including $R^1$, $R^2$, $R^3$ and $R^4$) have the meaning given in Configuration (1)
and Q (including Ae, Af, Ag, Ah, $R^5$, $R^6$, $R^7$, $R^{20}$, $R^{21}$, $R^{22}$, $R^{23}$, $R^{24}$, $R^8$, m and n) have the meanings described in Configuration (2) or Configuration (3) or Configuration (4) or Configuration (5) or Configuration (6).

In a further preferred configuration of the compounds of formula (I)
$R^5$ represents $(C_1-C_4)$-alkyl, $(C_1-C_4)$-haloalkyl or $(C_3-C_6)$-cycloalkyl
and Aa, Ab, Ac and Ad (including $R^1$, $R^2$, $R^3$ and $R^4$) and Q, Ae, Af, Ag, Ah, $R^6$, $R^7$, $R^{20}$, $R^{21}$, $R^{22}$, $R^{23}$, $R^{24}$, $R^8$, m and n have the meanings described above, in particular the meanings described in Configuration (1) or Configuration (2) or Configuration (4) or Configuration (5) or Configuration (6).

In a further preferred configuration of the compounds of formula (I)
$R^5$ with emphasis represents $(C_1-C_4)$-alkyl
and Aa, Ab, Ac and Ad (including $R^1$, $R^2$, $R^3$ and $R^4$) and Q, Ae, Af, Ag, Ah, $R^6$, $R^7$, $R^{20}$, $R^{21}$, $R^{22}$, $R^{23}$, $R^{24}$, $R^8$, m and n have the meanings described above, in particular the meanings described in Configuration (1) or Configuration (2) or Configuration (3) or Configuration (4) or Configuration (6).

In a further preferred configuration of the compounds of formula (I)
$R^5$ with emphasis represents ethyl
and Aa, Ab, Ac and Ad (including $R^1$, $R^2$, $R^3$ and $R^4$) and Q, Ae, Af, Ag, Ah, $R^6$, $R^7$, $R^{20}$, $R^{21}$, $R^{22}$, $R^{23}$, $R^{24}$, $R^8$, m and n have the meanings described above, in particular the meanings described in Configuration (1) or Configuration (2) or Configuration (3) or Configuration (4) or Configuration (5).

In a further preferred configuration of the compounds of formula (I)
Q represents a heteroaromatic 8-, 9- or 10-membered fused bicyclic ring system from the group consisting of Q1 to Q9,
and Aa, Ab, Ac and Ad (including $R^1$, $R^2$, $R^3$ and $R^4$) and $R^5$, Ae, Af, Ag, Ah, $R^6$, $R^7$, $R^{20}$, $R^{21}$, $R^{22}$, $R^{23}$, $R^{24}$, $R^8$, m and n have the meanings described above, in particular the meanings described in Configuration (1) or Configuration (3) or Configuration (4) or Configuration (5) or Configuration (6).

In a further preferred configuration of the compounds of formula (I)
Q represents a heteroaromatic 8-, 9- or 10-membered fused bicyclic ring system from the group consisting of Q1, Q4, Q5, Q7, Q8 or Q9, and Aa, Ab, Ac and Ad (including $R^1$, $R^2$, $R^3$ and $R^4$) and $R^5$, Ae, Af, Ag, Ah, $R^6$, $R^7$, $R^{20}$, $R^{21}$, $R^{22}$, $R^{23}$, $R^{24}$, m and n have the meanings described above, in particular the meanings described in Configuration (1) or Configuration (2) or Configuration (5) or Configuration (6).

In a further preferred configuration of the compounds of formula (I)
Q represents a heteroaromatic 8-, 9- or 10-membered fused bicyclic ring system from the group consisting of Q1, Q7, Q8 or Q9,
and Aa, Ab, Ac and Ad (including $R^1$, $R^2$, $R^3$ and $R^4$) and $R^5$, Ae, Af, Ag, Ah, $R^6$, $R^7$, $R^{20}$, $R^{21}$, $R^{22}$, $R^{23}$, $R^{24}$, m and n have the meanings described above, in particular the meanings described in Configuration (1) or Configuration (2) or Configuration (3) or Configuration (4) or Configuration (5) or Configuration (6).

In a further preferred configuration of the compounds of formula (I)
Q represents a heteroaromatic 8-, 9- or 10-membered fused bicyclic ring system from the group consisting of Q7, Q8 or Q9,
and Aa, Ab, Ac and Ad (including $R^1$, $R^2$, $R^3$ and $R^4$) and $R^5$, Ae, Af, Ag, Ah, $R^6$, $R^7$, $R^{20}$, $R^{21}$, $R^{22}$, $R^{23}$, $R^{24}$, m and n have the meanings described above, in particular the meanings described in Configuration (1) or Configuration (2) or Configuration (3) or Configuration (4) or Configuration (5) or Configuration (6).

In a further preferred configuration of the compounds of formula (I)
Q represents a heteroaromatic 8-, 9- or 10-membered fused bicyclic ring system from the group consisting of Q7, Q8 or Q9,
$R^6$, $R^7$ represent hydrogen,
Ae, Af, Ag, Ah represent CH
and Aa, Ab, Ac and Ad (including $R^1$, $R^2$, $R^3$ and $R^4$), $R^5$ and n have the meanings described above, in particular the meanings described in Configuration (1) or Configuration (2) or Configuration (3) or Configuration (4) or Configuration (5) or Configuration (6).

In a further preferred configuration of the compounds of formula (I)
Aa represents CH,
Ab represents nitrogen or $C(R^2)$,
Ac represents nitrogen or $C(R^3)$,
Ad represents CH,
where at most one of the groups Ab and Ac represents nitrogen,
$R^2$, $R^3$ independently of one another represent hydrogen or $(C_1-C_6)$-haloalkyl,
Q represents a heteroaromatic 8-, 9- or 10-membered fused bicyclic ring system from the group consisting of Q7, Q8 or Q9,
$R^6$, $R^7$ represent hydrogen,
Ae, Af, Ag, Ah represent CH,
$R^5$ represents $(C_1-C_4)$-alkyl and
n represents 2.

In a further preferred configuration of the compounds of formula (I)
$R^6$ represents hydrogen
and Aa, Ab, Ac and Ad (including $R^1$, $R^2$, $R^3$ and $R^4$) and Q, $R^5$, Ae, Af, Ag, Ah, $R^7$, $R^{20}$, $R^{21}$, $R^{22}$, $R^{23}$, $R^{24}$, $R^8$, m and n have the meanings described above, in particular the meanings described in Configuration (1) or Configuration (2) or Configuration (3).

In a further preferred configuration of the compounds of formula (I) in the case that Q=Q1 $R^7$ is attached at the 2- or 3-position of the ring.

In a further preferred configuration of the compounds of formula (I)
Aa represents nitrogen or $C(R^1)$,
Ab represents nitrogen or $C(R^2)$,
Ac represents nitrogen or $C(R^3)$,
Ad represents CH,
where at most one of the radicals Aa, Ab or Ac represents nitrogen and at least one of the radicals $R^2$ or $R^3$ does not represent hydrogen and $R^1$ does not represent hydrogen only in the case where $R^3$ likewise does not represent hydrogen
and where $R^1$, $R^2$, $R^3$, $R^5$ and Q (including Ae, Af, Ag, Ah, $R^5$, $R^6$, $R^7$, $R^{20}$, $R^{21}$, $R^{22}$, $R^{23}$, $R^{24}$, $R^8$, m and n) have the meanings described above, in particular the meanings described in Configuration (1) or Configuration (2) or Configuration (3) or Configuration (4) or Configuration (5) or Configuration (6).

In a further preferred configuration of the compounds of formula (I)
Aa represents nitrogen or CH,
Ab represents nitrogen or $C(R^2)$,
Ac represents nitrogen or $C(R^3)$,
Ad represents CH,
where at most one of the radicals Aa, Ab or Ac represents nitrogen and at least one of the radicals $R^2$ or $R^3$ does not represent hydrogen
and where $R^2$, $R^3$, $R^5$ and Q (including Ae, Af, Ag, Ah, $R^5$, $R^6$, $R^7$, $R^{20}$, $R^{21}$, $R^{22}$, $R^{23}$, $R^{24}$, $R^8$, m and n) have the meanings described above, in particular the meanings described in Configuration (1) or Configuration (2) or Configuration (3) or Configuration (4) or Configuration (5) or Configuration (6).

In a further preferred configuration of the compounds of formula (I)
Q represents Q7
and Aa, Ab, Ac and Ad (including $R^1$, $R^2$, $R^3$ and $R^4$) and $R^5$, Ae, Af, Ag, Ah, $R^6$, $R^7$, $R^{20}$, $R^{21}$, $R^{22}$, $R^{23}$, $R^{24}$, m and n have the meanings described above, in particular the meanings described in Configuration (1) or Configuration (2) or Configuration (3) or Configuration (4) or Configuration (5) or Configuration (6).

In a further preferred configuration of the compounds of formula (I)
Q represents Q7,
$R^6$, $R^7$ represent hydrogen,
and Aa, Ab, Ac and Ad (including $R^1$, $R^2$, $R^3$ and $R^4$), $R^5$ and n have the meanings described above, in particular the meanings described in Configuration (1) or Configuration (2) or Configuration (3) or
Configuration (4) or Configuration (5) or Configuration (6).

In a further preferred configuration of the compounds of formula (I)
Aa represents CH,
Ab represents nitrogen or $C(R^2)$,
Ac represents nitrogen or $C(R^3)$,
Ad represents CH,
where at most one of the groups Ab and Ac represents nitrogen,
$R^2$, $R^3$ independently of one another represent hydrogen or $(C_1-C_6)$-haloalkyl,
Q represents Q7,
$R^6$, $R^7$ represent hydrogen,
$R^5$ represents $(C_1-C_4)$-alkyl and
n represents 2.

In a further preferred configuration of the compounds of formula (I)
Q represents Q8
and Aa, Ab, Ac and Ad (including $R^1$, $R^2$, $R^3$ and $R^4$) and $R^5$, Ae, Af, Ag, Ah, $R^6$, $R^7$, $R^{20}$, $R^{21}$, $R^{22}$, $R^{23}$, $R^{24}$, m and n have the meanings described above, in particular the meanings described in Configuration (1) or Configuration (2) or Configuration (3) or Configuration (4) or Configuration (5) or Configuration (6).

In a further preferred configuration of the compounds of formula (I)
Q represents Q8,
Ae, Af, Ag, Ah represent CH
and Aa, Ab, Ac and Ad (including $R^1$, $R^2$, $R^3$ and $R^4$), $R^5$ and n have the meanings described above, in particular the meanings described in Configuration (1) or Configuration (2) or Configuration (3) or Configuration (4) or Configuration (5) or Configuration (6).

In a further preferred configuration of the compounds of formula (I)
Aa represents CH,
Ab represents nitrogen or $C(R^2)$,
Ac represents nitrogen or $C(R^3)$,
Ad represents CH,
where at most one of the groups Ab and Ac represents nitrogen,
$R^2$, $R^3$ independently of one another represent hydrogen or $(C_1-C_6)$-haloalkyl,
Q represents Q8,
Ae, Af, Ag, Ah represent CH,
$R^5$ represents $(C_1-C_4)$-alkyl and
n represents 2.

In a further preferred configuration of the compounds of formula (I)
Q represents Q9
and Aa, Ab, Ac and Ad (including $R^1$, $R^2$, $R^3$ and $R^4$) and $R^5$, Ae, Af, Ag, Ah, $R^6$, $R^7$, $R^{20}$, $R^{21}$, $R^{22}$, $R^{23}$, $R^{24}$, m and n have the meanings described above, in particular the meanings described in Configuration (1) or Configuration (2) or Configuration (3) or Configuration (4) or Configuration (5) or Configuration (6).

In a further preferred configuration of the compounds of formula (I)
Q represents Q9,
$R^6$, $R^7$ represent hydrogen,
and Aa, Ab, Ac and Ad (including $R^1$, $R^2$, $R^3$ and $R^4$), $R^5$ and n have the meanings described above, in particular the meanings described in Configuration (1) or Configuration (2) or Configuration (3) or Configuration (4) or Configuration (5) or Configuration (6).

In a further preferred configuration of the compounds of formula (I)
Aa represents CH,
Ab represents CH,
Ac represents $C(R^3)$,
Ad represents CH,
$R^3$ represents hydrogen or $(C_1-C_6)$-haloalkyl,
Q represents Q9,
$R^6$, $R^7$ represent hydrogen,
$R^5$ represents $(C_1-C_4)$-alkyl and
n represents 2.

In a further preferred embodiment, the invention relates to compounds of formula (I-A)

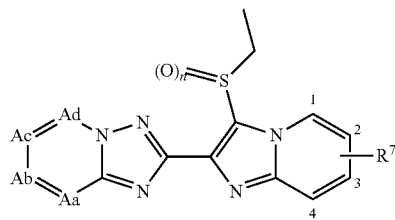

(I-A)

where Aa, Ab, Ac, Ad, $R^7$ and n have the meanings described above, in particular the meanings described in Configuration (1) or Configuration (2) or Configuration (3) or Configuration (4) or Configuration (5) or Configuration (6), and $R^7$ is preferably attached in the 2- or 3-position of the ring.

In a further preferred embodiment, the invention relates to compounds of formula (I-D)

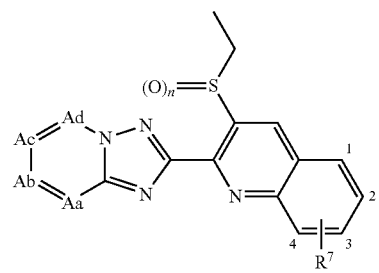

(I-D)

where Aa, Ab, Ac, Ad, Ae, Af, Ag, Ah, $R^7$ and n have the meanings described above, in particular the meanings described in Configuration (1) or Configuration (2) or Configuration (3) or Configuration (4) or Configuration (5) or Configuration (6).

In a further preferred embodiment, the invention relates to compounds of formula (I-D)

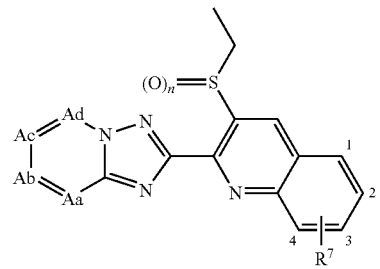

(I-D)

where $R^7$ represents hydrogen and Aa, Ab, Ac, Ad, Ae, Af, Ag, Ah and n have the meanings described above, in particular the meanings described in Configuration (1) or Configuration (2) or Configuration (3) or Configuration (4) or Configuration (5) or Configuration (6).

In a further preferred embodiment, the invention relates to compounds of formula (I-D)

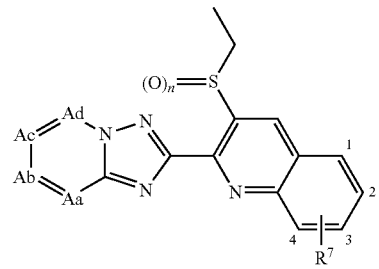

(I-D)

where
Aa represents CH,
Ab represents nitrogen or $C(R^2)$,
Ac represents nitrogen or $C(R^3)$,
Ad represents CH, where at most one of the groups Ab and Ac represents nitrogen,
$R^2$, $R^3$ independently of one another represent hydrogen or $(C_1-C_6)$-haloalkyl,
$R^7$ represents hydrogen and
n represents 2.

In a further preferred embodiment, the invention relates to compounds of formula (I-E)

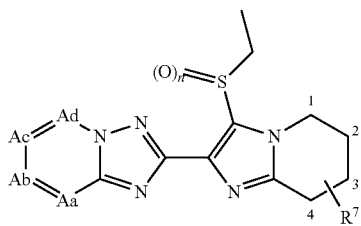
(I-E)

where Aa, Ab, Ac, Ad, $R^7$ and n have the meanings described above, in particular the meanings described in Configuration (1) or Configuration (2) or Configuration (3) or Configuration (4) or Configuration (5) or Configuration (6).

In a further preferred embodiment, the invention relates to compounds of formula (I-E)

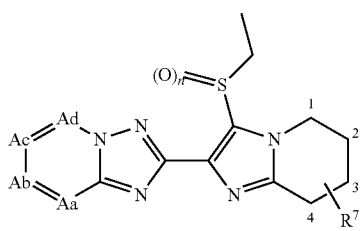
(I-E)

where $R^7$ represents hydrogen
and Aa, Ab, Ac, Ad and n have the meanings described above, in particular the meanings described in Configuration (1) or Configuration (2) or Configuration (3) or Configuration (4) or Configuration (5) or Configuration (6).

In a further preferred embodiment, the invention relates to compounds of formula (I-E)

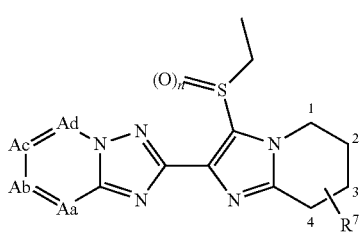
(I-E)

where
Aa represents CH,
Ab represents nitrogen or $C(R^2)$,
Ac represents nitrogen or $C(R^3)$,
Ad represents CH,
where at most one of the groups Ab and Ac represents nitrogen,
$R^2$, $R^3$ independently of one another represent hydrogen or $(C_1-C_6)$-haloalkyl,
$R^7$ represents hydrogen and
n represents 2.

In a further preferred embodiment, the invention relates to compounds of formula (I-F)

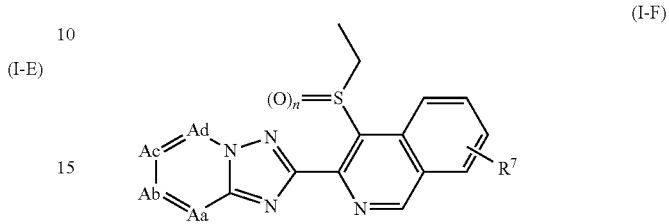
(I-F)

where Aa, Ab, Ac, Ad, $R^7$ and n have the meanings described above, in particular the meanings described in Configuration (1) or Configuration (2) or Configuration (3) or Configuration (4) or Configuration (5) or Configuration (6).

In a further preferred embodiment, the invention relates to compounds of formula (I-F)

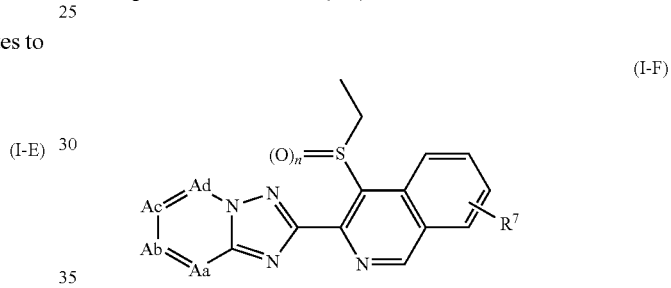
(I-F)

where $R^7$ represents hydrogen
and Aa, Ab, Ac, Ad and n have the meanings described above, in particular the meanings described in Configuration (1) or Configuration (2) or Configuration (3) or Configuration (4) or Configuration (5) or Configuration (6).

In a further preferred embodiment, the invention relates to compounds of formula (I-F)

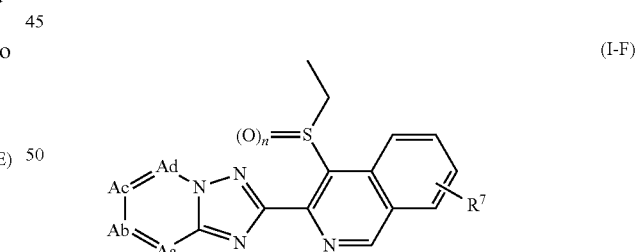
(I-F)

where
Aa represents CH,
Ab represents CH,
Ac represents $C(R^3)$,
Ad represents CH,
$R^3$ represents hydrogen or $(C_1-C_6)$-haloalkyl,
$R^7$ represents hydrogen and
n represents 2.

A particularly preferred embodiment of the invention relates to compounds of formula (I)
where Aa, Ab, Ac and Ad (including $R^1$, $R^2$, $R^3$ and $R^4$), Q, $R^5$, Ae, Af, Ag, Ah, $R^6$, $R^7$, $R^{20}$, $R^{21}$, $R^{22}$, $R^{23}$, $R^{24}$, m and n have the meanings described above, in particular the meanings described in Configuration (2) or Configuration (3) or Configuration (4) or Configuration (5) or Configuration (6) and
where for Q=Q1, Q2, Q3 and Q4
at least one of the radicals $R^6$ or $R^7$ does not represent hydrogen, halogen, ($C_3$-$C_6$)-cycloalkyl, cyano-, —C(O)OH— or —C(O)$NH_2$-substituted ($C_3$-$C_6$)-cyclo alkyl, ($C_1$-$C_6$)-alkyl, ($C_1$-$C_6$)-halo alkyl, ($C_1$-$C_6$)-alkoxy, ($C_1$-$C_6$)-haloalkoxy, ($C_1$-$C_6$)-alkylthio, halo-($C_1$-$C_6$)-alkylthio, ($C_1$-$C_6$)-alkylsulfinyl, halo-($C_1$-$C_6$)-alkylsulfinyl, ($C_1$-$C_6$)-alkylsulfonyl, halo-($C_1$-$C_6$)-alkylsulfonyl, —$NH_2$, —$NHR^x$, cyano or nitro, where R' represents ($C_1$-$C_6$)-alkyl, ($C_1$-$C_6$)-halo alkyl, ($C_1$-$C_6$)-alkylcarbonyl, halo-($C_1$-$C_6$)-alkylcarbonyl, ($C_1$-$C_6$)-alkoxycarbonyl, halo-($C_1$-$C_6$)-alkoxycarbonyl, ($C_1$-$C_6$)-alkylsulfonyl or halo-($C_1$-$C_6$)-alkylsulfonyl
and
where for Q=Q5 and Q6
$R^7$ does not represent hydrogen, halogen, ($C_1$-$C_6$)-alkyl or ($C_1$-$C_6$)-haloalkyl.

A very particularly preferred embodiment of the invention relates to compounds of formula (I)
where Aa, Ab, Ac and Ad (including $R^1$, $R^2$, $R^3$ and $R^4$), Q, $R^5$, Ae, Af, Ag, Ah, $R^6$, $R^7$, $R^{20}$, $R^{21}$, $R^{22}$, $R^{23}$, $R^{24}$, m and n have the meanings described above, in particular the meanings described in Configuration (2) or Configuration (3) or Configuration (4) or Configuration (5) or Configuration (6) and where, if
Aa represents CH,
Ab represents C($R^2$),
Ac represents CH and
Ad represents CH
or
Aa represents CH,
Ab represents C($R^2$),
Ac represents N and
Ad represents CH
or
Aa represents CH,
Ab represents C($R^2$),
Ac represents CH and
Ad represents N,
where $R^2$ represents —$CF_3$, —$SOCF_3$, —$SCF_3$, —$SO_2CF_3$
and for Q=Q1 $R^6$ is located at position 2 or 4 and represents H, F, Cl, Br, I, Me, —$CF_3$, —SMe, —SOMe, —$SO_2Me$, —OMe, —$OCF_3$, —$NO_2$, $NH_2$, CN, —$SOCF_3$, —$SCF_3$ or —$SO_2CF_3$ and $R^7$ is located at position 3,
then for Q=Q1 $R^7$ does not represent H, F, Cl, Br, I, Me, —$CF_3$, —SMe, —SOMe, —$SO_2Me$, —OMe, —$OCF_3$, —$NO_2$, $NH_2$, CN, —$SOCF_3$, —$SCF_3$, —$SO_2CF_3$ or cyclopropyl
or
if
Aa represents CH,
Ab represents C($R^2$),
Ac represents CH and
Ad represents CH
or
Aa represents CH,
Ab represents C($R^2$),
Ac represents N and
Ad represents CH
or
Aa represents CH,
Ab represents C($R^2$),
Ac represents CH and
Ad represents N,
where $R^2$ represents —$CF_3$,
and for Q=Q4 Ae or Ag represents C($R^6$) and $R^6$ represents H, F, Cl, Br, I, Me, —$CF_3$, —SMe, —SOMe, —$SO_2Me$, —OMe, —$OCF_3$, —$NO_2$, $NH_2$, CN, —$SOCF_3$, —$SCF_3$ or —$SO_2CF_3$ and Af represents C($R^7$),
then for Q=Q4 $R^7$ does not represent H, F, Cl, Br, I, Me, —$CF_3$, —SMe, —SOMe, —$SO_2Me$, —OMe, —$OCF_3$, —$NO_2$, $NH_2$, CN, —$SOCF_3$, —$SCF_3$, —$SO_2CF_3$ or cyclopropyl
or
if
Aa represents CH,
Ab represents C($R^2$),
Ac represents CH and
Ad represents CH
or
Aa represents CH,
Ab represents C($R^2$),
Ac represents N and
Ad represents CH
or
Aa represents CH,
Ab represents C($R^2$),
Ac represents CH and
Ad represents N,
where $R^2$ represents —$CF_3$,
and for Q=Q5 $R^6$ represents H,
then for Q=Q5 and Q=Q6 $R^7$ does not represent H, F, Cl, Br, I, Me or —$CF_3$.

The following statements regarding the compounds of formula (I) also apply to the compounds of formulae (I-A) to (I-F), which are encompassed by formula (I).

The compounds of formula (I) can also be present as salts, in particular acid addition salts and metal salt complexes. The compounds of formula (I) and the acid addition salts and metal salt complexes thereof have good efficacy, especially for controlling animal pests, which include arthropods and in particular insects and acarids.

Suitable salts of the compounds of the general formula (I) include customary nontoxic salts, i.e. salts with appropriate bases and salts with added acids. Preference is given to salts with inorganic bases, such as alkali metal salts, for example sodium, potassium or caesium salts, alkaline earth metal salts, for example calcium or magnesium salts, ammonium salts, salts with organic bases and with inorganic amines, for example triethylammonium, dicyclohexylammonium, N,N'-dibenzylethylenediammonium, pyridinium, picolinium or ethanolammonium salts, salts with inorganic acids, for example hydrochlorides, hydrobromides, dihydrosulfates, trihydrosulfates, or phosphates, salts with organic carboxylic acids or organic sulfonic acids, for example formates, acetates, trifluoroacetates, maleates, tartrates, methanesulfonates, benzenesulfonates or para-toluenesulfonates, salts with basic amino acids, for example arginates, aspartates or glutamates, and the like.

By definition, unless stated otherwise, halogen is selected from the group of fluorine, chlorine, bromine and iodine, preferably in turn from the group of fluorine, chlorine and bromine.

In the context of the present invention, unless defined differently elsewhere, the term "alkyl", either on its own or else in combination with further terms, for example haloalkyl, is understood to mean a radical of a saturated aliphatic hydrocarbon group which has 1 to 12 carbon atoms and may be branched or unbranched. Examples of $C_1$-$C_{12}$-alkyl radicals are methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1-ethylpropyl, 1,2-dimethylpropyl, hexyl, n-heptyl, n-octyl, n-nonyl, n-decyl, n-undecyl and n-dodecyl.

According to the invention, unless defined differently elsewhere, the term "alkenyl", either on its own or else in combination with further terms, is understood to mean a straight-chain or branched $C_2$-$C_{12}$-alkenyl radical which has at least one double bond, for example vinyl, allyl, 1-propenyl, isopropenyl, 1-butenyl, 2-butenyl, 3-butenyl, 1,3-butadienyl, 1-pentenyl, 2-pentenyl, 3-pentenyl, 4-pentenyl, 1,3-pentadienyl, 1-hexenyl, 2-hexenyl, 3-hexenyl, 4-hexenyl, 5-hexenyl and 1,4-hexadienyl.

According to the invention, unless defined differently elsewhere, the term "alkynyl", either on its own or else in combination with further terms, is understood to mean a straight-chain or branched $C_2$-$C_{12}$-alkynyl radical which has at least one triple bond, for example ethynyl, 1-propynyl and propargyl. The alkynyl radical may also contain at least one double bond.

According to the invention, unless defined differently elsewhere, the term "cycloalkyl", either on its own or else in combination with further terms, is understood to mean a $C_3$-$C_8$-cycloalkyl radical, for example cyclopropyl, cyclobutyl, cyclopentyl, cyclohexyl, cycloheptyl and cyclooctyl.

The term "alkoxy", either on its own or else in combination with further terms, for example haloalkoxy, is understood to mean in the present case an O-alkyl radical, where the term "alkyl" is as defined above.

Halogen-substituted radicals, for example haloalkyl, are mono- or polyhalogenated up to the maximum number of possible substituents. In the case of polyhalogenation, the halogen atoms may be identical or different. Unless stated otherwise, optionally substituted radicals may be mono- or polysubstituted, where the substituents in the case of polysubstitutions may be the same or different.

Depending on the nature of the substituents, the compounds of formula (I) may be in the form of geometric and/or optically active isomers or corresponding isomer mixtures in different compositions. These stereoisomers are, for example, enantiomers, diastereomers, atropisomers or geometric isomers. The invention therefore encompasses pure stereoisomers and any desired mixtures of these isomers.

The compounds of formula (I) may be present in different polymorphic forms or as a mixture of different polymorphic forms. Both the pure polymorphs and the polymorph mixtures are provided by the invention and can be used in accordance with the invention.

The radical definitions or illustrations given above in general terms or listed within ranges of preference apply correspondingly to end products and to starting materials and intermediates. These radical definitions can be combined with one another as desired, i.e. including combinations between the respective ranges of preference.

Preference according to the invention is given to using compounds of formula (I) which contain a combination of the meanings listed above as being preferred.

Particular preference according to the invention is given to using compounds of formula (I) which contain a combination of the meanings listed above as being particularly preferred.

Very particular preference according to the invention is given to using compounds of formula (I) which contain a combination of the definitions listed above as being very particularly preferred.

Emphasis according to the invention is given to using compounds of formula (I) which contain a combination of the meanings listed above as being emphasized.

Especially used according to the invention are compounds of formula (I) which contain a combination of the meanings listed above as being special.

The compounds of formula (I) according to the invention can be obtained by the processes shown in the following schemes:

Process A

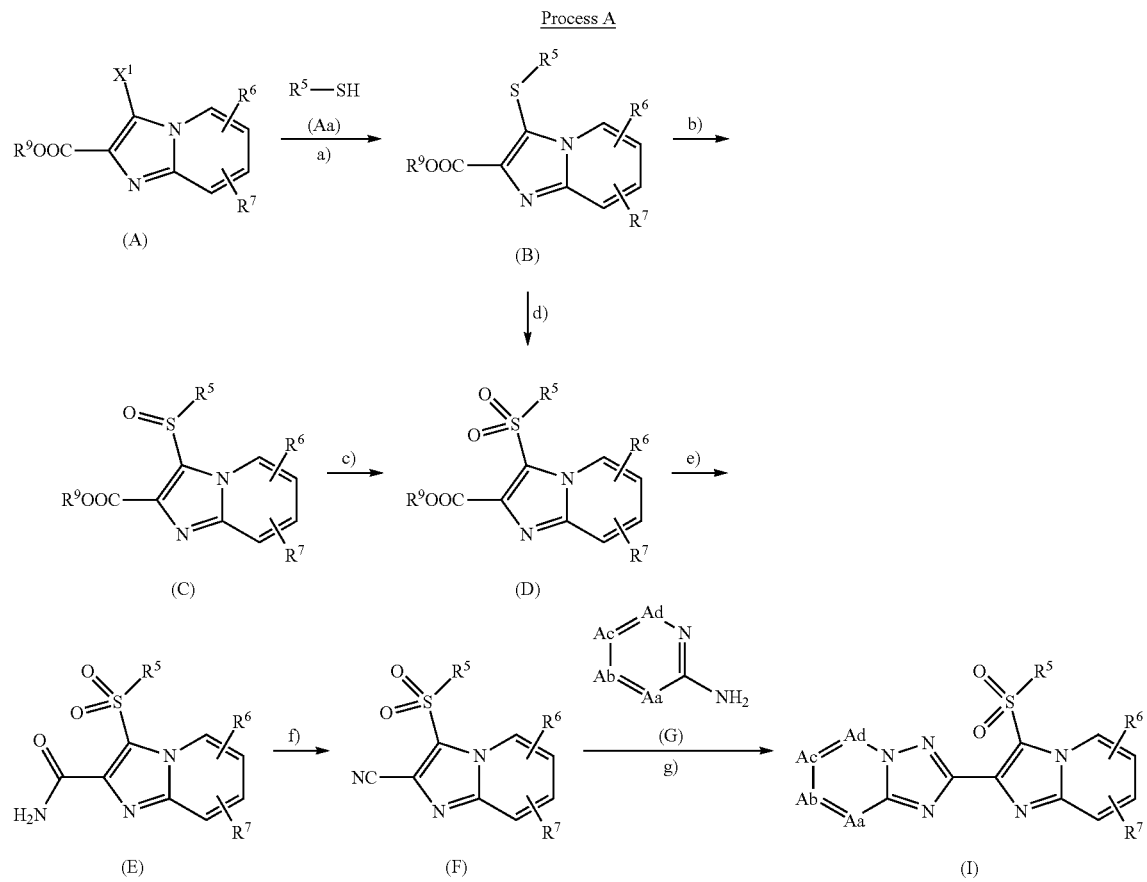

wher Aa, Ab, Ac, Ad, $R^5$, $R^6$ and $R^7$ are defined according to any of Configurations 1 to 6 and where Aa, Ab, Ac, Ad do not represent nitrogen. Furthermore, $R^9$ represents ($C_1$-$C_6$)-alkyl, preferably methyl or ethyl and $X^1$ represents halogen.

Step a)

The compounds of formula (B) can be prepared by reacting the compounds of formula (A) with the compounds of formula (Aa) in the presence of a base.

Mercaptan derivatives of formula (Aa), for example methyl mercaptan, ethyl mercaptan or isopropyl mercaptan, are either commercially available or can be prepared by known methods, for example analogously to the processes described in US2006/25633, US2006/111591, U.S. Pat. No. 2,820,062, Chemical Communications, 13 (2000), 1163-1164 or Journal of the American Chemical Society, 44 (1922), p. 1329.

The conversion to the compound of formula (B) can be carried out neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane, tert-butyl methyl ether; nitriles, for example acetonitrile or propionitrile; aromatic hydrocarbons, for example toluene or xylene; aprotic polar solvents, for example N,N-dimethylformamide, N-methylpyrrolidone or dimethyl sulfoxide.

Examples of suitable bases are inorganic bases from the group consisting of acetates, phosphates and carbonates of alkali metals or alkaline earth metals. Preference is given here to caesium carbonate, sodium carbonate and potassium carbonate. Further suitable bases are alkali metal hydrides, for example sodium hydride.

The reaction can be carried out under reduced pressure, at atmospheric pressure or under elevated pressure, and at temperatures of 0° C. to 200° C.

In the reaction described, $X^1$ is preferably a fluorine, bromine or chlorine atom.

Step b)

The compounds of formula (C) can be prepared by oxidizing the compounds of formula (B). The oxidation is generally carried out in a solvent selected from customary solvents which are inert under the prevailing reaction conditions. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water.

Examples of suitable oxidizing agents are hydrogen peroxide, meta-chloroperbenzoic acid or sodium periodate.

The reaction can be carried out under reduced pressure, at atmospheric pressure or under elevated pressure, and at temperatures from −20° C. to 120° C.

Step c)

The compounds of formula (D) can be prepared by oxidizing the compounds of formula (C). The oxidation is generally carried out in a solvent. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water.

Examples of suitable oxidizing agents are hydrogen peroxide and meta-chloroperbenzoic acid.

The reaction can be carried out under reduced pressure, at atmospheric pressure or under elevated pressure, and at temperatures from −20° C. to 120° C.

Step d)

The compounds of formula (D) can also be prepared in a one-step process by oxidizing the compounds of formula (B). The oxidation is generally carried out in a solvent. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water.

Examples of suitable oxidizing agents are hydrogen peroxide and meta-chloroperbenzoic acid.

The reaction can be carried out under reduced pressure, at atmospheric pressure or under elevated pressure, and at temperatures of −20° C. to 120° C.

Step e)

Compounds of formula (E) can be prepared analogously to the process described in WO2010/65760 or WO2016/133838 by reacting compounds of formula (D) with an ammonia source. In most cases, the ammonia source used is ammonium hydroxide or methanolic ammonia solution.

The reaction of the compounds of formula (D) with the ammonia source is preferably carried out in a solvent selected from customary solvents which are inert under the prevailing reaction conditions. Preference is given to ethers such as dioxane or tetrahydrofuran or to alcohols such as methanol.

The reaction can be carried out under reduced pressure, at atmospheric pressure or under elevated pressure. Preferably, the reaction is carried out at atmospheric pressure and temperatures from 20 to 70° C.

Step f)

Compounds of formula (F) can be prepared analogously to the process described in WO2010/65760 or EP2740730 by reacting compounds of formula (E) with a dehydrating agent. In most cases, the dehydrating agent used is phosphoryl chloride or trifluoroacetic anhydride.

The reaction of the compounds of formula (E) with the dehydrating agent can be carried out neat or in a solvent. The reaction is optionally carried out in a solvent selected from customary solvents which are inert under the prevailing reaction conditions. Preference is given to ethers, for example dioxane or tetrahydrofuran.

The reaction can be carried out under reduced pressure, at atmospheric pressure or under elevated pressure. Preferably, the reaction is carried out at atmospheric pressure and temperatures from 20 to 120° C.

Step g)

Compounds of formula (I) can be prepared analogously to the process described in WO2013/41472 or *J. Am. Chem Soc.* 2009, 131, 15080-15081 by reacting compounds of formula (F) with compounds of formula (G) in the presence of a copper source. In most cases, the copper source used is CuBr or Cu(OAc)$_2$.

The reaction of the compounds of formula (F) with the compound of formula (G) and the copper source is preferably carried out in a solvent selected from conventional solvents which are inert under the prevailing reaction conditions. Aromatic hydrocarbons such as, for example, 1,2-dichlorobenzene or toluene are preferred.

The reaction can be carried out under reduced pressure, at atmospheric pressure or under elevated pressure. Preferably, the reaction is carried out at atmospheric pressure and temperatures from 50 to 150° C.

Process B

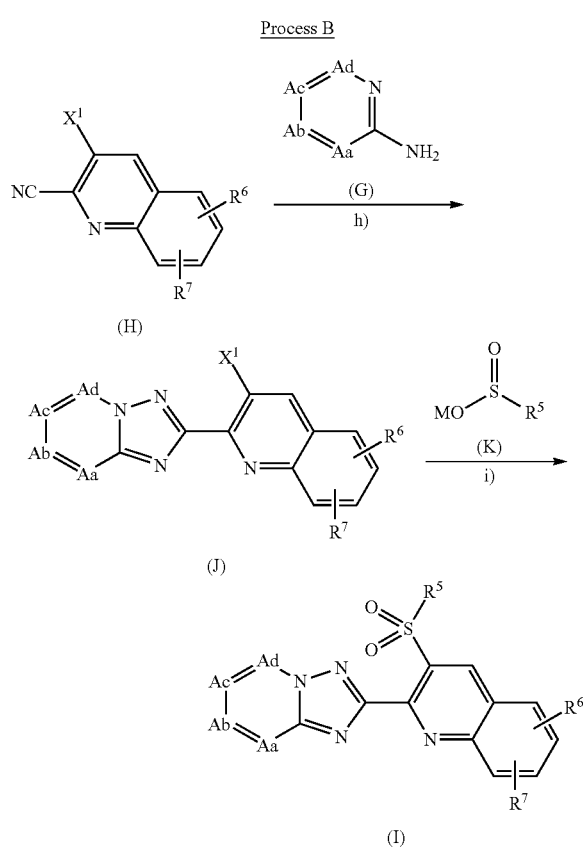

Where Aa, Ab, Ac, Ad, $R^5$, $R^6$ and $R^7$ are defined according to any of Configurations 1 to 6 and where Aa, Ab, Ac, Ad do not represent nitrogen. Furthermore, $X^1$ represents halogen and M represents lithium, sodium or potassium.

Step h)

Compounds of formula (J) can be prepared analogously to the process described in WO2013/41472 or *J. Am. Chem. Soc.* 2009, 131, 15080-15081 by reacting compounds of formula (F) with compounds of formula (G) in the presence of a copper source.

Compounds of formula (H) are commercially available or can be prepared using the transformations described in process A, steps e) and f).

In most cases, the copper source used is CuBr or Cu(OAc)$_2$.

The reaction of the compound of formula (F) with the compound of formula (G) and the copper source is preferably carried out in a solvent selected from conventional solvents which are inert under the prevailing reaction conditions. Aromatic hydrocarbons such as, for example, 1,2-dichlorobenzene or toluene are preferred.

The reaction can be carried out under reduced pressure, at atmospheric pressure or under elevated pressure. Preferably, the reaction is carried out at atmospheric pressure and temperatures from 50 to 150° C.

Step i)

Compounds of formula (I) can be prepared, for example analogously to the processes described in Journal of Organic Chemistry 2005, 70, 2696-2700, by halogen/sulfone exchange starting with compounds of formula (J) using a compound of formula (K) in the presence of a copper source.

Compounds of formula (K) are either commercially available or can be prepared by known methods, for example analogously to the processes described in Tetrahedron Letters, 2014, 55, 3851-3855.

The reaction of the compound of formula (J) with the compound of formula (K) and the copper source is generally carried out in a solvent. Preference is given to using polar aprotic solvents, for example dimethyl sulfoxide and N,N-dimethylformamide.

In most cases, the copper source used is CuBr, CuI or Cu(OAc)$_2$.

Examples of suitable sulfur reagents are sodium salts of sulfinic acids.

The reaction can be carried out under reduced pressure, at atmospheric pressure or under elevated pressure, and at temperatures of 20° C. to 200° C.

Process C

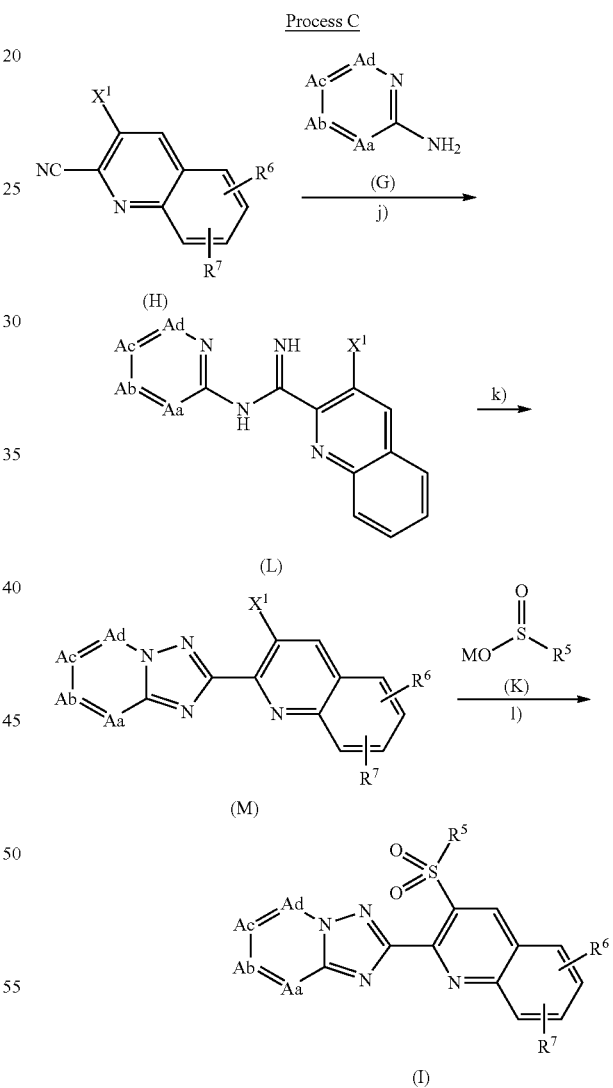

Where Aa, Ab, Ac, Ad, $R^5$, $R^6$ and $R^7$ are defined according to any of Configurations 1 to 6, $X^1$ represents halogen and M represents lithium, sodium or potassium.

Step j)

The compounds of formula (L) can be prepared by reacting the compounds of formula (H) with the compounds of formula (G) in the presence of a base.

Compounds of formula (H) are commercially available or can be prepared using the transformations described in process A, steps e) and f).

The conversion to the compound of formula (B) can be carried out neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane, tert-butyl methyl ether; nitriles, for example acetonitrile or propionitrile; aromatic hydrocarbons, for example toluene or xylene; aprotic polar solvents, for example N,N-dimethylformamide, N-methylpyrrolidone or dimethyl sulfoxide.

Examples of suitable bases are alkali metal hydrides such as, for example, sodium hydride, alkali metal salts of hexamethyldisilazane, for example sodium hexamethyldisilazide, alkoxides such as, for example, potassium tert-butoxide, or lithium diisopropylamide.

The reaction can be carried out under reduced pressure, at atmospheric pressure or under elevated pressure, and at temperatures of 0° C. to 200° C.

In the reaction described, $X^1$ is preferably a fluorine, bromine or chlorine atom.

Step k)

Compounds of formula (M) can be prepared analogously to the process described in *J. Org. Chem.* 2015, 80, 7319-7225 or *J. Org. Chem.* 2014, 79, 4687-4693 by reacting compounds of formula (L) in the presence of an oxidizing agent.

In most cases, the oxidizing agent used is $I_2$ or (diacetoxyiodo)benzene.

The reaction of the compound of formula (L) with the oxidizing agent is preferably carried out in a solvent selected from conventional solvents which are inert under the prevailing reaction conditions. Preference is given to nitriles such as acetonitrile or propionitrile; aromatic hydrocarbons such as toluene or xylene; aprotic polar solvents such as N,N-dimethylformamide, N-methylpyrrolidone, dimethyl sulfoxide or ethyl acetate, halogenated hydrocarbons such as dichloromethane or dichloroethane.

The reaction can be carried out under reduced pressure, at atmospheric pressure or under elevated pressure. Preferably, the reaction is carried out at atmospheric pressure and temperatures from −20 to 100° C.

Step l)

Compounds of formula (I) where n represents 2 can be prepared in a one-step procedure, for example in analogy to the process described in Journal of Organic Chemistry 2005, 70, 2696-2700 by a halogen-sulfone exchange with a compound of formula (K) proceeding from compounds of formula (M). The exchange is generally carried out in a solvent. Preference is given to using polar aprotic solvents, for example dimethyl sulfoxide and N,N-dimethylformamide.

Compounds of formula (K) are either commercially available or can be prepared by known methods, for example analogously to the processes described in Organic Synthesis 1977, 57, 88-92; Tetrahedron Letters 1979, 9, 821-824 and Bulletin de la Societe Chimique de France 1958, 4, 447-450.

Examples of suitable sulfur reagents are sodium salts of sulfinic acid.

The reaction can be carried out under reduced pressure, at atmospheric pressure or under elevated pressure, and at temperatures of −20° C. to 120° C.

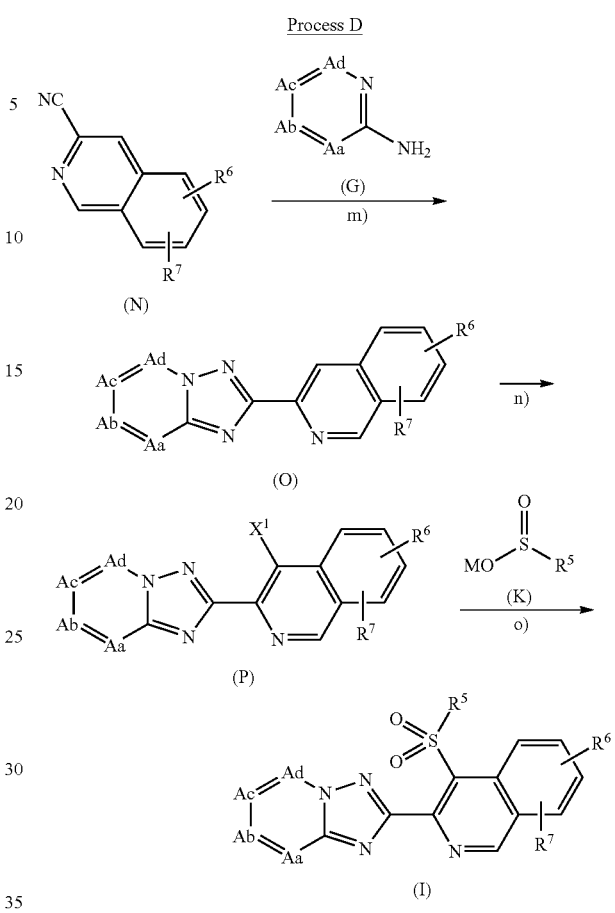

Process D

Where Aa, Ab, Ac, Ad, $R^5$, $R^6$ and $R^7$ are defined according to any of Configurations 1 to 6 and where Aa, Ab, Ac, Ad do not represent nitrogen. Furthermore, $X^1$ represents halogen and M represents lithium, sodium or potassium.

Step m)

Compounds of formula (O) can be prepared analogously to the process described in WO2013/41472 or *J. Am. Chem Soc.* 2009, 131, 15080-15081 by reacting compounds of formula (N) with compounds of formula (G) in the presence of a copper source.

Compounds of formula (N) are commercially available or can be prepared using the transformations described in process A, steps e) and f).

In most cases, the copper source used is CuBr or Cu(OAc)$_2$.

The reaction of the compound of formula (N) with the compound of formula (G) and the copper source is preferably carried out in a solvent selected from conventional solvents which are inert under the prevailing reaction conditions. Aromatic hydrocarbons such as, for example, 1,2-dichlorobenzene or toluene are preferred.

The reaction can be carried out under reduced pressure, at atmospheric pressure or under elevated pressure. Preferably, the reaction is carried out at atmospheric pressure and temperatures from 50 to 150° C.

Step n)

Conversion of the compound of formula (0) into compounds of formula (P) can be carried out under standard conditions in the presence of a suitable halogenating agent. Suitable halogenating agents are, for example, N-bromosuccinimide or N-chlorosuccinimide The compounds of formula (XVI) can then be prepared by reacting the compounds of formula (XXVIII) with the compounds of formula (XXIV) in the presence of a base.

Step o)

Compounds of formula (I) where n represents 2 can be prepared in a one-step procedure, for example in analogy to the process described in Journal of Organic Chemistry 2005, 70, 2696-2700 by a halogen-sulfone exchange with a compound of formula (K) proceeding from compounds of formula (M). The exchange is generally carried out in a solvent. Preference is given to using polar aprotic solvents, for example dimethyl sulfoxide and N,N-dimethylformamide.

Compounds of formula (K) are either commercially available or can be prepared by known methods, for example analogously to the processes described in Organic Synthesis 1977, 57, 88-92; Tetrahedron Letters 1979, 9, 821-824 and Bulletin de la Societe Chimique de France 1958, 4, 447-450.

Examples of suitable sulfur reagents are sodium salts of sulfinic acid.

The reaction can be carried out under reduced pressure, at atmospheric pressure or under elevated pressure, and at temperatures of −20° C. to 120° C.

Methods and Uses

The invention also relates to methods for controlling animal pests, in which compounds of formula (I) are allowed to act on animal pests and/or their habitat. The control of the animal pests is preferably conducted in agriculture and forestry, and in material protection. This preferably excludes methods for surgical or therapeutic treatment of the human or animal body and diagnostic methods carried out on the human or animal body.

The invention further relates to the use of the compounds of formula (I) as pesticides, especially crop protection agents.

In the context of the present application, the term "pesticides" in each case also always encompasses the term "crop protection agents".

The compounds of formula (I), given good plant tolerance, favourable endotherm toxicity and good environmental compatibility, are suitable for protecting plants and plant organs against biotic and abiotic stress factors, for increasing harvest yields, for improving the quality of the harvested material and for controlling animal pests, especially insects, arachnids, helminths, especially nematodes and molluscs, which are encountered in agriculture, in horticulture, in animal husbandry, in aquatic cultures, in forests, in gardens and leisure facilities, in the protection of stored products and of materials, and in the hygiene sector.

In the context of the present patent application, the term "hygiene" should be understood to mean any and all measures, provisions and procedures which have the aim of preventing diseases, especially infection diseases, and which serve to protect the health of humans and animals and/or protect the environment and/or maintain cleanliness. According to the invention, this especially includes measures for cleaning, disinfection and sterilization, for example of textiles or hard surfaces, especially surfaces made of glass, wood, cement, porcelain, ceramic, plastic or else metal(s), in order to ensure that these are free of hygiene pests and/or their secretions. The scope of protection of the invention in this regard preferably excludes surgical or therapeutic treatment procedures to be applied to the human body or the bodies of animals, and diagnostic procedures which are conducted on the human body or the bodies of animals.

The term "hygiene sector" covers all areas, technical fields and industrial applications in which these hygiene measures, provisions and procedures are important, for example with regard to hygiene in kitchens, bakeries, airports, bathrooms, swimming pools, department stores, hotels, hospitals, stables, animal keeping, etc.

The term "hygiene pest" should therefore be understood to mean one or more animal pests whose presence in the hygiene sector is problematic, especially for reasons of health. A main aim is therefore that of avoiding, or limiting to a minimum degree, the presence of hygiene pests and/or the exposure to these in the hygiene sector. This can especially be achieved through the use of a pesticide which can be used both for prevention of infestation and for prevention of an existing infestation. It is also possible to use formulations which prevent or reduce exposure to pests. Hygiene pests include, for example, the organisms mentioned below.

The term "hygiene protection" thus covers all acts by which these hygiene measures, provisions and procedures are maintained and/or improved.

The compounds of formula (I) can preferably be used as pesticides. They are active against normally sensitive and resistant species and also against all or specific stages of development. The abovementioned pests include:

pests from the phylum of the Arthropoda, especially from the class of the Arachnida e.g. *Acarus* spp., e.g. *Acarus siro, Aceria kuko, Aceria sheldoni, Aculops* spp., *Aculus* spp., e.g. *Aculus fockeui, Aculus schlechtendali, Amblyomma* spp., *Amphitetranychus viennensis, Argas* spp., *Boophilus* spp., *Brevipalpus* spp., e.g. *Brevipalpus phoenicis, Bryobia graminum, Bryobia praetiosa, Centruroides* spp., *Chorioptes* spp., *Dermanyssus gallinae, Dermatophagoides pteronyssinus, Dermatophagoides farinae, Dermacentor* spp., *Eotetranychus* spp., e.g. *Eotetranychus hicoriae, Epitrimerus pyri, Eutetranychus* spp., e.g. *Eutetranychus banksi, Eriophyes* spp., e.g. *Eriophyes pyri, Glycyphagus domesticus, Halotydeus destructor, Hemitarsonemus* spp., e.g. *Hemitarsonemus latus* (=*Polyphagotarsonemus latus*), *Hyalomma* spp., *Ixodes* spp., *Latrodectus* spp., *Loxosceles* spp., *Neutrombicula autumnalis, Nuphersa* spp., *Oligonychus* spp., e.g. *Oligonychus coffeae, Oligonychus coniferarum, Oligonychus ilicis, Oligonychus indicus, Oligonychus mangiferus, Oligonychus pratensis, Oligonychus punicae, Oligonychus yothersi, Ornithodorus* spp., *Ornithonyssus* spp., *Panonychus* spp., e.g. *Panonychus citri* (=*Metatetranychus citri*), *Panonychus ulmi* (=*Metatetranychus ulmi*), *Phyllocoptruta oleivora, Platytetranychus multidigituli, Polyphagotarsonemus latus, Psoroptes* spp., *Rhipicephalus* spp., *Rhizoglyphus* spp., *Sarcoptes* spp., *Scorpio maurus, Steneotarsonemus* spp., *Steneotarsonemus spinki, Tarsonemus* spp., e.g. *Tarsonemus confusus, Tarsonemus pallidus, Tetranychus* spp., e.g. *Tetranychus canadensis, Tetranychus cinnabarinus, Tetranychus turkestani, Tetranychus urticae, Trombicula alfreddugesi, Vaejovis* spp., *Vasates lycopersici;* from the class of the Chilopoda, for example *Geophilus* spp., *Scutigera* spp.;

from the order or the class of the Collembola, for example *Onychiurus armatus, Sminthurus viridis;* from the class of the Diplopoda, for example *Blaniulus guttulatus;* from the class of the Insecta, for example from the order of the Blattodea, e.g. *Blatta orientalis, Blattella asahinai, Blattella germanica, Leucophaea maderae, Loboptera decipiens, Neostylopyga rhombifolia, Panchlora* spp., *Parcoblatta* spp., *Periplaneta* spp., e.g. *Periplaneta americana, Periplaneta australasiae, Pycnoscelus surinamensis, Supella longipalpa;* from the order of the Coleoptera e.g. *Acalymma vittatum, Acanthoscelides obtectus, Adoretus* spp., *Aethina tumida,*

*Agelastica alni, Agrilus* spp., e.g. *Agrilus planipennis, Agrilus coxalis, Agrilus bilineatus, Agrilus anxius, Agriotes* spp., e.g. *Agriotes linneatus, Agriotes mancus, Alphitobius diaperinus, Amphimallon solstitialis, Anobium punctatum, Anoplophora* spp., e.g. *Anoplophora glabripennis, Anthonomus* spp., e.g. *Anthonomus grandis, Anthrenus* spp., *Apion* spp., *Apogonia* spp., *Atomaria* spp., e.g. *Atomaria linearis, Attagenus* spp., Bans *caerulescens, Bruchidius obtectus, Bruchus* spp., e.g. *Bruchus pisorum, Bruchus rufimanus, Cassida* spp., *Cerotoma trifurcata, Ceutorrhynchus* spp., e.g. *Ceutorrhynchus assimilis, Ceutorrhynchus quadridens, Ceutorrhynchus rapae, Chaetocnema* spp., e.g. *Chaetocnema confinis, Chaetocnema denticulata, Chaetocnema ectypa, Cleonus mendicus, Conoderus* spp., *Cosmopolites* spp., e.g. *Cosmopolites sordidus, Costelytra zealandica, Ctenicera* spp., *Curculio* spp., e.g. *Curculio caryae, Curculio caryatrypes, Curculio obtusus, Curculio sayi, Cryptolestes ferrugineus, Cryptolestes pusillus, Cryptorhynchus lapathi, Cryptorhynchus mangiferae, Cylindrocopturus* spp., *Cylindrocopturus adspersus, Cylindrocopturus furnissi, Dendroctonus* spp., e.g. *Dendroctonus ponderosae, Dermestes* spp., *Diabrotica* spp., e.g. *Diabrotica balteata, Diabrotica barberi, Diabrotica undecimpunctata howardi, Diabrotica undecimpunctata undecimpunctata, Diabrotica virgifera virgifera, Diabrotica virgifera zeae, Dichocrocis* spp., *Dicladispa armigera, Diloboderus* spp., *Epicaerus* spp., *Epilachna* spp., e.g. *Epilachna borealis, Epilachna varivestis, Epitrix* spp., e.g. *Epitrix cucumeris, Epitrix fuscula, Epitrix hirtipennis, Epitrix subcrinita, Epitrix tuberis, Faustinus* spp., *Gibbium psylloides, Gnathocerus cornutus, Hellula undalis, Heteronychus arator, Heteronyx* spp., *Hylamorpha elegans, Hylotrupes bajulus, Hypera postica, Hypomeces squamosus, Hypothenemus* spp., e.g. *Hypothenemus hampei, Hypothenemus obscurus, Hypothenemus pubescens, Lachnosterna consanguinea, Lasioderma serricorne, Latheticus oryzae, Lathridius* spp., *Lema* spp., *Leptinotarsa decemlineata, Leucoptera* spp., e.g. *Leucoptera coffeella, Limonius ectypus, Lissorhoptrus oryzophilus, Listronotus* (=*Hyperodes*) spp., *Lixus* spp., *Luperodes* spp., *Luperomorpha xanthodera, Lyctus* spp., *Megacyllene* spp., e.g. *Megacyllene robiniae, Megascelis* spp., *Melanotus* spp., e.g. *Melanotus longulus oregonensis, Meligethes aeneus, Melolontha* spp., e.g. *Melolontha melolontha, Migdolus* spp., *Monochamus* spp., *Naupactus xanthographus, Necrobia* spp., *Neogalerucella* spp., *Niptus hololeucus, Oryctes rhinoceros, Oryzaephilus surinamensis, Oryzaphagus oryzae, Otiorhynchus* spp., e.g. *Otiorhynchus cribricollis, Otiorhynchus ligustici, Otiorhynchus ovatus, Otiorhynchus rugosostriarus, Otiorhynchus sulcatus, Oulema* spp., e.g. *Oulema melanopus, Oulema oryzae, Oxycetonia jucunda, Phaedon cochleariae, Phyllophaga* spp., *Phyllophaga helleri, Phyllotreta* spp., e.g. *Phyllotreta armoraciae, Phyllotreta pusilla, Phyllotreta ramosa, Phyllotreta striolata, Popillia japonica, Premnotrypes* spp., *Prostephanus truncatus, Psylliodes* spp., e.g. *Psylliodes affinis, Psylliodes chrysocephala, Psylliodes punctulata, Ptinus* spp., *Rhizobius ventralis, Rhizopertha dominica, Rhynchophorus* spp., *Rhynchophorus ferrugineus, Rhynchophorus palmarum, Scolytus* spp., e.g. *Scolytus multistriatus, Sinoxylon perforans, Sitophilus* spp., e.g. *Sitophilus granarius, Sitophilus linearis, Sitophilus oryzae, Sitophilus zeamais, Sphenophorus* spp., *Stegobium paniceum, Sternechus* spp., e.g. *Sternechus paludatus, Symphyletes* spp., *Tanymecus* spp., e.g. *Tanymecus dilaticollis, Tanymecus indicus, Tanymecus palliatus, Tenebrio molitor, Tenebrioides mauretanicus, Tribolium* spp., e.g. *Tribolium audax, Tribolium castaneum, Tribolium confusum, Trogoderma* spp., *Tychius* spp., *Xylotrechus* spp., *Zabrus* spp., e.g. *Zabrus tenebrioides;* from the order of the Dermaptera, for example Anisolabis maritime, *Forficula auricularia, Labidura riparia;* from the order of the Diptera e.g. *Aedes* spp., e.g. *Aedes aegypti, Aedes albopictus, Aedes sticticus, Aedes vexans, Agromyza* spp., e.g. *Agromyza frontella, Agromyza parvicornis, Anastrepha* spp., *Anopheles* spp., e.g. *Anopheles quadrimaculatus, Anopheles gambiae, Asphondylia* spp., *Bactrocera* spp., e.g. *Bactrocera cucurbitae, Bactrocera dorsalis, Bactrocera oleae, Bibio hortulanus, Calliphora erythrocephala, Calliphora vicina, Ceratitis capitata, Chironomus* spp., *Chrysomya* spp., *Chrysops* spp., *Chrysozona pluvialis, Cochliomya* spp., *Contarinia* spp., e.g. *Contarinia johnsoni, Contarinia nasturtii, Contarinia pyrivora, Contarinia schulzi, Contarinia sorghicola, Contarinia tritici, Cordylobia anthropophaga, Cricotopus sylvestris, Culex* spp., e.g. *Culex pipiens, Culex quinquefasciatus, Culicoides* spp., *Culiseta* spp., *Cuterebra* spp., *Dacus oleae, Dasineura* spp., e.g. *Dasineura brassicae, Delia* spp., e.g. *Delia antiqua, Delia coarctata, Delia florilega, Delia platura, Delia radicum, Dermatobia hominis, Drosophila* spp., e.g. *Drosphila melanogaster, Drosophila suzukii, Echinocnemus* spp., *Euleia heraclei, Fannia* spp., *Gasterophilus* spp., *Glossina* spp., *Haematopota* spp., *Hydrellia* spp., *Hydrellia griseola, Hylemya* spp., *Hippobosca* spp., *Hypoderma* spp., *Liriomyza* spp., e.g. *Liriomyza brassicae, Liriomyza huidobrensis, Liriomyza sativae, Lucilia* spp., e.g. *Lucilia cuprina, Lutzomyia* spp., *Mansonia* spp., *Musca* spp., e.g. *Musca domestica, Musca domestica vicina, Oestrus* spp., *Oscinella frit, Paratanytarsus* spp., *Paralauterborniella subcincta, Pegomya oder Pegomyia* spp., e.g. *Pegomya betae, Pegomya hyoscyami, Pegomya rubivora, Phlebotomus* spp., *Phorbia* spp., *Phormia* spp., *Piophila casei, Platyparea poeciloptera, Prodiplosis* spp., *Psila rosae, Rhagoletis* spp., e.g. *Rhagoletis cingulata, Rhagoletis completa, Rhagoletis fausta, Rhagoletis indifferens, Rhagoletis mendax, Rhagoletis pomonella, Sarcophaga* spp., *Simulium* spp., e.g. *Simulium meridionale, Stomoxys* spp., *Tabanus* spp., *Tetanops* spp., *Tipula* spp., e.g. *Tipula paludosa, Tipula simplex, Toxotrypana curvicauda;* from the order of the Hemiptera e.g. *Acizzia acaciaebaileyanae, Acizzia dodonaeae, Acizzia uncatoides, Acrida turrita, Acyrthosipon* spp., e.g. *Acyrthosiphon pisum, Acrogonia* spp., *Aeneolamia* spp., *Agonoscena* spp., *Aleurocanthus* spp., *Aleyrodes proletella, Aleurolobus barodensis, Aleurothrixus floccosus, Allocaridara malayensis, Amrasca* spp., e.g. *Amrasca bigutulla, Amrasca devastans, Anuraphis cardui, Aonidiella* spp., e.g. *Aonidiella aurantii, Aonidiella citrina, Aonidiella inornata, Aphanostigma pini, Aphis* spp., e.g. *Aphis citricola, Aphis craccivora, Aphis fabae, Aphis forbesi, Aphis glycines, Aphis gossypii, Aphis hederae, Aphis illinoisensis, Aphis middletoni, Aphis nasturtii, Aphis nerii, Aphis pomi, Aphis spiraecola, Aphis viburniphila, Arboridia apicalis, Arytainilla* spp., *Aspidiella* spp., *Aspidiotus* spp., e.g. *Aspidiotus nerii, Atanus* spp., *Aulacorthum solani, Bemisia tabaci, Blastopsylla occidentalis, Boreioglycaspis melaleucae, Brachycaudus helichrysi, Brachycolus* spp., *Brevicoryne brassicae, Cacopsylla* spp., e.g. *Cacopsylla pyricola, Calligypona marginata, Capulinia* spp., *Carneocephala fulgida, Ceratovacuna lanigera, Cercopidae, Ceroplastes* spp., *Chaetosiphon fragaefolii, Chionaspis tegalensis, Chlorita onukii, Chondracris rosea, Chromaphis juglandicola, Chrysomphalus aonidum, Chrysomphalus ficus, Cicadulina mbila, Coccomytilus halli, Coccus* spp., e.g. *Coccus hesperidum, Coccus longulus, Coccus pseudomagnoliarum, Coccus viridis, Cryptomyzus*

*ribis, Cryptoneossa* spp., *Ctenarytaina* spp., *Dalbulus* spp., *Dialeurodes chittendeni, Dialeurodes citri, Diaphorina citri, Diaspis* spp., *Diuraphis* spp., *Doralis* spp., *Drosicha* spp., *Dysaphis* spp., e.g. *Dysaphis apiifolia, Dysaphis plantaginea, Dysaphis tulipae, Dysmicoccus* spp., *Empoasca* spp., e.g. *Empoasca abrupta, Empoasca fabae, Empoasca maligna, Empoasca solana, Empoasca stevensi, Eriosoma* spp., e.g. *Eriosoma americanum, Eriosoma lanigerum, Eriosoma pyricola, Erythroneura* spp., *Eucalyptolyma* spp., *Euphyllura* spp., *Euscelis bilobatus, Ferrisia* spp., *Fiorinia* spp., *Furcaspis oceanica, Geococcus coffeae, Glycaspis* spp., *Heteropsylla cubana, Heteropsylla spinulosa, Homalodisca coagulata, Hyalopterus arundinis, Hyalopterus pruni, Icerya* spp., e.g. *Icerya purchasi, Idiocerus* spp., *Idioscopus* spp., *Laodelphax striatellus, Lecanium* spp., e.g. *Lecanium corni (=Parthenolecanium corni), Lepidosaphes* spp., e.g. *Lepidosaphes ulmi, Lipaphis erysimi, Lopholeucaspis japonica, Lycorma delicatula, Macrosiphum* spp., e.g. *Macrosiphum euphorbiae, Macrosiphum lilii, Macrosiphum rosae, Macrosteles facifrons, Mahanarva* spp., *Melanaphis sacchari, Metcalfiella* spp., *Metcalfa pruinosa, Metopolophium dirhodum, Monellia costalis, Monelliopsis pecanis, Myzus* spp., e.g. *Myzus ascalonicus, Myzus cerasi, Myzus ligustri, Myzus ornatus, Myzus persicae, Myzus nicotianae, Nasonovia ribisnigri, Neomaskellia* spp., *Nephotettix* spp., e.g. *Nephotettix cincticeps, Nephotettix nigropictus, Nettigoniclla spectra, Nilaparvata lugens, Oncometopia* spp., *Orthezia praelonga, Oxya chinensis, Pachypsylla* spp., *Parabemisia myricae, Paratrioza* spp., e.g. *Paratrioza cockerelli, Parlatoria* spp., *Pemphigus* spp., e.g. *Pemphigus bursarius, Pemphigus populivenae, Peregrinus maidis, Perkinsiella* spp., *Phenacoccus* spp., e.g. *Phenacoccus madeirensis, Phloeomyzus passerinii, Phorodon humuli, Phylloxera* spp., e.g. *Phylloxera devastatrix, Phylloxera notabilis, Pinnaspis aspidistrae, Planococcus* spp., e.g. *Planococcus citri, Prosopidopsylla flava, Protopulvinaria pyriformis, Pseudaulacaspis pentagona, Pseudococcus* spp., e.g. *Pseudococcus calceolariae, Pseudococcus comstocki, Pseudococcus longispinus, Pseudococcus maritimus, Pseudococcus viburni, Psyllopsis* spp., *Psylla* spp., e.g. *Psylla buxi, Psylla mali, Psylla pyri, Pteromalus* spp., *Pulvinaria* spp., *Pyrilla* spp., *Quadraspidiotus* spp., e.g. *Quadraspidiotus juglansregiae, Quadraspidiotus ostreaeformis, Quadraspidiotus perniciosus, Quesada gigas, Rastrococcus* spp., *Rhopalosiphum* spp., e.g. *Rhopalosiphum maidis, Rhopalosiphum oxyacanthae, Rhopalosiphum padi, Rhopalosiphum rufiabdominale, Saissetia* spp., e.g. *Saissetia coffeae, Saissetia miranda, Saissetia neglecta, Saissetia oleae, Scaphoideus titanus, Schizaphis graminum, Selenaspidus articulatus, Sipha flava, Sitobion avenae, Sogata* spp., *Sogatella furcifera, Sogatodes* spp., *Stictocephala festina, Siphoninus phillyreae, Tenalaphara malayensis, Tetragonocephela* spp., *Tinocallis caryaefoliae, Tomaspis* spp., *Toxoptera* spp., e.g. *Toxoptera aurantii, Toxoptera citricidus, Trialeurodes vaporariorum, Trioza* spp., e.g. *Trioza diospyri, Typhlocyba* spp., *Unaspis* spp., *Viteus vitifolii, Zygina* spp.;

from the suborder of the Heteroptera e.g. *Aelia* spp., *Anasa tristis, Antestiopsis* spp., *Boisea* spp., *Blissus* spp., *Calocoris* spp., *Campylomma livida, Cavelerius* spp., *Cimex* spp., e.g. *Cimex adjunctus, Cimex hemipterus, Cimex lectularius, Cimex pilosellus, Collaria* spp., *Creontiades dilutus, Dasynus piperis, Dichelops furcatus, Diconocoris hewetti, Dysdercus* spp., *Euschistus* spp., e.g. *Euschistus heros, Euschistus servus, Euschistus tristigmus, Euschistus variolarius, Eurydema* spp., *Eurygaster* spp., *Halyomorpha halys, Heliopeltis* spp., *Horcias nobilellus, Leptocorisa* spp., *Leptocorisa varicornis, Leptoglossus occidentalis, Leptoglossus phyllopus, Lygocoris* spp., e.g. *Lygocoris pabulinus, Lygus* spp., e.g. *Lygus elisus, Lygus hesperus, Lygus lineolaris, Macropes excavatus, Megacopta cribraria, Miridae, Monalonion atratum, Nezara* spp., e.g. *Nezara viridula, Nysius* spp., *Oebalus* spp., *Pentomidae, Piesma quadrata, Piezodorus* spp., e.g. *Piezodorus guildinii, Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.;

from the order of the Hymenoptera e.g. *Acromyrmex* spp., *Athalia* spp., e.g. *Athalia rosae, Atta* spp., *Camponotus* spp., *Dolichovespula* spp., *Diprion* spp., e.g. *Diprion similis, Hoplocampa* spp., e.g. *Hoplocampa cookei, Hoplocampa testudinea, Lasius* spp., *Linepithema (Iridiomyrmex) humile, Monomorium pharaonis, Paratrechina* spp., *Paravespula* spp., *Plagiolepis* spp., *Sirex* spp., e.g. *Sirex noctilio, Solenopsis invicta, Tapinoma* spp., *Technomyrmex albipes, Urocerus* spp., *Vespa* spp., e.g. *Vespa crabro, Wasmannia auropunctata, Xeris* spp.;

from the order of the Isopoda e.g. *Armadillidium vulgare, Oniscus asellus, Porcellio scaber;* from the order of the Isoptera e.g. *Coptotermes* spp., e.g. *Coptotermes formosanus, Cornitermes cumulans, Cryptotermes* spp., *Incisitermes* spp., *Kalotermes* spp., *Microtermes obesi, Nasutitermis* spp., *Odontotermes* spp., *Porotermes* spp., *Reticulitermes* spp., e.g. *Reticulitermes flavipes, Reticulitermes hesperus;* from the order of the Lepidoptera e.g. *Achroia grisella, Acronicta major, Adoxophyes* spp., e.g. *Adoxophyes orana, Aedia leucomelas, Agrotis* spp., e.g. *Agrotis segetum, Agrotis ipsilon, Alabama* spp., e.g. *Alabama argillacea, Amyelois transitella, Anarsia* spp., *Anticarsia* spp., e.g. *Anticarsia gemmatalis, Argyroploce* spp., *Autographa* spp., *Barathra brassicae, Blastodacna atra, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Cheimatobia brumata, Chilo* spp., e.g. *Chilo plejadellus, Chilo suppressalis, Choreutis pariana, Choristoneura* spp., *Chrysodeixis chalcites, Clysia ambiguella, Cnaphalocerus* spp., *Cnaphalocrocis medinalis, Cnephasia* spp., *Conopomorpha* spp., *Conotrachelus* spp., *Copitarsia* spp., *Cydia* spp., e.g. *Cydia nigricana, Cydia pomonella, Dalaca noctuides, Diaphania* spp., *Diparopsis* spp., *Diatraea saccharalis, Dioryctria* spp., e.g. *Dioryctria zimmermani, Earias* spp., *Ecdytolopha aurantium, Elasmopalpus lignosellus, Eldana saccharina, Ephestia* spp., e.g. *Ephestia elutella, Ephestia kuehniella, Epinotia* spp., *Epiphyas postvittana, Erannis* spp., *Erschoviella musculana, Etiella* spp., *Eudocima* spp., *Eulia* spp., *Eupoecilia ambiguella, Euproctis* spp., e.g. *Euproctis chrysorrhoea, Euxoa* spp., *Feltia* spp., *Galleria mellonella, Gracillaria* spp., *Grapholitha* spp., e.g. *Grapholita molesta, Grapholita prunivora, Hedylepta* spp., *Helicoverpa* spp., e.g. *Helicoverpa armigera, Helicoverpa zea, Heliothis* spp., e.g. *Heliothis virescens, Hofmannophila pseudospretella, Homoeosoma* spp., *Homona* spp., *Hyponomeuta padella, Kakivoria flavofasciata, Lampides* spp., *Laphygma* spp., *Laspeyresia molesta, Leucinodes orbonalis, Leucoptera* spp., e.g. *Leucoptera coffeella, Lithocolletis* spp., e.g. *Lithocolletis blancardella, Lithophane antennata, Lobesia* spp., e.g. *Lobesia botrana, Loxagrotis albicosta, Lymantria* spp., e.g. *Lymantria dispar, Lyonetia* spp., e.g. *Lyonetia clerkella, Malacosoma neustria, Maruca testulalis, Mamestra brassicae, Melanitis leda, Mocis* spp., *Monopis obviella, Mythimna separata, Nemapogon cloacellus, Nymphula* spp., *Oiketicus* spp., *Omphisa* spp., *Operophtera* spp., *Oria* spp.,

*Orthaga* spp., *Ostrinia* spp., e.g. *Ostrinia nubilalis, Panolis flammea, Parnara* spp., *Pectinophora* spp., e.g. *Pectinophora gossypiella, Perileucoptera* spp., *Phthorimaea* spp., e.g. *Phthorimaea operculella, Phyllocnistis citrella, Phyllonorycter* spp., *Phyllonorycter blancardella, Phyllonorycter crataegella, Pieris* spp., e.g. *Pieris rapae, Platynota stultana, Plodia interpunctella, Plusia* spp., *Plutella xylostella* (=*Plutella maculipennis*), *Podesia* spp., e.g. *Podesia syringae, Prays* spp., *Prodenia* spp., *Protoparce* spp., *Pseudaletia* spp., e.g. *Pseudaletia unipuncta, Pseudoplusia includens, Pyrausta nubilalis, Rachiplusia nu, Schoenobius* spp., e.g. *Schoenobius bipunctifer, Scirpophaga* spp., e.g. *Scirpophaga innotata, Scotia segetum, Sesamia* spp., e.g. *Sesamia inferens, Sparganothis* spp., *Spodoptera* spp., e.g. *Spodoptera eradiana, Spodoptera exigua, Spodoptera frugiperda, Spodoptera praefica, Stathmopoda* spp., *Stenoma* spp., *Stomopteryx subsecivella, Synanthedon* spp., *Tecia solanivora, Thaumetopoea* spp., *Thermesia gemmatalis, Tinea cloacella, Tinea pellionella, Tineola bisselliella, Tortrix* spp., *Trichophaga tapetzella, Trichoplusia* spp., e.g. *Trichoplusia ni, Tryporyza incertulas, Tuta absoluta, Virachola* spp.;

from the order of the Orthoptera or Saltatoria e.g. *Acheta domesticus, Dichroplus* spp., *Gryllotalpa* spp., e.g. *Gryllotalpa gryllotalpa, Hieroglyphus* spp., *Locusta* spp., e.g. *Locusta migratoria, Melanoplus* spp., e.g. *Melanoplus devastator, Paratlanticus ussuriensis, Schistocerca gregaria*;

from the order of the Phthiraptera e.g. *Damalinia* spp., *Haematopinus* spp., *Linognathus* spp., *Pediculus* spp., *Phylloxera vastatrix, Phthirus pubis, Trichodectes* spp.;

from the order of the Psocoptera, for example *Lepinotus* spp., *Liposcelis* spp.;

from the order of the Siphonaptera e.g. *Ceratophyllus* spp., *Ctenocephalides* spp., e.g. *Ctenocephalides canis, Ctenocephalides felis, Pulex irritans, Tunga penetrans, Xenopsylla cheopis*;

from the order of the Thysanoptera e.g. *Anaphothrips obscurus, Baliothrips biformis, Chaetanaphothrips leeuweni, Drepanothrips reuteri, Enneothrips flavens, Frankliniella* spp., e.g. *Frankliniella fusca, Frankliniella occidentalis, Frankliniella schultzei, Frankliniella tritici, Frankliniella vaccinii, Frankliniella williamsi, Haplothrips* spp., *Heliothrips* spp., *Hercinothrips femoralis, Kakothrips* spp., *Rhipiphorothrips cruentatus, Scirtothrips* spp., *Taeniothrips cardamomi, Thrips* spp., e.g. *Thrips palmi, Thrips tabaci*;

from the order of the Zygentoma (=Thysanura), for example *Ctenolepisma* spp., *Lepisma saccharina, Lepismodes inquilinus, Thermobia domestica*;

from the class of the Symphyla, for example *Scutigerella* spp., e.g. *Scutigerella immaculata*;

pests from the phylum of the Mollusca, for example from the class of the Bivalvia, e.g. *Dreissena* spp.;

and from the class of the Gastropoda e.g. *Anion* spp., e.g. *Anion ater rufus, Biomphalaria* spp., *Bulinus* spp., *Deroceras* spp., e.g. *Deroceras laeve, Galba* spp., *Lymnaea* spp., *Oncomelania* spp., *Pomacea* spp., *Succinea* spp.;

plant pests from the phylum of the Nematoda, i.e. phytoparasitic nematodes, in particular *Aglenchus* spp., e.g. *Aglenchus agricola, Anguina* spp., e.g. *Anguina tritici, Aphelenchoides* spp., e.g. *Aphelenchoides arachidis, Aphelenchoides fragariae, Belonolaimus* spp., e.g. *Belonolaimus gracilis, Belonolaimus longicaudatus, Belonolaimus nortoni, Bursaphelenchus* spp., e.g. *Bursaphelenchus cocophilus, Bursaphelenchus eremus, Bursaphelenchus xylophilus, Cacopaurus* spp., e.g. *Cacopaurus pestis, Criconemella* spp., e.g. *Criconemella curvata, Criconemella onoensis, Criconemella ornata, Criconemella rusium, Criconemella xenoplax* (=*Mesocriconema xenoplax*), *Criconemoides* spp., e.g. *Criconemoides ferniae, Criconemoides onoense, Criconemoides ornatum, Ditylenchus* spp., e.g. *Ditylenchus dipsaci, Dolichodorus* spp., *Globodera* spp., e.g. *Globodera pallida, Globodera rostochiensis, Helicotylenchus* spp., e.g. *Helicotylenchus dihystera, Hemicriconemoides* spp., *Hemicycliophora* spp., *Heterodera* spp., e.g. *Heterodera avenae, Heterodera glycines, Heterodera schachtii, Hirschmaniella* spp., *Hoplolaimus* spp., *Longidorus* spp., e.g. *Longidorus africanus, Meloidogyne* spp., e.g. *Meloidogyne chitwoodi, Meloidogyne fallax, Meloidogyne hapla, Meloidogyne incognita, Meloinema* spp., *Nacobbus* spp., *Neotylenchus* spp., *Paralongidorus* spp., *Paraphelenchus* spp., *Paratrichodorus* spp., e.g. *Paratrichodorus minor, Paratylenchus* spp., *Pratylenchus* spp., e.g. *Pratylenchus penetrans, Pseudohalenchus* spp., *Psilenchus* spp., *Punctodera* spp., *Quinisulcius* spp., *Radopholus* spp., e.g. *Radopholus citrophilus, Radopholus similis, Rotylenchulus* spp., *Rotylenchus* spp., *Scutellonema* spp., *Subanguina* spp., *Trichodorus* spp., e.g. *Trichodorus obtusus, Trichodorus primitivus, Tylenchorhynchus* spp., e.g. *Tylenchorhynchus annulatus, Tylenchulus* spp., e.g. *Tylenchulus semipenetrans, Xiphinema* spp., e.g. *Xiphinema index*.

The compounds of formula (I) can, as the case may be, at certain concentrations or application rates, also be used as herbicides, safeners, growth regulators or agents to improve plant properties, as microbicides or gametocides, for example as fungicides, antimycotics, bactericides, virucides (including agents against viroids) or as agents against MLO (mycoplasma-like organisms) and RLO (rickettsia-like organisms). They can, as the case may be, also be used as intermediates or precursors for the synthesis of other active compounds.

Formulations

The present invention further relates to formulations and use forms prepared therefrom as pesticides, for example drench, drip and spray liquors, comprising at least one compound of formula (I). Optionally, the use forms comprise further pesticides and/or adjuvants which improve action, such as penetrants, e.g. vegetable oils, for example rapeseed oil, sunflower oil, mineral oils, for example paraffin oils, alkyl esters of vegetable fatty acids, for example rapeseed oil methyl ester or soya oil methyl ester, or alkanol alkoxylates and/or spreaders, for example alkylsiloxanes and/or salts, for example organic or inorganic ammonium or phosphonium salts, for example ammonium sulfate or diammonium hydrogenphosphate and/or retention promoters, for example dioctyl sulfosuccinate or hydroxypropylguar polymers and/or humectants, for example glycerol and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers 173, prepared by the FAO/WHO Joint Meeting on Pesticide Specifications, 2004, ISBN: 9251048576. The formulations, in addition to one or more compounds of formula (I), optionally comprise further active agrochemical ingredients.

Preference is given to formulations or use forms comprising auxiliaries, for example extenders, solvents, spontaneity promoters, carriers, emulsifiers, dispersants, frost protection agents, biocides, thickeners and/or further auxiliaries, for example adjuvants. An adjuvant in this context is a component which enhances the biological effect of formulation, without the component itself having any biological effect. Examples of adjuvants are agents which promote retention, spreading, attachment to the leaf surface or penetration.

These formulations are produced in a known manner, for example by mixing the compounds of formula (I) with auxiliaries, for example extenders, solvents and/or solid carriers and/or other auxiliaries, for example surfactants. The formulations are produced either in suitable facilities or else before or during application.

The auxiliaries used may be substances suitable for imparting special properties, such as certain physical, technical and/or biological properties, to the formulation of the compounds of formula (I), or to the use forms prepared from these formulations (for example ready-to-use pesticides such as spray liquors or seed-dressing products).

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the simple and substituted amines, amides, lactams (such as N-alkylpyrrolidones) and lactones, the sulfones and sulfoxides (such as dimethyl sulfoxide).

If the extender utilized is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulfoxide, and also water.

In principle, it is possible to use all suitable solvents. Examples of suitable solvents are aromatic hydrocarbons, for example xylene, toluene or alkylnaphthalenes, chlorinated aromatic or chlorinated aliphatic hydrocarbons, for example chlorobenzene, chloroethylene or methylene chloride, aliphatic hydrocarbons, for example cyclohexane, paraffins, petroleum fractions, mineral and vegetable oils, alcohols, for example methanol, ethanol, isopropanol, butanol or glycol and their ethers and esters, ketones, for example acetone, methyl ethyl ketone, methyl isobutyl ketone or cyclohexanone, strongly polar solvents, for example dimethyl sulfoxide, and water.

In principle, it is possible to use all suitable carriers. Suitable carriers include more particularly the following: for example ammonium salts and natural, finely ground rocks, such as kaolins, aluminas, talc, chalk, quartz, attapulgite, montmorillonite or diatomaceous earth, and synthetic, finely ground rocks, such as finely divided silica, aluminium oxide and natural or synthetic silicates, resins, waxes and/or solid fertilizers. It is likewise possible to use mixtures of such carriers. Useful carriers for granules include: for example crushed and fractionated natural rocks such as calcite, marble, pumice, sepiolite, dolomite, and synthetic granules of inorganic and organic flours, and also granules of organic material such as sawdust, paper, coconut shells, maize cobs and tobacco stalks.

It is also possible to use liquefied gaseous extenders or solvents. Especially suitable extenders or carriers are those which are gaseous at standard temperature and under atmospheric pressure, for example aerosol propellants such as halogenated hydrocarbons, and also butane, propane, nitrogen and carbon dioxide.

Examples of emulsifiers and/or foam formers, dispersants or wetting agents having ionic or nonionic properties or mixtures of these surface-active substances are salts of polyacrylic acid, salts of lignosulfonic acid, salts of phenolsulfonic acid or naphthalenesulfonic acid, polycondensates of ethylene oxide with fatty alcohols or with fatty acids or with fatty amines, with substituted phenols (preferably alkylphenols or arylphenols), salts of sulfosuccinic esters, taurine derivatives (preferably alkyl taurates), phosphoric esters of polyethoxylated alcohols or phenols, fatty acid esters of polyols, and derivatives of the compounds containing sulfates, sulfonates and phosphates, for example alkylaryl polyglycol ethers, alkylsulfonates, alkyl sulfates, arylsulfonates, protein hydrolysates, lignosulfite waste liquors and methylcellulose. The presence of a surfactant is advantageous if one of the compounds of formula (I) and/or one of the inert carriers is insoluble in water and if the application takes place in water.

Further auxiliaries which may be present in the formulations and the use forms derived therefrom include dyes such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc.

Additional components which may be present are stabilizers, such as cold stabilizers, preservatives, antioxidants, light stabilizers, or other agents which improve chemical and/or physical stability. Foam formers or antifoams may also be present.

In addition, the formulations and use forms derived therefrom may also comprise, as additional auxiliaries, stickers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids. Further auxiliaries may be mineral and vegetable oils.

It is possible if appropriate for still further auxiliaries to be present in the formulations and the use forms derived therefrom. Examples of such additives are fragrances, protective colloids, binders, adhesives, thickeners, thixotropic agents, penetrants, retention promoters, stabilizers, sequestrants, complexing agents, humectants, spreaders. In general, the compounds of formula (I) can be combined with any solid or liquid additive commonly used for formulation purposes.

Useful retention promoters include all those substances which reduce dynamic surface tension, for example dioctyl sulfosuccinate, or increase viscoelasticity, for example hydroxypropylguar polymers.

Useful penetrants in the present context are all those substances which are typically used to improve the penetration of agrochemically active compounds into plants. Penetrants are defined in this context by their ability to penetrate from the (generally aqueous) application liquor and/or from the spray coating into the cuticle of the plant and hence to increase the mobility of the active compounds in the cuticle.

The method described in the literature (Baur et al., 1997, Pesticide Science 51, 131-152) can be used for determining this property. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulfate or diammonium hydrogenphosphate.

The formulations preferably comprise between 0.00000001% and 98% by weight of the compound of formula (I), more preferably between 0.01% and 95% by weight of the compound of formula (I), most preferably between 0.5% and 90% by weight of the compound of formula (I), based on the weight of formulation.

The content of the compound of formula (I) in the use forms prepared from the formulations (in particular pesticides) may vary within wide ranges. The concentration of the compound of formula (I) in the use forms may typically be between 0.00000001% and 95% by weight of the compound of formula (I), preferably between 0.00001% and 1% by weight, based on the weight of the use form. Application is accomplished in a customary manner appropriate for the use forms.

Mixtures

The compounds of formula (I) can also be used in a mixture with one or more suitable fungicides, bactericides, acaricides, molluscicides, nematicides, insecticides, microbiological agents, beneficial organisms, herbicides, fertilizers, bird repellents, phytotonics, sterilants, safeners, semiochemicals and/or plant growth regulators, in order thus, for example, to broaden the spectrum of action, prolong the period of action, enhance the rate of action, prevent repellency or prevent evolution of resistance. In addition, active compound combinations of this kind can improve plant growth and/or tolerance to abiotic factors, for example high or low temperatures, to drought or to elevated water content or soil salinity. It is also possible to improve flowering and fruiting performance, optimize germination capacity and root development, facilitate harvesting and improve yields, influence maturation, improve the quality and/or the nutritional value of the harvested products, prolong storage life and/or improve the processability of the harvested products.

In addition, the compounds of formula (I) may be present in a mixture with other active compounds or semiochemicals such as attractants and/or bird repellents and/or plant activators and/or growth regulators and/or fertilizers. Likewise, the compounds of formula (I) can be used to improve plant properties, for example growth, yield and quality of the harvested material.

In a particular embodiment according to the invention, the compounds of formula (I) are present in formulations or in the use forms prepared from these formulations in a mixture with further compounds, preferably those as described below.

If one of the compounds mentioned below can occur in different tautomeric forms, these forms are also included even if not explicitly mentioned in each case. All the mixing components mentioned, as the case may be, may also form salts with suitable bases or acids if they are capable of doing so on the basis of their functional groups.

Insecticides/Acaricides/Nematicides

The active compounds specified here with their common names are known and are described for example in "The Pesticide Manual", 16th ed., British Crop Protection Council 2012, or can be searched for on the Internet (e.g. http://www.alanwood.net/pesticides). The classification is based on the IRAC Mode of Action Classification Scheme applicable at the time of filing of this patent application.

(1) Acetylcholinesterase (AChE) inhibitors, for example carbamates, e.g. alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, e.g. acephate, az amethipho s, azinpho s-ethyl, azinphos-methyl, cadusafos, chlorethoxyfos, chlorfenvinphos, chlormephos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel blockers, for example cyclodiene-organochlorines, e.g. chlordane and endosulfan or phenylpyrazoles (fiproles), e.g. ethiprole and fipronil.

(3) Sodium channel modulators, for example pyrethroids, e.g. acrinathrin, allethrin, d-cis-trans allethrin, d-trans allethrin, bifenthrin, bioallethrin, bioallethrin S-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomer], deltamethrin, empenthrin [(EZ)-(1R) isomer], esfenvalerate, etofenprox, fenpropathrin, fenvalerate, flucythrinate, flumethrin, tau-fluvalinate, halfenprox, imiprothrin, kadethrin, momfluorothrin, permethrin, phenothrin [(1R)-trans isomer], prallethrin, pyrethrins (pyrethrum), resmethrin, silafluofen, tefluthrin, tetramethrin, tetramethrin [(1R) isomer], tralomethrin and transfluthrin or DDT or methoxychlor.

(4) Nicotinic acetylcholine receptor (nAChR) competitive modulators, for example neonicotinoids, e.g. acetamiprid, clothianidin, dinotefuran, imidacloprid, nitenpyram, thiacloprid and thiamethoxam or nicotine or sulfoxaflor or flupyradifurone.

(5) Nicotinic acetylcholine receptor (nAChR) allosteric modulators, for example spinosyns, e.g. spinetoram and spinosad.

(6) Glutamate-gated chloride channel (GluCl) allosteric modulators, for example avermectins/milbemycins, e.g. abamectin, emamectin benzoate, lepimectin and milbemectin.

(7) Juvenile hormone mimetics, for example juvenile hormone analogues, e.g. hydroprene, kinoprene and methoprene or fenoxycarb or pyriproxyfen.

(8) Miscellaneous non-specific (multisite) inhibitors, for example alkyl halides, e.g. methyl bromide and other alkyl halides; or chloropicrin or sulfuryl fluoride or borax or tartar emetic or methyl isocyanate generator, e.g. diazomet and metam.

(9) Chordotonal organ modulators, e.g. pymetrozine or flonicamid.

(10) Mite growth inhibitors, for example clofentezine, hexythiazox and diflovidazin or etoxazole.

(11) Microbial disruptors of the insect midgut membrane, for example *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis* and B.t. plant proteins: Cry1Ab, Cry1Ac, Cry1Fa, Cry1A.105, Cry2Ab, VIP3A, mCry3A, Cry3Ab, Cry3Bb, Cry34Ab1/35Ab1.

(12) Inhibitors of mitochondrial ATP synthase, such as ATP disruptors, for example diafenthiuron or organotin compounds, e.g. azocyclotin, cyhexatin and fenbutatin oxide or propargite or tetradifon.

(13) Uncouplers of oxidative phosphorylation via disruption of the proton gradient, for example chlorfenapyr, DNOC and sulfluramid.

(14) Nicotinic acetylcholine receptor channel blockers, for example bensultap, cartap hydrochloride, thiocyclam, and thiosultap-sodium.

(15) Inhibitors of chitin biosynthesis, type 0, for example bistrifluron, chlorfluazuron, diflubenzuron, flucycloxuron, flufenoxuron, hexaflumuron, lufenuron, novaluron, noviflumuron, teflubenzuron and triflumuron.

(16) Inhibitors of chitin biosynthesis, type 1, for example buprofezin.

(17) Moulting disruptors (especially in the case of Diptera), for example cyromazine.

(18) Ecdysone receptor agonists such as, for example, chromafenozide, halofenozide, methoxyfenozide and tebufenozide.

(19) Octopamine receptor agonists, for example amitraz.

(20) Mitochondrial complex III electron transport inhibitors, for example hydramethylnon or acequinocyl or fluacrypyrim.

(21) Mitochondrial complex I electron transport inhibitors, for example METI acaricides, e.g. fenazaquin, fenpyroximate, pyrimidifen, pyridaben, tebufenpyrad and tolfenpyrad or rotenone (Derris).

(22) Voltage-dependent sodium channel blockers, for example indoxacarb or metaflumizone.

(23) Inhibitors of acetyl CoA carboxylase, for example tetronic and tetramic acid derivatives, e.g. spirodiclofen, spiromesifen and spirotetramat.

(24) Mitochondrial complex IV electron transport inhibitors, for example phosphines, e.g. aluminium phosphide, calcium phosphide, phosphine and zinc phosphide, or cyanides, calcium cyanide, potassium cyanide and sodium cyanide.

(25) Mitochondrial complex II electron transport inhibitors, for example beta-keto nitrile derivatives, e.g. cyenopyrafen and cyflumetofen and carboxanilides, for example pyflubumide.

(28) Ryanodine receptor modulators, for example diamides, e.g. chlorantraniliprole, cyantraniliprole and flubendiamide, further active compounds, for example afidopyropen, afoxolaner, azadirachtin, benclothiaz, benzoximate, bifenazate, broflanilide, bromopropylate, chinomethionat, chloroprallethrin, cryolite, cyclaniliprole, cycloxaprid, cyhalodiamide, dicloromezotiaz, dicofol, epsilon metofluthrin, epsilon momfluthrin, flometoquin, fluazaindolizine, fluensulfone, flufenerim, flufenoxystrobin, flufiprole, fluhexafon, fluopyram, fluralaner, fluxametamide, fufenozide, guadipyr, heptafluthrin, imidaclothiz, iprodione, kappa bifenthrin, kappa tefluthrin, lotilaner, meperfluthrin, paichongding, pyridalyl, pyrifluquinazon, pyriminostrobin, spirobudiclofen, tetramethylfluthrin, tetraniliprole, tetrachlorantraniliprole, tigolaner, tioxazafen, thiofluoximate, triflumezopyrim and iodomethane; additionally preparations based on *Bacillus firmus* (I-1582, BioNeem, Votivo), and the following compounds: 1-{2-fluoro-4-methyl-5-[(2,2,2-trifluoroethyl)sulfinyl]phenyl}-3-(trifluoromethyl)-1H-1,2,4-triazole-5-amine (known from WO2006/043635) (CAS 885026-50-6), {1'-[(2E)-3-(4-chlorophenyl)prop-2-en-1-yl]-5-fluorospiro[indole-3,4'-piperidine]-1(2H)-yl}(2-chloropyridin-4-yl)methanone (known from WO2003/106457) (CAS 637360-23-7), 2-chloro-N-[2-{1-[(2E)-3-(4-chlorophenyl)prop-2-en-1-yl]piperidin-4-yl}-4-(trifluoromethyl) phenyl]isonicotinamide (known from WO2006/003494) (CAS 872999-66-1), 3-(4-chloro-2,6-dimethylphenyl)-4-hydroxy-8-methoxy-1,8-diazaspiro[4.5]dec-3-en-2-one (known from WO 2010052161) (CAS 1225292-17-0), 3-(4-chloro-2,6-dimethylphenyl)-8-methoxy-2-oxo-1,8-diazaspiro[4.5]dec-3-en-4-yl ethylcarbonate (known from EP 2647626) (CAS-1440516-42-6), 4-(but-2-yn-1-yloxy)-6-(3,5-dimethylpiperidin-1-yl)-5-fluoropyrimidine (known from WO2004/099160) (CAS 792914-58-0), PF1364 (known from JP2010/018586) (CAS Reg. No. 1204776-60-2), N-[(2E)-1-[(6-chloropyridin-3-yl)methyl]pyridin-2(1H)-ylidene]-2,2,2-trifluoroacetamide (known from WO2012/029672) (CAS 1363400-41-2), (3E)-3-[1-[(6-chloro-3-pyridyl)methyl]-2-pyridylidene]-1,1,1-trifluoropropan-2-one (known from WO2013/144213) (CAS 1461743-15-6), N-[3-(benzylcarbamoyl)-4-chlorophenyl]-1-methyl-3-(pentafluoroethyl)-4-(trifluoromethyl)-1H-pyrazole-5-carboxamide (known from WO2010/051926) (CAS 1226889-14-0), 5-bromo-4-chloro-N-[4-chloro-2-methyl-6-(methylcarbamoyl)phenyl]-2-(3-chloro-2-pyridyl)pyrazole-3-carboxamide (known from CN103232431) (CAS 1449220-44-3), 4-[5-(3,5-dichlorophenyl)-4,5-dihydro-5-(trifluoromethyl)-3-isoxazolyl]-2-methyl-N-(cis-1-oxido-3-thietanyl)benzamide, 4-[5-(3,5-dichlorophenyl)-4,5-dihydro-5-(trifluoromethyl)-3-isoxazolyl]-2-methyl-N-(trans-1-oxido-3-thietanyl)benzamide and 4-[(5S)-5-(3,5-dichlorophenyl)-4,5-dihydro-5-(trifluoromethyl)-3-isoxazolyl]-2-methyl-N-(cis-1-oxido-3-thietanyl)benzamide (known from WO 2013/050317 A1) (CAS 1332628-83-7), N-[3-chloro-1-(3-pyridinyl)-1H-pyrazol-4-yl]-N-ethyl-3-[(3,3,3-trifluoropropyl) sulfinyl]propanamide, (+)-N-[3-chloro-1-(3-pyridinyl)-1H-pyrazol-4-yl]-N-ethyl-3-[(3,3,3-trifluoropropyl)sulfinyl]propanamide and (−)-N-[3-chloro-1-(3-pyridinyl)-1H-pyrazol-4-yl]-N-ethyl-3-[(3,3,3-trifluoropropyl)sulfinyl]propanamide (known from WO 2013/162715 A2, WO 2013/162716 A2, US 2014/0213448 A1) (CAS 1477923-37-7), 5-[[(2E)-3-chloro-2-propen-1-yl]amino]-1-[2,6-dichloro-4-(trifluoromethyl)phenyl]-4-[(trifluoromethyl) sulfinyl]-1H-pyrazole-3-carbonitrile (known from CN 101337937 A) (CAS 1105672-77-2), 3-bromo-N-[4-chloro-2-methyl-6-[(methyl amino)thioxomethyl]phenyl]-1-(3-chloro-2-pyridinyl)-1H-pyrazole-5-carboxamide (Liudaibenjiaxuanan, known from CN 103109816 A) (CAS 1232543-85-9); N-[4-chloro-2-[[(1,1-dimethylethyl)amino] carbonyl]-6-methylphenyl]-1-(3-chloro-2-pyridinyl)-3-(fluoromethoxy)-1H-pyrazole-5-carboxamide (known from WO 2012/034403 A1) (CAS 1268277-22-0), N-[2-(5-amino-1,3,4-thiadiazol-2-yl)-4-chloro-6-methylphenyl]-3-bromo-1-(3-chloro-2-pyridinyl)-1H-pyrazole-5-carboxamide (known from WO 2011/085575 A1) (CAS 1233882-22-8), 4-[3-[2,6-dichloro-4-[(3,3-dichloro-2-propen-1-yl)oxy]phenoxy]propoxy]-2-methoxy-6-(trifluoromethyl) pyrimidine (known from CN 101337940 A) (CAS 1108184-52-6); (2E)- and 2(Z)-2-[2-(4-cyanophenyl)-1-[3-(trifluoromethyl)phenyl]ethylidene]-N-[4-(difluoromethoxy)phenyl]hydrazinecarboxamide (known from CN 101715774 A) (CAS 1232543-85-9); cyclopropanecarboxylic acid 3-(2,2-dichloroethenyl)-2,2-dimethyl-4-

(1H-benzimidazol-2-yl)phenyl ester (known from CN 103524422 A) (CAS 1542271-46-4); (4aS)-7-chloro-2,5-dihydro-2-[[(methoxycarbonyl) [4-[(trifluoromethyl)thio]phenyl]amino]carbonyl]indeno[1,2-e][1,3,4]oxadiazine-4a (3H)-carboxylic acid methyl ester (known from CN 102391261 A) (CAS 1370358-69-2); 6-deoxy-3-O-ethyl-2,4-di-O-methyl-1-[N-[4-[1-[4-(1,1,2,2,2-pentafluoroethoxy)phenyl]-1H-1,2,4-triazol-3-yl]phenyl]carbamate]-α-L-mannopyranose (known from US 2014/0275503 A1) (CAS 1181213-14-8); 8-(2-cyclopropylmethoxy-4-trifluoromethylphenoxy)-3-(6-trifluoromethylpyridazin-3-yl)-3-azabicyclo[3.2.1]octane (CAS 1253850-56-4), (8-anti)-8-(2-cyclopropylmethoxy-4-trifluoromethylphenoxy)-3-(6-trifluoromethylpyridazin-3-yl)-3-azabicyclo[3.2.1]octane (CAS 933798-27-7), (8-syn)-8-(2-cyclopropylmethoxy-4-trifluoromethylphenoxy)-3-(6-trifluoromethylpyridazin-3-yl)-3-azabicyclo[3.2.1]octane (known from WO 2007040280 A1, WO 2007040282 A1) (CAS 934001-66-8), N-[3-chloro-1-(3-pyridinyl)-1H-pyrazol-4-yl]-N-ethyl-3-[(3,3,3-trifluoropropyl)thio]propanamide (known from WO 2015/058021 A1, WO 2015/058028 A1) (CAS 1477919-27-9) and N-[4-(aminothioxomethyl)-2-methyl-6-[(methylamino)carbonyl]phenyl]-3-bromo-1-(3-chloro-2-pyridinyl)-1H-pyrazole-5-carboxamide (known from CN 103265527 A) (CAS 1452877-50-7), 5-(1,3-dioxan-2-yl)-4-[[4-(trifluoromethyl)phenyl]methoxy]pyrimidine (known from WO 2013/115391 A1) (CAS 1449021-97-9), 3-(4-chloro-2,6-dimethylphenyl)-4-hydroxy-8-methoxy-1-methyl-1,8-diazaspiro[4.5]dec-3-en-2-one (known from WO 2010/066780 A1, WO 2011/151146 A1) (CAS 1229023-34-0), 3-(4-chloro-2,6-dimethylphenyl)-8-methoxy-1-methyl-1,8-diazaspiro[4.5]decane-2,4-dione (known from WO 2014/187846 A1) (CAS 1638765-58-8), ethyl 3-(4-chloro-2,6-dimethylphenyl)-8-methoxy-1-methyl-2-oxo-1,8-diazaspiro[4.5]dec-3-en-4-yl-carboxylate (known from WO 2010/066780 A1, WO 2011151146 A1) (CAS 1229023-00-0), N-[1-[(6-chloro-3-pyridinyl)methyl]-2(1H)-pyridinylidene]-2,2,2-trifluoroacetamide (known from DE 3639877 A1, WO 2012029672 A1) (CAS 1363400-41-2), [N(E)]-N-[1-[(6-chloro-3-pyridinyl)methyl]-2(1H)-pyridinylidene]-2,2,2-trifluoroacetamide (known from WO 2016005276 A1) (CAS 1689566-03-7), [N(Z)]—N-[1-[(6-chloro-3-pyridinyl)methyl]-2(1H)-pyridinylidene]-2,2,2-trifluoroacetamide (CAS 1702305-40-5), 3-endo-3-[2-propoxy-4-(trifluoromethyl)phenoxy]-9-[[5-(trifluoromethyl)-2-pyridinyl]oxy]-9-azabicyclo[3.3.1]nonane (known from WO 2011/105506 A1, WO 2016/133011 A1) (CAS 1332838-17-1).

Fungicides

The active ingredients specified herein by their common name are known and described, for example, in "Pesticide Manual" (16th Ed. British Crop Protection Council) or searchable on the Internet (for example:).

All the mixing components mentioned in classes (1) to (15), as the case may be, may form salts with suitable bases or acids if they are capable of doing so on the basis of their functional groups. All the fungicidal mixing components mentioned in classes (1) to (15), as the case may be, may include tautomeric forms.

1) Ergosterol biosynthesis inhibitors, for example (1.001) cyproconazole, (1.002) difenoconazole, (1.003) epoxiconazole, (1.004) fenhexamid, (1.005) fenpropidin, (1.006) fenpropimorph, (1.007) fenpyrazamine, (1.008) fluquinconazole, (1.009) flutriafol, (1.010) imazalil, (1.011) imazalil sulfate, (1.012) ipconazole, (1.013) metconazole, (1.014) myclobutanil, (1.015) paclobutrazole, (1.016) prochloraz, (1.017) propiconazole, (1.018) prothioconazole, (1.019) pyrisoxazole, (1.020) spiroxamine, (1.021) tebuconazole, (1.022) tetraconazole, (1.023) triadimenol, (1.024) tridemorph, (1.025) triticonazole, (1.026) (1R,2S,5S)-5-(4-chlorobenzyl)-2-(chloromethyl)-2-methyl-1-(1H-1,2,4-triazol-1-ylmethyl)cyclopentanol, (1.027) (1S,2R,5R)-5-(4-chlorobenzyl)-2-(chloromethyl)-2-methyl-1-(1H-1,2,4-triazol-1-ylmethyl)cyclopentanol, (1.028) (2R)-2-(1-chlorocyclopropyl)-4-[(1R)-2,2-dichlorocyclopropyl]-1-(1H-1,2,4-triazol-1-yl)butan-2-ol (1.029) (2R)-2-(1-chlorocyclopropyl)-4-[(1S)-2,2-dichlorocyclopropyl]-1-(1H-1,2,4-triazol-1-yl)butan-2-ol, (1.030) (2R)-2-[4-(4-chlorophenoxy)-2-(trifluoromethyl)phenyl]-1-(1H-1,2,4-triazol-1-yl)propan-2-ol, (1.031) (2S)-2-(1-chlorocyclopropyl)-4-[(1R)-2,2-dichlorocyclopropyl]-1-(1H-1,2,4-triazol-1-yl)butan-2-ol, (1.032) (2S)-2-(1-chlorocyclopropyl)-4-[(1S)-2,2-dichlorocyclopropyl]-1-(1H-1,2,4-triazol-1-yl)butan-2-ol, (1.033) (2S)-2-[4-(4-chlorophenoxy)-2-(trifluoromethyl)phenyl]-1-(1H-1,2,4-triazol-1-yl)propan-2-ol, (1.034) (R)-[3-(4-chloro-2-fluorophenyl)-5-(2,4-difluorophenyl)-1,2-oxazol-4-yl](pyridin-3-yl)methanol, (1.035) (S)-[3-(4-chloro-2-fluorophenyl)-5-(2,4-difluorophenyl)-1,2-oxazol-4-yl](pyridin-3-yl)methanol, (1.036) [3-(4-chloro-2-fluorophenyl)-5-(2,4-difluorophenyl)-1,2-oxazol-4-yl](pyridin-3-yl)methanol, (1.037) 1-({(2R,4S)-2-[2-chloro-4-(4-chlorophenoxy)phenyl]-4-methyl-1,3-dioxolan-2-yl}methyl)-1H-1,2,4-triazole, (1.038) 1-({(2S,4S)-2-[2-chloro-4-(4-chlorophenoxy)phenyl]-4-methyl-1,3-dioxolan-2-yl}methyl)-1H-1,2,4-triazole, (1.039) 1-{[3-(2-chlorophenyl)-2-(2,4-difluorophenyl)oxiran-2-yl]methyl}-1H-1,2,4-triazol-5-yl thiocyanate, (1.040) 1-{[rel(2R,3R)-3-(2-chlorophenyl)-2-(2,4-difluorophenyl)oxiran-2-yl]methyl}-1H-1,2,4-triazol-5-yl thiocyanate, (1.041) 1-{[rel(2R,3S)-3-(2-chlorophenyl)-2-(2,4-difluorophenyl)oxiran-2-yl]methyl}-1H-1,2,4-triazol-5-yl thiocyanate, (1.042) 2-[(2R,4R,5R)-1-(2,4-dichlorophenyl)-5-hydroxy-2,6,6-trimethylheptan-4-yl]-2,4-dihydro-3H-1,2,4-triazole-3-thione, (1.043) 2-[(2R,4R,5S)-1-(2,4-dichlorophenyl)-5-hydroxy-2,6,6-trimethylheptan-4-yl]-2,4-dihydro-3H-1,2,4-triazole-3-thione, (1.044) 2-[(2R,4S,5R)-1-(2,4-dichlorophenyl)-5-hydroxy-2,6,6-trimethylheptan-4-yl]-2,4-dihydro-3H-1,2,4-triazole-3-thione, (1.045) 2-[(2R,4S,5S)-1-(2,4-dichlorophenyl)-5-hydroxy-2,6,6-trimethylheptan-4-yl]-2,4-dihydro-3H-1,2,4-triazole-3-thione, (1.046) 2-[(2S,4R,5R)-1-(2,4-dichlorophenyl)-5-hydroxy-2,6,6-trimethylheptan-4-yl]-2,4-dihydro-3H-1,2,4-triazole-3-thione, (1.047) 2-[(2S,4R,5S)-1-(2,4-dichlorophenyl)-5-hydroxy-2,6,6-trimethylheptan-4-yl]-2,4-dihydro-3H-1,2,4-triazole-3-thione, (1.048) 2-[(2S,4S,5R)-1-(2,4-dichlorophenyl)-5-hydroxy-2,6,6-trimethylheptan-4-yl]-2,4-dihydro-3H-1,2,4-triazole-3-thione, (1.049) 2-[(2S,4S,5S)-1-(2,4-dichlorophenyl)-5-hydroxy-2,6,6-trimethylheptan-4-yl]-2,4-dihydro-3H-1,2,4-triazole-3-thione, (1.050) 2-[1-(2,4-dichlorophenyl)-5-hydroxy-2,6,6-trimethylheptan-4-yl]-2,4-dihydro-3H-1,2,4-triazole-3-thione, (1.051) 2-[2-chloro-4-(2,4-dichlorophenoxy)phenyl]-1-(1H-1,2,4-triazol-1-yl)propan-2-ol, (1.052) 2-[2-chloro-4-(4-chlorophenoxy)phenyl]-1-(1H-1,2,4-triazol-1-yl)butan-2-ol, (1.053) 2-[4-(4-chlorophenoxy)-2-(trifluoromethyl)phenyl]-1-(1H-1,2,4-triazol-1-yl)butan-2-ol, (1.054) 2-[4-(4-chlorophenoxy)-2-(trifluoromethyl)phenyl]-1-(1H-1,2,4-triazol-1-yl)pentan-2-ol, (1.055) 2-[4-(4-chlorophenoxy)-2-(trifluoromethyl)phenyl]-1-(1H-1,2,4-triazol-1-yl)propan-2-ol, (1.056) 2-{[3-(2-chlorophenyl)-2-(2,4-difluorophenyl)oxiran-2-yl]methyl}-2,4-dihydro-3H-1,2,4-triazole-3-thione, (1.057) 2-{[rel(2R,3R)-3-(2-chlorophenyl)-2-(2,4-difluorophenyl)oxiran-2-yl]methyl}-2,4-dihydro-3H-1,2,4-triazole-3- thione, (1.058) 2-{[rel(2R,3S)-3-(2-chlorophenyl)-2-(2,4-difluorophenyl)oxiran-2-yl]methyl}-2,4-dihydro-3H-1,2,4-triazole-3-thione, (1.059) 5-(4-chlorobenzyl)-2-(chloromethyl)-2-methyl-1-(1H-1,2,4-triazol-1-ylmethyl)cyclopentanol, (1.060) 5-(allylsulfanyl)-1-{[3-(2-chlorophenyl)-2-(2,4-difluorophenyl)oxiran-2-yl]methyl}-1H-1,2,4-triazole, (1.061) 5-(allylsulfanyl)-1-{[rel(2R,3R)-3-(2-chlorophenyl)-2-(2,4-difluorophenyl)oxiran-2-yl]methyl}-1H-1,2,4-triazole, (1.062) 5-(allylsulfanyl)-1-{[rel(2R,3S)-3-(2-chlorophenyl)-2-(2,4-difluorophenyl)oxiran-2-yl]methyl}-1H-1,2,4-triazole, (1.063) N'-(2,5-dimethyl-4-{[3-(1,1,2,2-tetrafluoroethoxy)phenyl]sulfanyl}phenyl)-N-ethyl-N-methylimidoformamide, (1.064) N'-(2,5-dimethyl-4-{[3-(2,2,2-trifluoroethoxy)phenyl]sulfanyl}phenyl)-N-ethyl-N-methylimidoformamide, (1.065) N'-(2,5-dimethyl-4-{[3-(2,2,3,3-tetrafluoropropoxy)phenyl]sulfanyl}phenyl)-N-ethyl-N-methylimidoformamide, (1.066) N'-(2,5-dimethyl-4-{[3-(pentafluoroethoxy)phenyl]sulfanyl}phenyl)-N-ethyl-N-methylimidoformamide, (1.067) N'-(2,5-dimethyl-4-{3-[(1,1,2,2-tetrafluoroethyl)sulfanyl]phenoxy}phenyl)-N-ethyl-N-methylimidoformamide, (1.068) N'-(2,5-dimethyl-4-{3-[(2,2,2-trifluoroethyl)sulfanyl]phenoxy}phenyl)-N-ethyl-N-methylimidoformamide, (1.069) N'-(2,5-dimethyl-4-{3-[(2,2,3,3-tetrafluoropropyl)sulfanyl]phenoxy}phenyl)-N-ethyl-N-methylimidoformamide, (1.070) N'-(2,5-dimethyl-4-{3-[(pentafluoroethyl)sulfanyl]phenoxy}phenyl)-N-ethyl-N-methylimidoformamide, (1.071) N'-(2,5-dimethyl-4-phenoxyphenyl)-N-ethyl-N-methylimidoformamide, (1.072) N'-(4-{[3-(difluoromethoxy)phenyl]sulfanyl}-2,5-dimethylphenyl)-N-ethyl-N-methylimidoformamide, (1.073) N'-(4-{3-[(difluoromethyl)sulfanyl]phenoxy}-2,5-dimethylphenyl)-N-ethyl-N-methylimidoformamide, (1.074) N'-[5-bromo-6-(2,3-dihydro-1H-inden-2-yloxy)-2-methylpyridin-3-yl]-N-ethyl-N-methylimidoformamide, (1.075) N'-{4-[(4,5-dichloro-1,3-thiazol-2-yl)oxy]-2,5-dimethylphenyl}-N-ethyl-N-methylimidoformamide, (1.076) N'-{5-bromo-6-[(1R)-1-(3,5-difluorophenyl)ethoxy]-2-methylpyridin-3-yl}-N-ethyl-N-methylimidoformamide, (1.077) N'-{5-bromo-6-1(1S)-1-(3,5-difluorophenyl)ethoxyl-2-methylpyridin-3-yl}-N-ethyl-N-methylimidoformamide, (1.078) N'-{5-bromo-6-[(cis-4-isopropylcyclohexyl)oxy]-2-methylpyridin-3-yl}-N-ethyl-N-methylimidoformamide, (1.079) N'-{5-bromo-6-[(trans-4-isopropylcyclohexyl)oxy]-2-methylpyridin-3-yl}-N-ethyl-N-methylimidoformamide, (1.080) N'-{5-bromo-6-[1-(3,5-difluorophenyl)ethoxy]-2-methylpyridin-3-yl}-N-ethyl-N-methylimidoformamide, (1.081) mefentrifluconazole, (1.082) ipfentrifluconazole.

2) Inhibitors of the respiratory chain in complex I or II, for example (2.001) benzovindiflupyr, (2.002) bixafen, (2.003) boscalid, (2.004) carboxin, (2.005) fluopyram, (2.006) flutolanil, (2.007) fluxapyroxad, (2.008) furametpyr, (2.009) isofetamid, (2.010) isopyrazam (anti-epimeric enantiomer 1R,4S,9S), (2.011) isopyrazam (anti-epimeric enantiomer 1S,4R,9R), (2.012) isopyrazam (anti-epimeric racemate 1RS,4SR,9SR), (2.013) isopyrazam (mixture of the syn-epimeric racemate 1RS,4SR,9RS and the anti-epimeric racemate 1RS,4SR,9SR), (2.014) isopyrazam (syn-epimeric enantiomer 1R,4S,9R), (2.015) isopyrazam (syn-epimeric enantiomer 1S,4R,9S), (2.016) isopyrazam (syn-epimeric racemate 1RS,4SR,9RS), (2.017) penflufen, (2.018) penthiopyrad, (2.019) pydiflumetofen, (2.020) pyraziflumid, (2.021) sedaxane, (2.022) 1,3-dimethyl-N-(1,1,3-trimethyl-2,3-dihydro-1H-inden-4-yl)-1H-pyrazole-4-carboxamide, (2.023) 1,3-dimethyl-N-[(3R)-1,1,3-trimethyl-2,3-dihydro-1H-inden-4-yl]-1H-pyrazole-4-carboxamide, (2.024) 1,3-dimethyl-N-[(3S)-1,1,3-trimethyl-2,3-dihydro-1H-inden-4-yl]-1H-pyrazole-4-carboxamide, (2.025) 1-methyl-3-(trifluoromethyl)-N-[2'-(trifluoromethyl)biphenyl-2-yl]-1H-pyrazole-4-carboxamide, (2.026) 2-fluoro-6-(trifluoromethyl)-N-(1,1,3-trimethyl-2,3-dihydro-1H-inden-4-yl)benzamide, (2.027) 3-(difluoromethyl)-1-methyl-N-(1,1,3-trimethyl-2,3-dihydro-1H-inden-4-yl)-1H-pyrazole-4-carboxamide, (2.028) 3-(difluoromethyl)-1-methyl-N-[(3R)-1,1,3-trimethyl-2,3-dihydro-1H-inden-4-yl]-1H-pyrazole-4-carboxamide, (2.029) 3-(difluoromethyl)-1-methyl-N-[(3S)-1,1,3-trimethyl-2,3-dihydro-1H-inden-4-yl]-1H-pyrazole-4-carboxamide, (2.030) 3-(difluoromethyl)-N-(7-fluoro-1,1,3-trimethyl-2,3-dihydro-1H-inden-4-yl)-1-methyl-1H-pyrazole-4-carboxamide, (2.031) 3-(difluoromethyl)-N-[(3R)-7-fluoro-1,1,3-trimethyl-2,3-dihydro-1H-inden-4-yl]-1-methyl-1H-pyrazole-4-carboxamide, (2.032) 3-(difluoromethyl)-N-[(3S)-7-fluoro-1,1,3-trimethyl-2,3-dihydro-1H-inden-4-yl]-1-methyl-1H-pyrazole-4-carboxamide, (2.033) 5,8-difluoro-N-[2-(2-fluoro-4-{[4-(trifluoromethyl)pyridin-2-yl]oxy}phenyl)ethyl]quinazolin-4-amine, (2.034) N-(2-cyclopentyl-5-fluorobenzyl)-N-cyclopropyl-3-(difluoromethyl)-5-fluoro-1-methyl-1H-pyrazole-4-carboxamide, (2.035) N-(2-tert-butyl-5-methylbenzyl)-N-cyclopropyl-3-(difluoromethyl)-5-fluoro-1-methyl-1H-pyrazole-4-carboxamide, (2.036) N-(2-tert-butylbenzyl)-N-cyclopropyl-3-(difluoromethyl)-5-fluoro-1-methyl-1H-pyrazole-4-carboxamide, (2.037) N-(5-chloro-2-ethylbenzyl)-N-cyclopropyl-3-(difluoromethyl)-5-fluoro-1-methyl-1H-pyrazole-4-carboxamide, (2.038) N-(5-chloro-2-isopropylbenzyl)-N-cyclopropyl-3-(difluoromethyl)-5-fluoro-1-methyl-1H-pyrazole-4-carboxamide, (2.039) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.040) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide, (2.041) N-[1-(2,4-dichlorophenyl)-1-methoxypropan-2-yl]-3-(difluoromethyl)-1-methyl-1H-pyrazole-4-carboxamide, (2.042) N-[2-chloro-6-(trifluoromethyl)benzyl]-N-cyclopropyl-3-(difluoromethyl)-5-fluoro-1-methyl-1H-pyrazole-4-carboxamide, (2.043) N-[3-chloro-2-fluoro-6-(trifluoromethyl)benzyl]-N-cyclopropyl-3-(difluoromethyl)-5-fluoro-1-methyl-1H-pyrazole-4-carboxamide, (2.044) N-[5-chloro-2-(trifluoromethyl)benzyl]-N-cyclopropyl-3-(difluoromethyl)-5-fluoro-1-methyl-1H-pyrazole-4-carboxamide, (2.045) N-cyclopropyl-3-(difluoromethyl)-5-fluoro-1-methyl-N-[5-methyl-2-(trifluoromethyl)benzyl]-1H-pyrazole-4-carboxamide, (2.046) N-cyclopropyl-3-(difluoromethyl)-5-fluoro-N-(2-fluoro-6-isopropylbenzyl)-1-methyl-1H-pyrazole-4-carboxamide, (2.047) N-cyclopropyl-3-(difluoromethyl)-5-fluoro-N-(2-isopropyl-5-methylbenzyl)-1-methyl-1H-pyrazole-4-carboxamide, (2.048) N-cyclopropyl-3-(difluoromethyl)-5-fluoro-N-(2-isopropylbenzyl)-1-methyl-1H-pyrazole-4-carbothioamide, (2.049) N-cyclopropyl-3-(difluoromethyl)-5-fluoro-N-(2-isopropylbenzyl)-1-methyl-1H-pyrazole-4-carboxamide, (2.050) N-cyclopropyl-3-(difluoromethyl)-5-fluoro-N-(5-fluoro-2-isopropylbenzyl)-1-methyl-1H-pyrazole-4-carboxamide, (2.051) N-cyclopropyl-3-(difluoromethyl)-N-(2-ethyl-4,5-dimethylbenzyl)-5-fluoro-1-methyl-1H-pyrazole-4-carboxamide, (2.052) N-cyclopropyl-3-(difluoromethyl)-N-(2-ethyl-5-fluorobenzyl)-5-fluoro-1-methyl-1H-pyrazole-4-carboxamide, (2.053) N-cyclopropyl-3-(difluoromethyl)-N-(2-ethyl-5-methylbenzyl)-5-fluoro-1-methyl-1H-pyrazole-4-carboxamide, (2.054) N-cyclopropyl-N-(2-cyclopropyl-5-fluorobenzyl)-3-(difluoromethyl)-5-fluoro-1-methyl-1H-pyrazole-4-carboxamide, (2.055) N-cyclopropyl-N-(2-cyclopropyl-5-methylbenzyl)-3-(difluoromethyl)-5-fluoro-1-methyl-1H-pyrazole-4-carboxamide, (2.056) N-cyclopropyl-N-(2-cyclopropylbenzyl)-3-(difluoromethyl)-5-fluoro-1-methyl-1H-pyrazole-4-carboxamide.

3) Inhibitors of the respiratory chain at complex III, for example (3.001) ametoctradin, (3.002) amisulbrom, (3.003) azoxystrobin, (3.004) coumethoxystrobin, (3.005) coumoxystrobin, (3.006) cyazofamid, (3.007) dimoxystrobin, (3.008) enoxastrobin, (3.009) famoxadon, (3.010) fenamidon, (3.011) flufenoxystrobin, (3.012) fluoxastrobin, (3.013) kresoxim-methyl, (3.014) metominostrobin, (3.015) orysastrobin, (3.016) picoxystrobin, (3.017) pyraclostrobin, (3.018) pyrametostrobin, (3.019) pyraoxystrobin, (3.020) trifloxystrobin, (3.021) (2E)-2-{2-[({[(1E)-1-(3-{[(E)-1-fluoro-2-phenylvinyl]oxy}phenyl)ethylidene]amino}oxy)methyl]phenyl}-2-(methoxyimino)-N-methylacetamide, (3.022) (2E,3Z)-5-{[1-(4-chlorophenyl)-1H-pyrazol-3-yl]oxy}-2-(methoxyimino)-N,3-dimethylpent-3-enamide, (3.023) (2R)-2-{2-[(2,5-dimethylphenoxy)methyl]phenyl}-2-methoxy-N-methylacetamide, (3.024) (2S)-2-{2-[(2,5-dimethylphenoxy)methyl]phenyl}-2-methoxy-N-methylacetamide, (3.025) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (3.026) 2-{2-[(2,5-dimethylphenoxy)methyl]phenyl}-2-methoxy-N-methylacetamide, (3.027) N-(3-ethyl-3,5,5-trimethylcyclohexyl)-3-formamido-2-hydroxybenzamide, (3.028) (2E,3Z)-5-{[1-(4-chloro-2-fluorophenyl)-1H-pyrazol-3-yl]oxy}-2-(methoxyimino)-N,3-dimethylpent-3-enamide, (3.029) methyl {5-[3-(2,4-dimethylphenyl)-1H-pyrazol-1-yl]-2-methylbenzyl}carbamate.

4) Mitosis and cell division inhibitors, for example (4.001) carbendazim, (4.002) diethofencarb, (4.003) ethaboxam, (4.004) fluopicolid, (4.005) pencycuron, (4.006) thiabendazole, (4.007) thiophanate-methyl, (4.008) zoxamide, (4.009) 3-chloro-4-(2,6-difluorophenyl)-6-methyl-5-phenylpyridazine, (4.010) 3-chloro-5-(4-chlorophenyl)-4-(2,6-difluorophenyl)-6-methylpyridazine, (4.011) 3-chloro-5-(6-chloropyridin-3-yl)-6-methyl-4-(2,4,6-trifluorophenyl)pyridazine, (4.012) 4-(2-bromo-4-fluorophenyl)-N-(2,6-difluorophenyl)-1,3-dimethyl-1H-pyrazol-5-amine, (4.013) 4-(2-bromo-4-fluorophenyl)-N-(2-bromo-6-fluorophenyl)-1,3-dimethyl-1H-pyrazol-5-amine, (4.014) 4-(2-bromo-4-fluorophenyl)-N-(2-bromophenyl)-1,3-dimethyl-1H-pyrazol-5-amine, (4.015) 4-(2-bromo-4-fluorophenyl)-N-(2-chloro-6-fluorophenyl)-1,3-dimethyl-1H-pyrazol-5-amine, (4.016) 4-(2-bromo-4-fluorophenyl)-N-(2-chlorophenyl)-1,3-dimethyl-1H-pyrazol-5-amine, (4.017) 4-(2-bromo-4-fluorophenyl)-N-(2-fluorophenyl)-1,3-dimethyl-1H-pyrazol-5-amine, (4.018) 4-(2-chloro-4-fluorophenyl)-N-(2,6-difluorophenyl)-1,3-dimethyl-1H-pyrazol-5-amine, (4.019) 4-(2-chloro-4-fluorophenyl)-N-(2-chloro-6-fluorophenyl)-1,3-dimethyl-1H-pyrazol-5-amine, (4.020) 4-(2-chloro-4-fluorophenyl)-N-(2-chlorophenyl)-1,3-dimethyl-1H-pyrazol-5-amine, (4.021) 4-(2-chloro-4-fluorophenyl)-N-(2-fluorophenyl)-1,3-dimethyl-1H-pyrazol-5-amine, (4.022) 4-(4-chlorophenyl)-5-(2,6-difluorophenyl)-3,6-dimethylpyridazine, (4.023) N-(2-bromo-6-fluorophenyl)-4-(2-chloro-4-fluorophenyl)-1,3-dimethyl-1H-pyrazol-5-amine, (4.024) N-(2-bromophenyl)-4-(2-chloro-4-fluorophenyl)-1,3-dimethyl-1H-pyrazol-5-amine, (4.025) N-(4-chloro-2,6-difluorophenyl)-4-(2-chloro-4-fluorophenyl)-1,3-dimethyl-1H-pyrazol-5-amine.

5) Compounds having capacity for multi-site activity, for example (5.001) Bordeaux mixture, (5.002) captafol, (5.003) captan, (5.004) chlorthalonil, (5.005) copper hydroxide, (5.006) copper naphthenate, (5.007) copper oxide, (5.008) copper oxychloride, (5.009) copper(2+) sulfate, (5.010) dithianon, (5.011) dodine, (5.012) folpet, (5.013) mancozeb, (5.014) maneb, (5.015) metiram, (5.016) zinc metiram, (5.017) copper oxine, (5.018) propineb, (5.019) sulfur and sulfur preparations including calcium polysulfide, (5.020) thiram, (5.021) zineb, (5.022) ziram, (5.023) 6-ethyl-5,7-dioxo-6,7-dihydro-5H-pyrrolo[3',4':5,6][1,4]dithiino[2,3-c][1,2]thiazole-3-carbonitrile.

6) Compounds capable of triggering host defence, for example (6.001) acibenzolar-S-methyl, (6.002) isotianil, (6.003) probenazole, (6.004) tiadinil.

7) Amino acid and/or protein biosynthesis inhibitors, for example (7.001) cyprodinil, (7.002) kasugamycin, (7.003) kasugamycin hydrochloride hydrate, (7.004) oxytetracycline, (7.005) pyrimethanil, (7.006) 3-(5-fluoro-3,3,4,4-tetramethyl-3,4-dihydroisoquinolin-1-yl)quinoline.

8) ATP production inhibitors, for example (8.001) silthiofam.

9) Cell wall synthesis inhibitors, for example (9.001) benthiavalicarb, (9.002) dimethomorph, (9.003) flumorph, (9.004) iprovalicarb, (9.005) mandipropamid, (9.006) pyrimorph, (9.007) valifenalate, (9.008) (2E)-3-(4-tert-butylphenyl)-3-(2-chloropyridin-4-yl)-1-(morpholin-4-yl)prop-2-en-1-one, (9.009) (2Z)-3-(4-tert-butylphenyl)-3-(2-chloropyridin-4-yl)-1-(morpholin-4-yl)prop-2-en-1-one.

10) Lipid and membrane synthesis inhibitors, for example (10.001) propamocarb, (10.002) propamocarb hydrochloride, (10.003) tolclofos-methyl.

11) Melanin biosynthesis inhibitors, for example (11.001) tricyclazole, (11.002) 2,2,2-trifluoroethyl {3-methyl-1-[(4-methylbenzoyl)amino]butan-2-yl}carbamate.

12) Nucleic acid synthesis inhibitors, for example (12.001) benalaxyl, (12.002) benalaxyl-M (kiralaxyl), (12.003) metalaxyl, (12.004) metalaxyl-M (mefenoxam).

13) Signal transduction inhibitors, for example (13.001) fludioxonil, (13.002) iprodione, (13.003) procymidone, (13.004) proquinazid, (13.005) quinoxyfen, (13.006) vinclozolin.

14) Compounds that can act as uncouplers, for example (14.001) fluazinam, (14.002) meptyldinocap.

15) Further compounds, for example (15.001) abscisic acid, (15.002) benthiazole, (15.003) bethoxazin, (15.004) capsimycin, (15.005) carvone, (15.006) chinomethionat, (15.007) cufraneb, (15.008) cyflufenamid, (15.009) cymoxanil, (15.010) cyprosulfamide, (15.011) flutianil, (15.012) fosetyl-aluminium, (15.013) fosetyl-calcium, (15.014) fosetyl-sodium, (15.015) methyl isothiocyanate, (15.016) metrafenon, (15.017) mildiomycin, (15.018) natamycin, (15.019) nickel dimethyldithiocarbamate, (15.020) nitrothal-isopropyl, (15.021) oxamocarb, (15.022) oxathiapiprolin, (15.023) oxyfenthiin, (15.024) pentachlorophenol and salts, (15.025) phosphonic acid and salts thereof, (15.026) propamocarb-fosetylate, (15.027) pyriofenone (chlazafenone) (15.028) tebufloquin, (15.029) tecloftalam, (15.030) tolnifanide, (15.031) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.032) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.033) 2-(6-benzylpyridin-2-yl)quinazoline, (15.034) 2,6-dimethyl-1H,5H-[1,4]dithiino[2,3-c:5,6-c]dipyrrole-1,3,5,7(2H,6H)-tetrone, (15.035) 2-[3,5- bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, (15.036) 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, (15.037) 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.038) 2-[6-(3-fluoro-4-methoxyphenyl)-5-methylpyridin-2-yl]quinazoline, (15.039) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.040) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl]-3-chlorophenyl methanesulfonate, (15.041) 2-{2-[(7,8-difluoro-2-methylquinolin-3-yl)oxy]-6-fluorophenyl}propan-2-ol, (15.042) 2-{2-fluoro-6-[(8-fluoro-2-methylquinolin-3-yl)oxy]phenyl}propan-2-ol, (15.043) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl]-3-chlorophenyl methanesulfonate, (15.044) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl]phenyl methanesulfonate, (15.045) 2-phenylphenol and salts thereof, (15.046) 3-(4,4,5-trifluoro-3,3-dimethyl-3,4-dihydroisoquinolin-1-yl)quinoline, (15.047) 3-(4,4-difluoro-3,3-dimethyl-3,4-dihydroisoquinolin-1-yl)quinoline, (15.048) 4-amino-5-fluoropyrimidin-2-ol (tautomeric form: 4-amino-5-fluoropyrimidin-2(1H)-one), (15.049) 4-oxo-4-[(2-phenylethyl)amino]butyric acid, (15.050) 5-amino-1,3,4-thiadiazole-2-thiol, (15.051) 5-chloro-N'-phenyl-N'-(prop-2-yn-1-yl)thiophene 2-sulfonohydrazide, (15.052) 5-fluoro-2-[(4-fluorobenzyl)oxy]pyrimidin-4-amine, (15.053) 5-fluoro-2-[(4-methylbenzyl)oxy]pyrimidin-4-amine, (15.054) 9-fluoro-2,2-dimethyl-5-(quinolin-3-yl)-2,3-dihydro-1,4-benzoxazepine, (15.055) but-3-yn-1-yl {6-[({[(Z)-(1-methyl-1H-tetrazol-5-yl)(phenyl)methylene]amino}oxy)methyl]pyridin-2-yl}carbamate, (15.056) ethyl (2Z)-3-amino-2-cyano-3-phenylacrylate, (15.057) phenazine-1-carboxylic acid, (15.058) propyl 3,4,5-trihydroxybenzoate, (15.059) quinolin-8-ol, (15.060) quinolin-8-ol sulfate (2:1), (15.061) tert-butyl 16-[({[(1-methyl-1H-tetrazol-5-yl)(phenyl)methylene]amino}oxy)methyl]pyridin-2-yl}carbamate, (15.062) 5-fluoro-4-imino-3-methyl-1-[(4-methylphenyl)sulfonyl]-3,4-dihydropyrimidin-2 (1H)-one.

Biological Pesticides as Mixture Components

The compounds of formula (I) can be combined with biological pesticides.

Biological pesticides especially include bacteria, fungi, yeasts, plant extracts and products formed by microorganisms, including proteins and secondary metabolites.

Biological pesticides include bacteria such as spore-forming bacteria, root-colonizing bacteria and bacteria which act as biological insecticides, fungicides or nematicides.

Examples of such bacteria which are used or can be used as biological pesticides are:

*Bacillus amyloliquefaciens*, strain FZB42 (DSM 231179), or *Bacillus cereus*, in particular *B. cereus* strain CNCM I-1562 or *Bacillus fimius*, strain I-1582 (Accession number CNCM I-1582) or *Bacillus pumilus*, in particular strain GB34 (Accession No. ATCC 700814) and strain QST2808 (Accession No. NRRL B-30087), or *Bacillus subtilis*, in particular strain GB03 (Accession No. ATCC SD-1397), or *Bacillus subtilis* strain QST713 (Accession No. NRRL B-21661) or *Bacillus subtilis* strain OST 30002 (Accession No. NRRL B-50421), *Bacillus thuringiensis*, in particular *B. thuringiensis* subspecies *israelensis* (Serotyp H-14), strain AM65-52 (Accession No. ATCC 1276), or *B. thuringiensis* subsp. *aizawai*, in particular strain ABTS-1857 (SD-1372), or *B. thuringiensis* subsp. *kurstaki* strain HD-1, or *B. thuringiensis* subsp. *tenebrionis* strain NB 176 (SD-5428), *Pasteuria penetrans, Pasteuria* spp. (*Rotylenchulus reniformis* nematode)-PR3 (Accession Number ATCC SD-5834), *Streptomyces microflavus* strain AQ6121 (=QRD 31.013, NRRL B-50550), *Streptomyces galbus* strain AQ 6047 (Accession Number NRRL 30232).

Examples of fungi and yeasts which are used or can be used as biological pesticides are:

*Beauveria bassiana*, in particular strain ATCC 74040, *Coniothyrium minitans*, in particular strain CON/M/91-8 (Accession No. DSM-9660), *Lecanicillium* spp., in particular strain HRO LEC 12, *Lecanicillium lecanii* (formerly known as *Verticillium lecanii*), in particular strain KV01, *Metarhizium anisopliae*, in particular strain F52 (DSM3884/ATCC 90448), *Metschnikowia fructicola*, in particular strain NRRL Y-30752, *Paecilomyces fumosoroseus* (new: *Isaria fumosorosea*), in particular strain IFPC 200613, or strain Apopka 97 (Accession No. ATCC 20874), *Paecilomyces lilacinus*, in particular *P. lilacinus* strain 251 (AGAL 89/030550), *Talaromyces flavus*, in particular strain V117b, *Trichoderma atroviride*, in particular strain SC1 (Accession Number CBS 122089), *Trichoderma harzianum*, in particular *T. harzianum rifai* T39 (Accession Number CNCM I-952).

Examples of viruses which are used or can be used as biological pesticides are:

*Adoxophyes orana* (summer fruit tortrix) granulosis virus (GV), *Cydia pomonella* (codling moth) granulosis virus (GV), *Helicoverpa amiigera* (cotton bollworm) nuclear polyhedrosis virus (NPV), *Spodoptera exigua* (beet armyworm) mNPV, *Spodoptera frugiperda* (fall armyworm) mNPV, *Spodoptera littoralis* (African cotton leafworm) NPV.

Also included are bacteria and fungi which are added as 'inoculant' to plants or plant parts or plant organs and which, by virtue of their particular properties, promote plant growth and plant health. Examples which may be mentioned are:

*Agrobacterium* spp., *Azorhizobium caulinodans, Azospirillum* spp., *Azotobacter* spp., *Bradyrhizobium* spp., *Burkholderia* spp., especially *Burkholderia cepacia* (formerly known as *Pseudomonas cepacia*), *Gigaspora* spp., or *Gigaspora monosporum, Glomus* spp., *Laccaria* spp., *Lactobacillus buchneri, Paraglomus* spp., *Pisolithus tinctorus, Pseudomonas* spp., *Rhizobium* spp., especially *Rhizobium trifolii, Rhizopogon* spp., *Scleroderma* spp., *Suillus* spp., *Streptomyces* spp.

Examples of plant extracts and products formed by microorganisms, including proteins and secondary metabolites, which are used or can be used as biological pesticides are:

*Allium sativum, Artemisia absinthium*, azadirachtin, Biokeeper WP, *Cassia nigricans, Celastrus angulatus, Chenopodium anthelminticum*, chitin, Armour-Zen, *Dryopteris filix-mas, Equisetum arvense*, Fortune Aza, Fungastop, Heads Up (*Chenopodium quinoa* saponin extract), pyrethrum/pyrethrins, *Quassia amara*, Quercus, Quillaja, Regalia, "Requiem™ Insecticide", rotenone, ryania/ryanodine, *Symphytum officinale, Tanacetum vulgare*, thymol, Triact 70, TriCon, *Tropaeulum majus, Urtica dioica*, Veratrin, *Viscum album*, Brassicaceae extract, especially oilseed rape powder or mustard powder.

Safeners as Mixture Components

The compounds of formula (I) can be combined with safeners, for example benoxacor, cloquintocet (-mexyl), cyometrinil, cyprosulfamide, dichlormid, fenchlorazole (-ethyl), fenclorim, flurazole, fluxofenim, furilazole, isoxadifen (-ethyl), mefenpyr (-diethyl), naphthalic anhydride, oxabetrinil, 2-methoxy-N-({4-[(methylcarbamoyl)amino]phenyl}sulfonyl)benzamide (CAS 129531-12-0), 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4).

Plants and Plant Parts

All plants and plant parts can be treated in accordance with the invention. Plants are understood here to mean all plants and populations of plants, such as desirable and undesirable wild plants or crop plants (including naturally occurring crop plants), for example cereals (wheat, rice, triticale, barley, rye, oats), maize, soya beans, potatoes, sugar beet, sugar cane, tomatoes, bell peppers, cucumbers, melons, carrots, water melons, onions, lettuce, spinach, leeks, beans, *Brassica oleracea* (e.g. cabbage) and other vegetable species, cotton, tobacco, oilseed rape, and also fruit plants (the fruits being apples, pears, citrus fruits and grapes). Crop plants may be plants which can be obtained by conventional breeding and optimization methods or by biotechnological and genetic engineering methods or combinations of these methods, including the transgenic plants and including the plant cultivars which are protectable or non-protectable by plant breeders' rights. Plants shall be understood to mean all development stages such as seed, seedlings, young (immature) plants, up to and including mature plants. Plant parts shall be understood to mean all parts and organs of the plants above and below ground, such as shoot, leaf, flower and root, examples given being leaves, needles, stalks, stems, flowers, fruit bodies, fruits and seeds, and also roots, tubers and rhizomes. Plant parts also include harvested plants or harvested plant parts and vegetative and generative propagation material, for example cuttings, tubers, rhizomes, slips and seeds.

The treatment according to the invention of the plants and parts of plants with the compounds of formula (I) is effected directly or by allowing the compounds to act on the surroundings, the habitat or the storage space thereof by the customary treatment methods, for example by dipping, spraying, evaporating, fogging, scattering, painting on, injecting, and, in the case of propagation material, especially in the case of seeds, also by applying one or more coats.

As already mentioned above, it is possible to treat all plants and their parts in accordance with the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. Particular preference is given in accordance with the invention to treating plants of the respective commercially customary plant cultivars or those that are in use. Plant cultivars are understood to mean plants having new properties ("traits") and which have been obtained by conventional breeding, by mutagenesis or by recombinant DNA techniques. They may be cultivars, varieties, biotypes or genotypes.

Transgenic Plants, Seed Treatment and Integration Events

The preferred transgenic plants or plant cultivars (those obtained by genetic engineering) which are to be treated in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher harvest yields, higher quality and/or higher nutritional value of the harvested products, better capability for storage and/or processability of the harvested products. Further and particularly emphasized examples of such properties are increased resistance of the plants to animal and microbial pests, such as insects, arachnids, nematodes, mites, slugs and snails, owing, for example, to toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof), and also increased resistance of the plants to phytopathogenic fungi, bacteria and/or viruses caused, for example, by systemic acquired resistance (SAR), systemin, phytoalexins, elicitors and resistance genes and correspondingly expressed proteins and toxins, and also increased tolerance of the plants to certain active herbicidal compounds, for example imidazolinones, sulfonylureas, glyphosate or phosphinothricin (for example the "PAT" gene). The genes which impart the desired properties ("traits") in question may also be present in combinations with one another in the transgenic plants. Examples of transgenic plants mentioned include the important crop plants, such as cereals (wheat, rice, triticale, barley, rye, oats), maize, soya beans, potatoes, sugar beet, sugar cane, tomatoes, peas and other vegetable species, cotton, tobacco, oilseed rape, and also fruit plants (the fruits being apples, pears, citrus fruits and grapes), particular emphasis being given to maize, soya beans, wheat, rice, potatoes, cotton, sugar cane, tobacco and oilseed rape. Properties ("traits") which are particularly emphasized are the increased resistance of the plants to insects, arachnids, nematodes and slugs and snails.

Crop Protection Types of Treatment

The plants and plant parts are treated with the compounds of formula (I) directly or by action on their surroundings, habitat or storage space using customary treatment methods, for example by dipping, spraying, atomizing, irrigating, evaporating, dusting, fogging, broadcasting, foaming, painting, spreading, injecting, watering (drenching), drip irrigating and, in the case of propagation material, in particular in the case of seed, additionally by dry seed treatment, liquid seed treatment, slurry treatment, by incrusting, by coating with one or more coats, etc. It is furthermore possible to apply the compounds of formula (I) by the ultra-low volume method or to inject the application form or the compound of formula (I) itself into the soil.

A preferred direct treatment of the plants is foliar application, meaning that the compounds of formula (I) are applied to the foliage, in which case the treatment frequency and the application rate should be adjusted according to the level of infestation with the pest in question.

In the case of systemically active active compounds, the compounds of formula (I) also access the plants via the root system. The plants are then treated by the action of the compounds of formula (I) on the habitat of the plant. This can be accomplished, for example, by drenching, or by mixing into the soil or the nutrient solution, meaning that the locus of the plant (e.g. soil or hydroponic systems) is impregnated with a liquid form of the compounds of formula (I), or by soil application, meaning that the compounds of formula (I) according to the invention are introduced in solid form (e.g. in the form of granules) into the locus of the plants. In the case of paddy rice crops, this can also be accomplished by metering the compound of formula (I) in a solid application form (for example as granules) into a flooded paddy field.

Seed Treatment

The control of animal pests by the treatment of the seed of plants has long been known and is the subject of constant improvements. Nevertheless, the treatment of seed entails a series of problems which cannot always be solved in a satisfactory manner. Thus, it is desirable to develop methods for protecting the seed and the germinating plant which dispense with, or at least reduce considerably, the additional application of pesticides during storage, after sowing or after emergence of the plants. It is additionally desirable to optimize the amount of active compound used so as to provide optimum protection for the seed and the germinating plant from attack by animal pests, but without damage to the plant itself by the active compound used. In particular, methods for the treatment of seed should also take account of the intrinsic insecticidal or nematicidal properties of pest-resistant or -tolerant transgenic plants in order to achieve optimal protection of the seed and also the germinating plant with a minimum expenditure on pesticides. The present invention therefore in particular also relates to a method for the protection of seed and germinating plants from attack by pests, by treating the seed with one of the compounds of formula (I). The method according to the invention for protecting seed and germinating plants against attack by pests further comprises a method in which the seed is treated simultaneously in one operation or sequentially with a compound of formula (I) and a mixing component. It further also comprises a method where the seed is treated at different times with a compound of formula (I) and a mixing component.

The invention likewise relates to the use of the compounds of formula (I) for the treatment of seed for protecting the seed and the resulting plant from animal pests.

The invention further relates to seed which has been treated with a compound of formula (I) according to the invention for protection from animal pests. The invention also relates to seed which has been treated simultaneously with a compound of formula (I) and a mixing component. The invention further relates to seed which has been treated at different times with a compound of formula (I) and a mixing component. In the case of seed which has been treated at different times with a compound of formula (I) and a mixing component, the individual substances may be present on the seed in different layers. In this case, the layers comprising a compound of formula (I) and mixing components may optionally be separated by an intermediate layer. The invention also relates to seed in which a compound of formula (I) and a mixing component have been applied as part of a coating or as a further layer or further layers in addition to a coating.

The invention further relates to seed which, after the treatment with a compound of formula (I), is subjected to a film-coating process to prevent dust abrasion on the seed.

One of the advantages that occur when a compound of formula (I) acts systemically is that the treatment of the seed protects not only the seed itself but also the plants resulting therefrom, after emergence, from animal pests. In this way, the immediate treatment of the crop at the time of sowing or shortly thereafter can be dispensed with.

A further advantage is that the treatment of the seed with a compound of formula (I) can enhance germination and emergence of the treated seed.

It is likewise considered to be advantageous that compounds of formula (I) can especially also be used for transgenic seed.

Furthermore, compounds of formula (I) can be employed in combination with compositions of signalling technology, leading to better colonization by symbionts such as, for example, *rhizobia*, mycorrhizae and/or endophytic bacteria or fungi, and/or to optimized nitrogen fixation.

The compounds of formula (I) are suitable for the protection of seed of any plant variety which is used in agriculture, in greenhouses, in forests or in horticulture. More particularly, this is the seed of cereals (for example wheat, barley, rye, millet and oats), maize, cotton, soya beans, rice, potatoes, sunflowers, coffee, tobacco, canola, oilseed rape, beets (for example sugar beets and fodder beets), peanuts, vegetables (for example tomatoes, cucumbers, beans, cruciferous vegetables, onions and lettuce), fruit plants, lawns and ornamental plants. Of particular significance is the treatment of the seed of cereals (such as wheat, barley, rye and oats), maize, soya beans, cotton, canola, oilseed rape, vegetables and rice.

As already mentioned above, the treatment of transgenic seed with a compound of formula (I) is also of particular importance. This involves the seed of plants which generally contain at least one heterologous gene which controls the expression of a polypeptide having insecticidal and/or nematicidal properties in particular. The heterologous genes in transgenic seed may originate from microorganisms such as *Bacillus*, *Rhizobium*, *Pseudomonas*, *Serratia*, *Trichoderma*, *Clavibacter*, *Glomus* or *Gliocladium*. The present invention is particularly suitable for treatment of transgenic seed which comprises at least one heterologous gene originating from *Bacillus* sp. The heterologous gene is more preferably derived from *Bacillus thuringiensis*.

In the context of the present invention, the compound of formula (I) is applied to the seed. The seed is preferably treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content which allows storage. Alternatively, it is also possible to use seed which, after drying, has been treated with, for example, water and then dried again, for example priming. In the case of rice seed, it is also possible to use seed which has been soaked, for example in water, until it reaches a certain stage of the rice embryo ("pigeon breast stage") which results in stimulation of germination and more uniform emergence.

When treating the seed, care must generally be taken that the amount of the compound of formula (I) applied to the seed and/or the amount of further additives is chosen in such a way that the germination of the seed is not adversely affected, or that the resulting plant is not damaged. This has to be ensured particularly in the case of active compounds which can exhibit phytotoxic effects at certain application rates.

In general, the compounds of formula (I) are applied to the seed in the form of a suitable formulation. Suitable formulations and processes for seed treatment are known to the person skilled in the art.

The compounds of formula (I) can be converted to the customary seed-dressing formulations, such as solutions, emulsions, suspensions, powders, foams, slurries or other coating compositions for seed, and also ULV formulations.

These formulations are prepared in a known manner, by mixing the compounds of formula (I) with customary additives, for example customary extenders and solvents or diluents, dyes, wetting agents, dispersants, emulsifiers, antifoams, preservatives, secondary thickeners, adhesives, gibberellins, and also water.

Dyes which may be present in the seed-dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed-dressing formulations usable in accordance with the invention are all substances which promote wetting and which are customary for the formulation of agrochemically active compounds. Usable with preference are alkyl naphthalenesulfonates, such as diisopropyl or diisobutyl naphthalenesulfonates.

Suitable dispersants and/or emulsifiers which may be present in the seed-dressing formulations usable in accordance with the invention are all nonionic, anionic and cationic dispersants customary for the formulation of agrochemically active compounds. Nonionic or anionic dispersants or mixtures of nonionic or anionic dispersants can be used with preference. Suitable nonionic dispersants especially include ethylene oxide/propylene oxide block polymers, alkylphenol polyglycol ethers and tristyrylphenol polyglycol ethers, and the phosphated or sulfated derivatives thereof. Suitable anionic dispersants are especially lignosulfonates, polyacrylic acid salts and arylsulfonate-formaldehyde condensates.

Antifoams which may be present in the seed-dressing formulations usable in accordance with the invention are all foam-inhibiting substances customary for the formulation of agrochemically active compounds. Silicone antifoams and magnesium stearate can be used with preference.

Preservatives which may be present in the seed-dressing formulations usable in accordance with the invention are all substances usable for such purposes in agrochemical compositions. Examples include dichlorophene and benzyl alcohol hemiformal.

Secondary thickeners which may be present in the seed-dressing formulations usable in accordance with the invention are all substances which can be used for such purposes in agrochemical compositions. Preferred examples include cellulose derivatives, acrylic acid derivatives, xanthan, modified clays and finely divided silica.

Useful stickers which may be present in the seed-dressing formulations usable in accordance with the invention are all customary binders usable in seed-dressing products. Preferred examples include polyvinylpyrrolidone, polyvinyl acetate, polyvinyl alcohol and tylose.

Gibberellins which may be present in the seed-dressing formulations usable in accordance with the invention are preferably the gibberellins A1, A3 (=gibberellic acid), A4 and A7; particular preference is given to using gibberellic acid. The gibberellins are known (cf. R. Wegler "Chemie der Pflanzenschutz-und Schadlingsbekampfungsmittel", vol. 2, Springer Verlag, 1970, pp. 401-412).

The seed-dressing formulations usable in accordance with the invention can be used to treat a wide variety of different kinds of seed, either directly or after prior dilution with water. For instance, the concentrates or the preparations obtainable therefrom by dilution with water can be used to dress the seed of cereals, such as wheat, barley, rye, oats and triticale, and also the seed of maize, rice, oilseed rape, peas, beans, cotton, sunflowers, soya beans and beets, or else a wide variety of different vegetable seed. The seed-dressing formulations usable in accordance with the invention, or the dilute use forms thereof, can also be used to dress seed of transgenic plants.

For the treatment of seed with the seed-dressing formulations usable in accordance with the invention, or the use forms prepared therefrom through the addition of water, all mixing units usable customarily for the seed dressing are useful. Specifically, the procedure in seed dressing is to place the seed into a mixer in batchwise or continuous operation, to add the particular desired amount of seed-dressing formulations, either as such or after prior dilution with water, and to mix until the formulation is distributed homogeneously on the seed. If appropriate, this is followed by a drying operation.

The application rate of the seed dressing formulations usable in accordance with the invention can be varied within a relatively wide range. It is guided by the particular content of the compounds of formula (I) in the formulations and by the seed. The application rates of the compound of formula (I) are generally between 0.001 and 50 g per kilogram of seed, preferably between 0.01 and 15 g per kilogram of seed.

Animal Health

In the animal health field, i.e. the field of veterinary medicine, the compounds of formula (I) are active against animal parasites, in particular ectoparasites or endoparasites. The term "endoparasite" includes especially helminths and protozoa, such as coccidia. Ectoparasites are typically and preferably arthropods, especially insects or acarids.

In the field of veterinary medicine, the compounds of formula (I) having favourable endotherm toxicity are suitable for controlling parasites which occur in animal breeding and animal husbandry in livestock, breeding animals, zoo animals, laboratory animals, experimental animals and domestic animals. They are active against all or specific stages of development of the parasites.

Agricultural livestock include, for example, mammals, such as sheep, goats, horses, donkeys, camels, buffalo, rabbits, reindeer, fallow deer and especially cattle and pigs; or poultry such as turkeys, ducks, geese and especially chickens; or fish or crustaceans, for example in aquaculture; or, as the case may be, insects such as bees.

Domestic animals include, for example, mammals, such as hamsters, guinea pigs, rats, mice, chinchillas, ferrets, and particularly dogs, cats, caged birds; reptiles, amphibians or aquarium fish.

In a specific embodiment, the compounds of formula (I) are administered to mammals.

In another specific embodiment, the compounds of formula (I) are administered to birds, namely caged birds or particularly poultry.

Use of the compounds of formula (I) for the control of animal parasites is intended to reduce or prevent illness, cases of death and reductions in performance (in the case of meat, milk, wool, hides, eggs, honey and the like), such that more economical and simpler animal husbandry is enabled and better animal well-being is achievable.

In relation to the field of animal health, the term "control" or "controlling" in the present context means that the compounds of formula (I) are effective in reducing the incidence of the particular parasite in an animal infected with such parasites to an innocuous degree. More specifically, "controlling" in the present context means that the compounds of formula (I) kill the respective parasite, inhibit its growth, or inhibit its proliferation.

The arthropods include, for example, but are not limited to, from the order of Anoplurida, for example, *Haematopinus* spp., *Linognathus* spp., *Pediculus* spp., *Phtirus* spp. and *Solenopotes* spp.;

from the order of Mallophagida and the suborders Amblycerina and Ischnocerina, for example, *Bovicola* spp., *Damalina* spp., *Felicola* spp.; *Lepikentron* spp., *Menopon* spp., *Trichodectes* spp., *Trimenopon* spp., *Trinoton* spp., *Werneckiella* spp;

from the order of Diptera and the suborders Nematocerina and Brachycerina, for example, *Aedes* spp., *Anopheles* spp., *Atylotus* spp., *Braula* spp., *Calliphora* spp., *Chrysomyia* spp., *Chrysops* spp., *Culex* spp., *Culicoides* spp., *Eusimulium* spp., *Fannia* spp., *Gasterophilus* spp., *Glossina* spp., *Haematobia* spp., *Haematopota* spp., *Hippobosca* spp., *Hybomitra* spp., *Hydrotaea* spp., *Hypoderma* spp., *Lipoptena* spp., *Lucilia* spp., *Lutzomyia* spp., *Melophagus* spp., *Morellia* spp., *Musca* spp., *Odagmia* spp., *Oestrus* spp., *Philipomyia* spp., *Phlebotomus* spp., *Rhinoestrus* spp., *Sarcophaga* spp., *Simulium* spp., *Stomoxys* spp., *Tabanus* spp., *Tipula* spp., *Wilhelmia* spp., *Wohlfahrtia* spp.;

from the order of Siphonapterida, for example, *Ceratophyllus* spp., *Ctenocephalides* spp., *Pulex* spp., *Tunga* spp., *Xenopsylla* spp.;

from the order of Heteropterida, for example *Cimex* spp., *Panstrongylus* spp., *Rhodnius* spp., *Triatoma* spp.; and also nuisance and hygiene pests from the order Blattarida.

In addition, in the case of the arthropods, mention should be made by way of example, without limitation, of the following Acari:

from the subclass of Acari (Acarina) and the order of Metastigmata, for example from the family of Argasidae such as *Argas* spp., *Ornithodorus* spp., *Otobius* spp., from the family of Ixodidae such as *Amblyomma* spp., *Dermacentor* spp., *Haemaphysalis* spp., *Hyalomma* spp., *Ixodes* spp., *Rhipicephalus (Boophilus)* spp., *Rhipicephalus* spp. (the original genus of multi-host ticks); from the order of Mesostigmata such as *Dermanyssus* spp., *Ornithonyssus* spp., *Pneumonyssus* spp., *Raillietia* spp., *Sternostoma* spp., *Tropilaelaps* spp., *Varroa* spp.; from the order of the Actinedida (Prostigmata), for example *Acarapis* spp., *Cheyletiella* spp., *Demodex* spp., *Listrophorus* spp., *Myobia* spp., *Neotrombicula* spp., *Ornithocheyletia* spp., *Psorergates* spp., *Trombicula* spp.; and from the order of the Acaridida (Astigmata), for example *Acarus* spp., *Caloglyphus* spp., *Chorioptes* spp., *Cytodites* spp., *Hypodectes* spp., *Knemidocoptes* spp., *Laminosioptes* spp., *Notoedres* spp., *Otodectes* spp., *Psoroptes* spp., *Pterolichus* spp., *Sarcoptes* spp., *Trixacarus* spp., *Tyrophagus* spp.

Examples of parasitic protozoa include, but are not limited to:

Mastigophora (*Flagellata*), such as:

Metamonada: from the order of Diplomonadida, for example *Giardia* spp., *Spironucleus* spp.

Parabasala: from the order of Trichomonadida, for example *Histomonas* spp., *Pentatrichomonas* spp., *Tetratrichomonas* spp., *Trichomonas* spp., *Tritrichomonas* spp.

Euglenozoa: from the order of Trypanosomatida, for example *Leishmania* spp., *Trypanosoma* spp.

Sarcomastigophora (Rhizopoda) such as Entamoebidae, for example *Entamoeba* spp., Centramoebidae, for example *Acanthamoeba* sp., Euamoebidae, e.g. *Hartmanella* sp.

Alveolata such as Apicomplexa (Sporozoa): e.g. *Cryptosporidium* spp.; from the order of Eimeriida, for example, *Besnoitia* spp., *Cystoisospora* spp., *Eimeria* spp., *Hammondia* spp., *Isospora* spp., *Neospora* spp., *Sarcocystis* spp., *Toxoplasma* spp.; from the order of Adeleida, for example, *Hepatozoon* spp., *Klossiella* spp.; from the order of Haemosporida, for example, *Leucocytozoon* spp., *Plasmodium* spp.; from the order of Piroplasmida, for example, *Babesia* spp., *Ciliophora* spp., *Echinozoon* spp., *Theileria* spp.; from the order of Vesibuliferida, for example, *Balantidium* spp., *Buxtonella* spp.

Microspora such as *Encephalitozoon* spp., *Enterocytozoon* spp., *Globidium* spp., *Nosema* spp., and also, for example, *Myxozoa* spp.

The helminths that are pathogenic to humans or animals include, for example, Acanthocephala, nematodes, Pentastoma and Platyhelminths (e.g. Monogenea, cestodes and trematodes).

Exemplary helminths include, but are not limited to:

Monogenea: e.g. *Dactylogyrus* spp., *Gyrodactylus* spp., *Microbothrium* spp., *Polystoma* spp., *Troglecephalus* spp.;

Cestodes: from the order of Pseudophyllidea, for example: *Bothridium* spp., *Diphyllobothrium* spp., *Diplogonoporus* spp., *Ichthyobothrium* spp., *Ligula* spp., *Schistocephalus* spp., *Spirometra* spp.

From the order of Cyclophyllida, for example: *Andyra* spp., *Anoplocephala* spp., *Avitellina* spp., *Bertiella* spp., *Cittotaenia* spp., *Davainea* spp., *Diorchis* spp., *Diplopylidium* spp., *Dipylidium* spp., *Echinococcus* spp., *Echinocotyle* spp., *Echinolepis* spp., *Hydatigera* spp., *Hymenolepis* spp., *Joyeuxiella* spp., *Mesocestoides* spp., *Moniezia* spp., *Paranoplocephala* spp., *Raillietina* spp., *Stilesia* spp., *Taenia* spp., *Thysaniezia* spp., *Thysanosoma* spp.

Trematodes: from the class of Digenea, for example: *Austrobilharzia* spp., *Brachylaima* spp., *Calicophoron* spp., *Catatropis* spp., *Clonorchis* spp. *Collyriclum* spp., *Cotylophoron* spp., *Cyclocoelum* spp., *Dicrocoelium* spp., *Diplostomum* spp., *Echinochasmus* spp., *Echinoparyphium* spp., *Echinostoma* spp., *Eurytrema* spp., *Fasciola* spp., *Fasciolides* spp., *Fasciolopsis* spp., *Fischoederius* spp., *Gastrothylacus* spp., *Gigantobilharzia* spp., *Gigantocotyle* spp., *Heterophyes* spp., *Hypoderaeum* spp., *Leucochloridium* spp., *Metagonimus* spp., *Metorchis* spp., *Nanophyetus* spp., *Notocotylus* spp., *Opisthorchis* spp., *Ornithobilharzia* spp., *Paragonimus* spp., *Paramphistomum* spp., *Plagiorchis* spp., *Posthodiplostomum* spp., *Prosthogonimus* spp., *Schistosoma* spp., *Trichobilharzia* spp., *Troglotrema* spp., *Typhlocoelum* spp.

Nematodes: from the order of Trichinellida, for example: *Capillaria* spp., *Trichinella* spp., *Trichomosoides* spp., *Trichuris* spp.

From the order of Tylenchida, for example: *Micronema* spp., *Parastrangyloides* spp., *Strongyloides* spp.

From the order of Rhabditina, for example: *Aelurostrongylus* spp., *Amidostomum* spp., *Ancylostoma* spp., *Angiostrongylus* spp., *Bronchonema* spp., *Bunostomum* spp., *Chabertia* spp., *Cooperia* spp., *Cooperioides* spp., *Crenosoma* spp., *Cyathostomum* spp., *Cyclococercus* spp., *Cyclodontostomum* spp., *Cylicocyclus* spp., *Cylicostephanus* spp., *Cylindropharynx* spp., *Cystocaulus* spp., *Dictyocaulus* spp., *Elaphostrongylus* spp., *Filaroides* spp., *Globocephalus* spp., *Graphidium* spp., *Gyalocephalus* spp., *Haemonchus* spp.,

*Heligmosomoides* spp., *Hyostrongylus* spp., *Marshallagia* spp., *Metastrongylus* spp., *Muellerius* spp., *Necator* spp., *Nematodirus* spp., *Neostrongylus* spp., *Nippostrongylus* spp., *Obeliscoides* spp., *Oesophagodontus* spp., *Oesophagostomum* spp., *Ollulanus* spp.; *Ornithostrongylus* spp., *Oslerus* spp., *Ostertagia* spp., *Paracooperia* spp., *Paracrenosoma* spp., *Parafilaroides* spp., *Parelaphostrongylus* spp., *Pneumocaulus* spp., *Pneumostrongylus* spp., *Poteriostomum* spp., *Protostrongylus* spp., *Spicocaulus* spp., *Stephanurus* spp., *Strongylus* spp., *Syngamus* spp., *Teladorsagia* spp., *Trichonema* spp., *Trichostrongylus* spp., *Triodontophorus* spp., *Troglostrongylus* spp., *Uncinaria* spp.

From the order of Spirurida, for example: *Acanthocheilonema* spp., *Anisakis* spp., *Ascaridia* spp.; *Ascaris* spp., *Ascarops* spp., *Aspiculuris* spp., *Baylisascaris* spp., *Brugia* spp., *Cercopithifilaria* spp., *Crassicauda* spp., *Dipetalonema* spp., *Dirofilaria* spp., *Dracunculus* spp.; *Draschia* spp., *Enterobius* spp., *Filaria* spp., *Gnathostoma* spp., *Gongylonema* spp., *Habronema* spp., *Heterakis* spp.; *Litomosoides* spp., *Loa* spp., *Onchocerca* spp., *Oxyuris* spp., *Parabronema* spp., *Parafilaria* spp., *Parascaris* spp., *Passalurus* spp., *Physaloptera* spp., *Probstmayria* spp., *Pseudofilaria* spp., *Setaria* spp., *Skjrabinema* spp., *Spirocerca* spp., *Stephanofilaria* spp., *Strongyluris* spp., *Syphacia* spp., *Thelazia* spp., *Toxascaris* spp., *Toxocara* spp., *Wuchereria* spp.

Acanthocephala: from the order of Oligacanthorhynchida, for example: *Macracanthorhynchus* spp., *Prosthenorchis* spp.; from the order of Moniliformida, for example: *Moniliformis* spp.

From the order of Polymorphida, for example: *Filicollis* spp.; from the order of Echinorhynchida, for example *Acanthocephalus* spp., *Echinorhynchus* spp., *Leptorhynchoides* spp.

Pentastoma: from the order of Porocephalida, for example *Linguatula* spp.

In the veterinary field and in animal husbandry, the compounds of formula (I) are administered by methods generally known in the art, such as via the enteral, parenteral, dermal or nasal route in the form of suitable preparations. Administration may be prophylactic, metaphylactic or therapeutic.

Thus, one embodiment of the present invention refers to the compounds of formula (I) for use as a medicament.

A further aspect relates to the compounds of formula (I) for use as an antiendoparasitic agent.

A further specific aspect of the invention relates to the compounds of formula (I) for use as an antihelminthic agent, especially for use as a nematicide, platyhelminthicide, acanthocephalicide or pentastomicide.

A further specific aspect of the invention relates to the compounds of formula (I) for use as an antiprotozoic agent.

A further aspect relates to the compounds of formula (I) for use as an antiectoparasitic agent, especially an arthropodicide, very particularly an insecticide or an acaricide.

Further aspects of the invention are veterinary medicine formulations comprising an effective amount of at least one compound of formula (I) and at least one of the following: a pharmaceutically acceptable excipient (e.g. solid or liquid diluents), a pharmaceutically acceptable auxiliary (e.g. surfactants), especially a pharmaceutically acceptable excipient used conventionally in veterinary medicine formulations and/or a pharmaceutically acceptable auxiliary conventionally used in veterinary medicine formulations.

A related aspect of the invention is a method for production of a veterinary medicine formulation as described here, which comprises the step of mixing at least one compound of formula (I) with pharmaceutically acceptable excipients and/or auxiliaries, especially with pharmaceutically acceptable excipients used conventionally in veterinary medicine formulations and/or auxiliaries used conventionally in veterinary medicine formulations.

Another specific aspect of the invention is veterinary medicine formulations selected from the group of ectoparasiticidal and endoparasiticidal formulations, especially selected from the group of anthelmintic, antiprotozoic and arthropodicidal formulations, very particularly selected from the group of nematicidal, platyhelminthicidal, acanthocephalicidal, pentastomicidal, insecticidal and acaricidal formulations, according to the aspects mentioned, and methods for production thereof.

Another aspect relates to a method for treatment of a parasitic infection, especially an infection caused by a parasite selected from the group of the ectoparasites and endoparasites mentioned here, by use of an effective amount of a compound of formula (I) in an animal, especially a nonhuman animal, having a need therefor.

Another aspect relates to a method for treatment of a parasitic infection, especially an infection caused by a parasite selected from the group of the ectoparasites and endoparasites mentioned here, by use of a veterinary medicine formulation as defined here in an animal, especially a nonhuman animal, having a need therefor.

Another aspect relates to the use of the compounds of formula (I) in the treatment of a parasite infection, especially an infection caused by a parasite selected from the group of the ectoparasites and endoparasites mentioned here, in an animal, especially a nonhuman animal.

In the present context of animal health or veterinary medicine, the term "treatment" includes prophylactic, metaphylactic and therapeutic treatment.

In a particular embodiment, in this way, mixtures of at least one compound of formula (I) with other active compounds, especially with endo- and ectoparasiticides, are provided for the field of veterinary medicine.

In the field of animal health, "mixture" means not just that two (or more) different active compounds are formulated in a common formulation and are correspondingly employed together, but also relates to products comprising formulations separated for each active compound. Accordingly, when more than two active compounds are to be employed, all active compounds can be formulated in a common formulation or all active compounds can be formulated in separate formulations; likewise conceivable are mixed forms in which some of the active compounds are formulated together and some of the active compounds are formulated separately. Separate formulations allow the separate or successive application of the active compounds in question.

The active compounds specified here by their common names are known and are described, for example, in the "Pesticide Manual" (see above) or can be searched for on the Internet (e.g.).

Illustrative active compounds from the group of the ectoparasiticides as mixing components, without any intention that this should constitute a restriction, include the insecticides and acaricides listed in detail above. Further usable active compounds are listed below in accordance with the abovementioned classification based on the current IRAC Mode of Action Classification Scheme: (1) acetylcholinesterase (AChE) inhibitors; (2) GABA-gated chloride channel blockers; (3) sodium channel modulators; (4) nicotinic acetylcholine receptor (nAChR) competitive modulators; (5) nicotinic acetylcholine receptor (nAChR) allosteric modulators; (6) glutamate-gated chloride channel (GluCl) allosteric modulators; (7) juvenile hormone mimetics; (8) miscellaneous non-specific (multi-site) inhibitors; (9) chordotonal organ modulators; (10) mite growth inhibitors; (12) inhibitors of mitochondrial ATP synthase, such as ATP disruptors; (13) uncouplers of oxidative phosphorylation via disruption of the proton gradient; (14) nicotinic acetylcholine receptor channel blockers; (15) inhibitors of chitin biosynthesis, type 0; (16) inhibitors of chitin biosynthesis, type 1; (17) moulting disruptors (especially in Diptera); (18) ecdysone receptor agonists; (19) octopamine receptor agonists; (21) mitochondrial complex I electron transport inhibitors; (25) mitochondrial complex II electron transport inhibitors; (20) mitochondrial complex III electron transport inhibitors; (22) voltage-dependent sodium channel blockers; (23) inhibitors of acetyl CoA carboxylase; (28) ryanodine receptor modulators;

active compounds having unknown or non-specific mechanisms of action, e.g. fentrifanil, fenoxacrim, cycloprene, chlorobenzilate, chlordimeform, flubenzimin, dicyclanil, amidoflumet, quinomethionat, triarathene, clothiazoben, tetrasul, potassium oleate, petroleum, metoxadiazone, gossyplur, flutenzine, brompropylate, cryolite;

compounds from other classes, for example butacarb, dimetilan, cloethocarb, phosphocarb, pirimiphos(-ethyl), parathion(-ethyl), methacrifos, isopropyl o-salicylate, trichlorfon, tigolaner, sulprofos, propaphos, sebufos, pyridathion, prothoate, dichlofenthion, demeton-S-methyl sulfone, isazofos, cyanofenphos, dialifos, carbophenothion, autathiofos, aromfenvinfos(-methyl), azinphos(-ethyl), chlorpyrifos(-ethyl), fosmethilan, iodofenphos, dioxabenzofos, formothion, fonofos, flupyrazofos, fensulfothion, etrimfos;

organochlorine compounds, for example camphechlor, lindane, heptachlor; or phenylpyrazoles, e.g. acetoprole, pyrafluprole, pyriprole, vaniliprole, sisapronil; or isoxazolines, e.g. sarolaner, afoxolaner, lotilaner, fluralaner;

pyrethroids, e.g. (cis-, trans-)metofluthrin, profluthrin, flufenprox, flubrocythrinate, fubfenprox, fenfluthrin, protrifenbut, pyresmethrin, RU15525, terallethrin, cis-resmethrin, heptafluthrin, bioethanomethrin, biopermethrin, fenpyrithrin, cis-cypermethrin, cis-permethrin, clocythrin, cyhalothrin (lambda-), chlovaporthrin, or halogenated hydrocarbon compounds (HCHs), neonicotinoids, e.g. nithiazine dicloromezotiaz, triflumezopyrim macrocyclic lactones, e.g. nemadectin, ivermectin, latidectin, moxidectin, selamectin, eprinomectin, doramectin, emamectin benzoate; milbemycin oxime triprene, epofenonane, diofenolan;

biologicals, hormones or pheromones, for example natural products, e.g. thuringiensin, codlemone or neem components dinitrophenols, e.g. dinocap, dinobuton, binapacryl;

benzoylureas, e.g. fluazuron, penfluron, amidine derivatives, e.g. chlormebuform, cymiazole, demiditraz beehive *varroa* acaricides, for example organic acids, e.g. formic acid, oxalic acid.

Illustrative active compounds from the group of the endoparasiticides, as mixing components, include, but are not limited to, active anthelmintic ingredients and active antiprotozoic ingredients.

The anthelmintic active compounds include but are not limited to the following nematicidally, trematicidally and/or cestocidally active compounds:

from the class of the macrocyclic lactones, for example: eprinomectin, abamectin, nemadectin, moxidectin, doramectin, selamectin, lepimectin, latidectin, milbemectin, ivermectin, emamectin, milbemycin;

from the class of the benzimidazoles and probenzimidazoles, for example: oxibendazole, mebendazole, triclabendazole, thiophanate, parbendazole, oxfendazole, netobimin, fenbendazole, febantel, thiabendazole, cyclobendazole, cambendazole, albendazole sulfoxide, albendazole, flubendazole;

from the class of the depsipeptides, preferably cyclic depsipeptides, especially 24-membered cyclic depsipeptides, for example: emodepside, PF1022A;

from the class of the tetrahydropyrimidines, for example: morantel, pyrantel, oxantel;

from the class of the imidazothiazoles, for example: butamisole, levamisole, tetramisole;

from the class of the aminophenylamidines, for example: amidantel, deacylated amidantel (dAMD), tribendimidine;

from the class of the aminoacetonitriles, for example: monepantel;

from the class of the paraherquamides, for example: paraherquamide, derquantel;

from the class of the salicylanilides, for example: tribromsalan, bromoxanide, brotianide, clioxanide, closantel, niclosamide, oxyclozanide, rafoxanide;

from the class of the substituted phenols, for example: nitroxynil, bithionol, disophenol, hexachlorophene, niclofolan, meniclopholan;

from the class of the organophosphates, for example: trichlorfon, naphthalofos, dichlorvos/DDVP, crufomate, coumaphos, haloxon;

from the class of the piperazinones/quinolines, for example: praziquantel, epsiprantel;

from the class of the piperazines, for example: piperazine, hydroxyzine;

from the class of the tetracyclines, for example: tetracycline, chlorotetracycline, doxycycline, oxytetracycline, rolitetracycline;

from various other classes, for example: bunamidine, niridazole, resorantel, omphalotin, oltipraz, nitroscanate, nitroxynil, oxamniquin, mirasan, miracil, lucanthon, hycanthon, hetolin, emetin, diethylcarbamazine, dichlorophen, diamfenetide, clonazepam, bephenium, amoscanate, clorsulon.

Active antiprotozoic compounds include, but are not limited to, the following active compounds:

from the class of the triazines, for example: diclazuril, ponazuril, letrazuril, toltrazuril;

from the class of polyether ionophores, for example: monensin, salinomycin, maduramicin, narasin;

from the class of the macrocyclic lactones, for example: milbemycin, erythromycin;

from the class of the quinolones, for example: enrofloxacin, pradofloxacin;

from the class of the quinines, for example: chloroquine;

from the class of the pyrimidines, for example: pyrimethamine;

from the class of the sulfonamides, for example: sulfaquinoxaline, trimethoprim, sulfaclozin;

from the class of the thiamines, for example: amprolium;

from the class of the lincosamides, for example: clindamycin;

from the class of the carbanilides, for example: imidocarb;

from the class of the nitrofurans, for example: nifurtimox;

from the class of the quinazolinone alkaloids, for example: halofuginone;

from various other classes, for example: oxamniquine, paromomycin;

from the class of the vaccines or antigens from microorganisms, for example: *Babesia canis rossi, Eimeria tenella, Eimeria praecox, Eimeria necatrix, Eimeria mitis, Eimeria maxima, Eimeria brunetti, Eimeria acervulina, Babesia canis vogeli, Leishmania infantum, Babesia canis canis, Dictyocaulus viviparus.*

All the mixing components mentioned, as the case may be, may also form salts with suitable bases or acids if they are capable of doing so on the basis of their functional groups.

Vector Control

The compounds of formula (I) can also be used in vector control. In the context of the present invention, a vector is an arthropod, especially an insect or arachnid, capable of transmitting pathogens, for example viruses, worms, single-cell organisms and bacteria, from a reservoir (plant, animal, human, etc.) to a host. The pathogens can be transmitted either mechanically (for example trachoma by non-stinging flies) onto a host or after injection into a host (for example malaria parasites by mosquitoes).

Examples of vectors and the diseases or pathogens they transmit are:

1) Mosquitoes
Anopheles: malaria, filariasis;
Culex: Japanese encephalitis, filariasis, other viral diseases, transmission of other worms;
Aedes: yellow fever, dengue fever, further viral disorders, filariasis;
Simuliidae: transmission of worms, especially *Onchocerca volvulus;*
Psychodidae: transmission of leishmaniasis
2) Lice: skin infections, epidemic typhus;
3) Fleas: plague, endemic typhus, tapeworms;
4) Flies: sleeping sickness (trypanosomiasis); cholera, other bacterial diseases;
5) Mites: acariosis, epidemic typhus, rickettsialpox, tularaemia, Saint Louis encephalitis, tick-borne encephalitis (TBE), Crimean-Congo haemorrhagic fever, borreliosis;
6) Ticks: borrelioses such as *Borrelia bungdorferi* sensu lato., *Borrelia duttoni,* tick-borne encephalitis, Q fever (*Coxiella burnetii*), babesioses (*Babesia canis canis*), ehrlichiosis.

Examples of vectors in the context of the present invention are insects, for example aphids, flies, leafhoppers or thrips, which can transmit plant viruses to plants. Other vectors capable of transmitting plant viruses are spider mites, lice, beetles and nematodes.

Further examples of vectors in the context of the present invention are insects and arachnids such as mosquitoes, especially of the genera *Aedes, Anopheles,* for example *A. gambiae, A. arabiensis, A. funestus, A. dirus* (malaria) and Culex, Psychodidae such as *Phlebotomus,* Lutzomyia, lice, fleas, flies, mites and ticks, which can transmit pathogens to animals and/or humans.

Vector control is also possible if the compounds of formula (I) are resistance-breaking.

Compounds of formula (I) are suitable for use in the prevention of diseases and/or pathogens transmitted by vectors. Thus, a further aspect of the present invention is the use of compounds of formula (I) for vector control, for example in agriculture, in horticulture, in forests, in gardens and in leisure facilities, and also in the protection of materials and stored products.

Protection of Industrial Materials

The compounds of formula (I) are suitable for protecting industrial materials against attack or destruction by insects, for example from the orders of Coleoptera, Hymenoptera, Isoptera, Lepidoptera, Psocoptera and Zygentoma.

Industrial materials in the present context are understood to mean inanimate materials, such as preferably plastics, adhesives, sizes, papers and cards, leather, wood, processed wood products and coating compositions. The use of the invention for protection of wood is particularly preferred.

In a further embodiment, the compounds of formula (I) are used together with at least one further insecticide and/or at least one fungicide.

In a further embodiment, the compounds of formula (I) take the form of a ready-to-use pesticide, meaning that they can be applied to the material in question without further modifications. Useful further insecticides or fungicides especially include those mentioned above.

Surprisingly, it has also been found that the compounds of formula (I) can be employed for protecting objects which come into contact with saltwater or brackish water, in particular hulls, screens, nets, buildings, moorings and signalling systems, against fouling. It is equally possible to use the compounds of formula (I), alone or in combinations with other active compounds, as antifouling agents.

Control of Animal Pests in the Hygiene Sector

The compounds of formula (I) are suitable for controlling animal pests in the hygiene sector. More particularly, the invention can be used in the domestic protection sector, in the hygiene protection sector and in the protection of stored products, particularly for control of insects, arachnids, ticks and mites encountered in enclosed spaces, for example dwellings, factory halls, offices, vehicle cabins, animal breeding facilities. For controlling animal pests, the compounds of formula (I) are used alone or in combination with other active compounds and/or auxiliaries. They are preferably used in domestic insecticide products. The compounds of formula (I) are effective against sensitive and resistant species, and against all developmental stages.

These pests include, for example, pests from the class Arachnida, from the orders Scorpiones, Araneae and Opiliones, from the classes Chilopoda and Diplopoda, from the class Insecta the order Blattodea, from the orders Coleoptera, Dermaptera, Diptera, Heteroptera, Hymenoptera, Isoptera, Lepidoptera, *Phthiraptera,* Psocoptera, Saltatoria or Orthoptera, Siphonaptera and Zygentoma and from the class Malacostraca the order Isopoda.

Application is effected, for example, in aerosols, unpressurized spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or bait stations.

PREPARATION EXAMPLES

2-[3-(Ethylsulfonyl)-7-(trifluoromethypimidazolL2-alpyridin-2-yl]-6-(trifluoromethyl)[1,2,4]triazolo[1,5-a]pyridine (I-01)

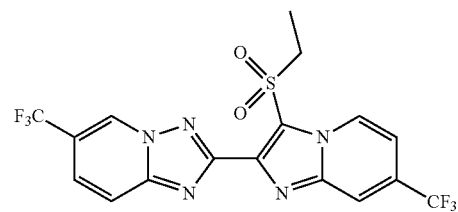 [SMILES: CCS(=O)(=O)c1c(-c2nc3ccc(C(F)(F)F)cn3n2)nc2cc(C(F)(F)F)ccn12]

A mixture of 3-(ethylsulfonyl)-7-(trifluoromethyl)imidazo[1,2-a]pyridine-2-carbonitrile (137 mg, 0.45 mmol), 5-(trifluoromethyl)pyridine-2-amine (87.9 mg, 0.54 mmol), CuBr (6.5 mg, 0.045 mmol), 1,10-phenanthroline (8.1 mg, 0.045 mmol) and ZnI$_2$ (28.8 mg, 0.090 mmol) in 1,2-dichlorobenzene was stirred at 130° C. for 3 days. The solvent was removed at 75° C. under reduced pressure and the residue was taken up in cyclohexane. The solid was filtered off with suction and purified by column chromatography purification by preparative HPLC using a water/acetonitrile gradient as mobile phase.

log P (neutral): 2.41; MH$^+$: 464; $^1$H-NMR (400 MHz, D$_6$-DMSO) δ ppm: 1.34 (t, 3H), 4.03 (q, 2H), 8.07 (dd, 1H), 8.19 (d, 1H), 8.48 (s, 1H), 9.28 (d, 1H), 9.85 (s, 1H).

3-(Ethylsulfonyl)-7-(trifluoromethyl)imidazo[1,2-a]pyridine-2-carbonitrile

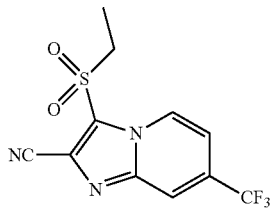 [SMILES: CCS(=O)(=O)c1c(C#N)nc2cc(C(F)(F)F)ccn12]

A solution of 3-(ethylsulfonyl)-7-(trifluoromethyl)imidazo[1,2-a]pyridine-2-carboxamide (630 mg, 1.96 mmol) in phosphoryl chloride (10 ml) was heated at 135° C. for 3 h. The reaction mixture was cooled to room temperature and carefully taken up in water. The aqueous phase was extracted with dichloromethane. The combined organic phases were dried over Na$_2$SO$_4$ and the solvent was removed under reduced pressure.

log P (neutral): 2.28; MH$^+$: 304; $^1$H-NMR (400 MHz, D$_6$-DMSO) δ ppm: 1.24 (t, 3H), 3.66 (q, 2H), 7.69 (dd, 1H), 8.58 (s, 1H), 9.00 (d, 1H).

3-(Ethylsulfonyl)-7-(trifluoromethyl)imidazo[1,2-a]pyridine-2-carboxamide

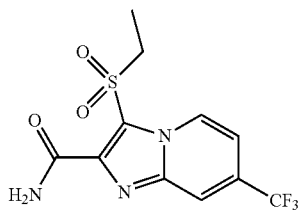

A solution of methyl 3-(ethylsulfonyl)-7-(trifluoromethyl)imidazo[1,2-a]pyridine-2-carboxylate (1.00 g, 2.97 mmol) in ammonium hydroxide (10 ml) was heated at reflux for 5 min. Overnight, the reaction mixture was cooled to room temperature. The solids were filtered off with suction and dried.

log P (neutral): 1.57; MH$^+$: 322; $^1$H-NMR (400 MHz, D$_6$-DMSO) δ ppm: 1.21 (t, 3H), 3.82 (q, 2H), 7.57 (dd, 1H), 7.90 (br s, 1H), 8.14 (br s, 1H), 8.36 (s, 1H), 9.26 (d, 1H).

Methyl 3-(ethylsulfonyl)-7-(trifluoromethyl)imidazo[1,2-a]pyridine-2-carboxylate

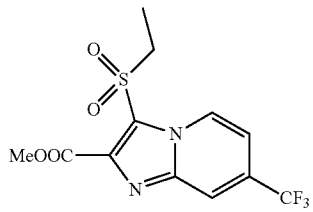 [SMILES: CCS(=O)(=O)c1c(C(=O)OC)nc2cc(C(F)(F)F)ccn12]

Formic acid (2.06 ml, 59.2 mmol) and 35% strength hydrogen peroxide solution (5.2 ml, 59.2 mmol) were added to a solution of methyl 3-(ethylsulfanyl)-7-(trifluoromethyl)imidazo[1,2-a]pyridine-2-carboxylate (1.50 g, 4.93 mmol) in dichloromethane. The reaction mixture was stirred at room temperature for 15 h. The reaction mixture was diluted with water, and sodium bisulfite solution was added with ice cooling.

The pH of the mixture was adjusted to 6-7 using 20% strength sodium bicarbonate solution. The organic phase was separated off and the aqueous phase was extracted with dichloromethane. The combined organic phases were dried over Na$_2$SO$_4$ and the solvent was removed under reduced pressure. The crude product was purified by column chromatography via MPLC using, as mobile phase, a cyclohexane/ethyl acetate gradient.

log P (neutral): 2.15; MH$^+$: 337; $^1$H-NMR (400 MHz, D$_6$-DMSO) δ ppm: 1.26 (t, 3H), 3.70 (q, 2H), 3.94 (s, 3H), 7.61 (dd, 1H), 8.46 (s, 1H), 9.16 (d, 1H).

Methyl 3-(ethylsulfanyl)-7-(trifluoromethyl)imidazo[1,2-a]pyridine-2-carboxylate

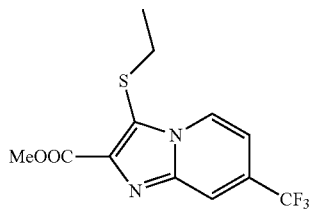 [SMILES: CCSc1c(C(=O)OC)nc2cc(C(F)(F)F)ccn12]

A solution of methyl 3-bromo-7-(trifluoromethyl)imidazo[1,2-a]pyridine-2-carboxylate (10.5 g, 32.6 mmol) and sodium thioethoxide (3.29 g, 39.1 mmol) in DMF (300 ml) was stirred at room temperature for 1 h. The reaction was quenched with saturated ammonium chloride solution and the aqueous phase was extracted with ethyl acetate. The combined organic phases were dried over Na$_2$SO$_4$ and the solvent was removed. The crude product was purified by column chromatography via MPLC using, as mobile phase, a cyclohexane/ethyl acetate gradient.

log P (neutral): 2.56; MH$^+$: 305; $^1$H-NMR (400 MHz, D$_6$-DMSO) δ ppm: 1.07 (t, 3H), 2.93 (q, 2H), 3.91 (s, 3H), 7.40 (dd, 1H), 8.26 (s, 1H), 8.86 (d, 1H).

3-Ethylsulfonyl-2-[6-(trifluoromethyl)-[1,2,4]triazolo[1,5-a]pyrazin-2-yl]quinoline (I-02)

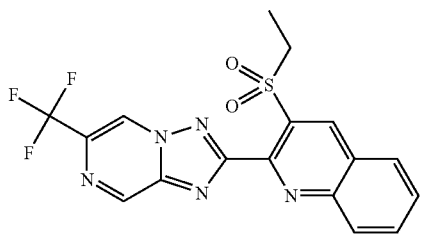 [SMILES: CCS(=O)(=O)c1cc2ccccc2nc1-c1nc2cnc(C(F)(F)F)cn2n1]

Under argon, 41.00 mg (0.10 mmol) of 3-bromo-2-[6-(trifluoromethyl)-[1,2,4]triazolo[1,5-a]pyrazin-2-yl]quinoline, 60.39 mg (0.52 mmol) of sodium methanesulfinate and 2.97 mg (0.01 mmol) of copper(I) iodide in 3 ml of N,N-dimethylformamide were stirred at 120° C. in a microwave synthesizer (Anton Paar, Monowave 400) for four hours. Subsequently, the reaction mixture was concentrated, and the residue was taken up in water and extracted with ethyl acetate. The organic phase was dried over sodium sulfate and the solvent was then distilled off under reduced pressure. The residue was purified by column chromatography using, as mobile phase, a cyclohexane/ethyl acetate gradient.

(log P (neutral): 2.44; MH$^+$: 408; $^1$H-NMR (400 MHz, D$_6$-DMSO) δ ppm: 1.29 (t, 3H), 3.94 (q, 2H), 7.94 (t, 1H), 8.13 (t, 1H), 8.26 (d, 1H), 8.48 (d, 1H), 9.31 (s, 1H), 9.72 (s, 1H), 10.08 (s, 1H).

3-Bromo-2-[6-(trifluoromethyl)-[1,2,4]triazolo[1,5-a]pyrazin-2-yl]quinoline

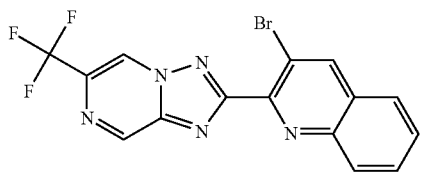 [SMILES: FC(F)(F)c1cn2nc(-c3nc4ccccc4cc3Br)nc2cn1]

A mixture of 27.66 mg (0.16 mmol) of potassium iodide and 33.83 mg (0.13 mmol) of iodine in 6 ml of DMSO was stirred at room temperature for 10 min. 44.00 mg (0.11 mmol) of 3-bromo-N-[5-(trifluoromethyl)pyrazin-2-yl]quinoline-2-carboxamidine and 45.05 mg (0.33 mmol) of potassium carbonate were then added and the reaction mixture was stirred at 100° C. for 15 min. The cooled reaction was quenched with 5% strength sodium thiosulfate solution, diluted with conc. sodium chloride solution and extracted three times with ethyl acetate. The combined organic phases were dried over sodium sulfate and then the solvent was then distilled off under reduced pressure. The residue was purified by column chromatography using, as mobile phase, a cyclohexane/ethyl acetate gradient.

(log P (neutral): 2.98; MH$^+$: 393; $^1$H-NMR (400 MHz, D$_6$-DMSO) δ ppm: 7.81 (t, 1H), 7.94 (t, 1H), 8.12-8.15 (m, 2H), 9.07 (s, 1H), 9.70 (s, 1H), 10.05 (s, 1H).

3-Bromo-N-[5-(trifluoromethyl)pyrazin-2-yl]quinoline-2-carboxamidine

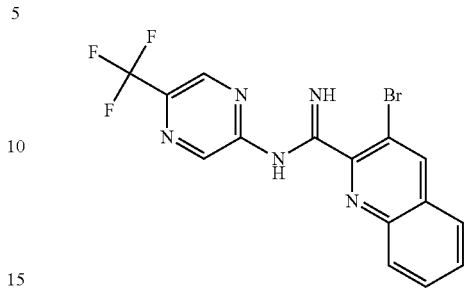

Under argon and at 0° C., 93.00 mg (0.55 mmol) of 5-(trifluoromethyl)pyrazine-2-amine were dissolved in THF, 107.57 mg (0.58 mmol, 0.58 ml) of 1.0 M sodium bis(trimethylsilyl)amide solution in THF were added dropwise, the mixture was stirred for another 30 min and 135.69 mg (0.55 mmol) of 3-bromoquinoline-2-carbonitrile were then added. The reaction mixture was stirred at room temperature for 20 h. The solvent was distilled off under reduced pressure and the residue was purified by column chromatography purification using a cyclohexane/ethyl acetate gradient as eluent.

(log P (neutral): 3.01; MH$^+$: 395; $^1$H-NMR (400 MHz, D$_6$-DMSO) δ ppm: 7.74 (t, 1H), 7.88 (t, 1H), 8.04-8.09 (m, 2H), 8.42 (s, 1H), 8.65 (br. s, 1H), 8.88 (s, 1H), 9.45 (br. s, 1H).

Methods

The log P values are measured according to EEC Directive 79/831 Annex V.A8 by HPLC (high-performance liquid chromatography) on a reversed-phase column (C 18). Temperature: 55° C.

The LC-MS determination in the acidic range is effected at pH 2.7 with 0.1% aqueous formic acid and acetonitrile (containing 0.1% formic acid) as mobile phases; linear gradient from 10% acetonitrile to 95% acetonitrile. Called log P (HCOOH) in the table.

The LC-MS determination in the neutral range is effected at pH 7.8 with 0.001 molar aqueous ammonium bicarbonate solution and acetonitrile as mobile phases; linear gradient from 10% acetonitrile to 95% acetonitrile. Called log P (neutral) in the table.

Calibration is carried out using unbranched alkan-2-ones (having 3 to 16 carbon atoms) with known Log P values (Log P values determined on the basis of the retention times by linear interpolation between two successive alkanones).

The NMR data of selected examples are listed either in conventional form (δ values, multiplet splitting, number of hydrogen atoms) or as NMR peak lists.

In each case, the solvent in which the NMR spectrum was recorded is stated.

NMR Peak List Method

The $^1$H NMR data of selected examples are stated in the form of $^1$H NMR peak lists. For each signal peak, first the δ value in ppm and then the signal intensity in round brackets are listed. The pairs of δ value signal intensity numbers for different signal peaks are listed with separation from one another by semicolons.

The peak list for one example therefore takes the form of: $\delta_1$ (intensity$_1$); $\delta_2$ (intensity$_2$); . . . ; $\delta_i$ (intensity$_i$); . . . ; $\delta_n$ (intensity$_n$)

The intensity of sharp signals correlates with the height of the signals in a printed example of an NMR spectrum in cm and shows the true ratios of the signal intensities. In the case of broad signals, several peaks or the middle of the signal and the relative intensity thereof may be shown in comparison to the most intense signal in the spectrum.

For calibration of the chemical shift of NMR spectra, we use tetramethylsilane and/or the chemical shift of the solvent, particularly in the case of spectra which are measured in DMSO. Therefore, the tetramethylsilane peak may but need not occur in NMR peak lists.

The lists of the $^1$H NMR peaks are similar to the conventional NMR printouts and thus usually contain all peaks listed in a conventional NMR interpretation.

In addition, like conventional $^1$H NMR printouts, they may show solvent signals, signals of stereoisomers of the target compounds which are likewise provided by the invention, and/or peaks of impurities.

In the reporting of compound signals within the delta range of solvents and/or water, our lists of NMR peaks show the standard solvent peaks, for example peaks of DMSO in DMSO-$D_6$ and the peak of water, which usually have a high intensity on average.

The peaks of stereoisomers of the target compounds and/or peaks of impurities usually have a lower intensity on average than the peaks of the target compounds (for example with a purity of >90%).

Such stereoisomers and/or impurities may be typical of the particular preparation process. Their peaks can thus help in this case to identify reproduction of our preparation process with reference to "by-product fingerprints".

An expert calculating the peaks of the target compounds by known methods (MestreC, ACD simulation, but also with empirically evaluated expected values) can, if required, isolate the peaks of the target compounds, optionally using additional intensity filters. This isolation would be similar to the peak picking in question in conventional $^1$H NMR interpretation.

Further details of $^1$H NMR peak lists can be found in the Research disclosure Database Number 564025.

The following compounds of formula (I) listed in Table 1 were prepared analogously to the processes described.

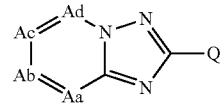

(I)

TABLE 1

| Example | Structure | |
|---|---|---|
| I-01 | 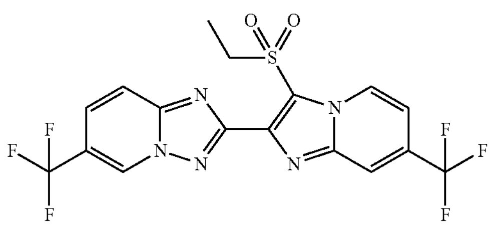 [SMILES: CCS(=O)(=O)c1c(-c2nc3ccc(C(F)(F)F)cn3n2)nc2cc(C(F)(F)F)ccn12] | I-01: $^1$H-NMR(400.0 MHz, $d_6$-DMSO):<br>δ = 9.8416(4.7); 9.2886(3.5); 9.2700(3.7); 8.4799 (5.0); 8.3155(0.6); 8.1992(3.0); 8.1758(4.3); 8.0814(3.4); 8.0773(3.5); 8.0581(2.3); 8.0539(2.4); 7.6265(3.0); 7.6218(3.1); 7.6077(2.9); 7.6031(3.0); 4.0612(1.9); 4.0427(6.5); 4.0242(6.5); 4.0059 (2.1); 3.3569(0.3); 3.3211(141.0); 2.6711(2.4); 2.6669(1.8); 2.5738(0.3); 2.5065(320.6); 2.5021 (416.1); 2.4978(299.9); 2.3333(1.7); 2.3289(2.3); 2.3247(1.7); 2.0743(0.3); 1.3561(7.2); 1.3377(16.0); 1.3192(7.0); −0.0001(8.7) |
| I-02 | 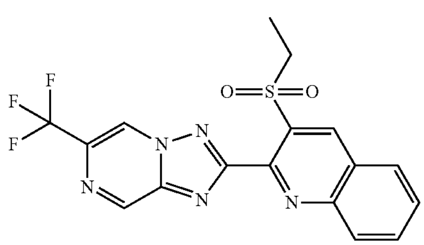 [SMILES: CCS(=O)(=O)c1cc2ccccc2nc1-c1nc2cnc(C(F)(F)F)cn2n1] | I-02: $^1$H-NMR(400.0 MHz, $d_6$-DMSO):<br>δ = 10.0801(5.1); 9.7150(5.1); 9.3145(7.2); 8.4889(2.5); 8.4686(2.7); 8.2722(2.4); 8.2511(3.3); 8.1478(1.5); 8.1300(2.5); 8.1122(1.3); 8.1094(1.3); 7.9627(1.7); 7.9441(2.6); 7.9255(1.3); 4.0376(0.4); 4.0200(0.4); 3.9713(1.6); 3.9529(5.4); 3.9344(5.5); 3.9159(1.7); 3.3357(42.9); 2.6709(1.1); 2.6666(0.8); 2.5061(136.7); 2.5018(178.6); 2.4975(132.5); 2.3329(0.8); 2.3285(1.1); 2.3241(0.8); 1.9887(1.5); 1.3972(16.0); 1.3078(5.7); 1.2893(12.4); 1.2709(5.5); 1.1923(0.4); 1.1747(0.8); 1.1568(0.4); 0.0073(2.0); −0.0005(47.1) |
| I-03 | 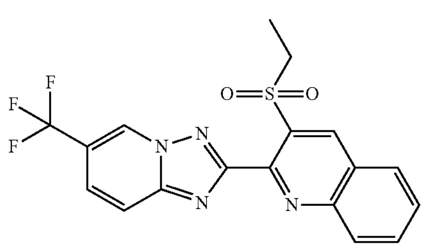 [SMILES: CCS(=O)(=O)c1cc2ccccc2nc1-c1nc2ccc(C(F)(F)F)cn2n1] | I-03: $^1$H-NMR(400.0 MHz, $d_6$-DMSO):<br>δ = 9.8692(5.0); 9.2787(9.3); 8.4711(3.2); 8.4505(3.4); 8.2585(3.1); 8.2374(4.2); 8.2160(2.9); 8.1927(4.5); 8.1344(1.9); 8.1313(2.1); 8.1134(6.9); 8.1094(5.4); 8.0959(2.0); 8.0900(3.0); 8.0853(2.6); 7.9416(2.3); 7.9238(3.5); 7.9037(1.8); 5.7569(0.8); 4.0078(2.1); 3.9894(7.0); 3.9709(7.1); 3.9524(2.1); 3.3224(81.8); 2.6756(0.7); 2.6717(0.9); 2.6673(0.7); 2.5069(116.8); 2.5025(154.9); 2.4981(117.2); 2.3337(0.6); 2.3294(0.9); 2.3250(0.7); 1.9893(0.6); 1.3971(1.2); 1.2952(7.4); 1.2768(16.0); 1.2582(7.5); 1.2341(3.3); 1.2065(0.3); 1.1749(0.3); 0.8533(0.5); 0.0075(2.4); −0.0001(52.5); −0.0080(2.6) |

TABLE 1-continued

| Example | Structure | |
|---|---|---|
| I-04 | 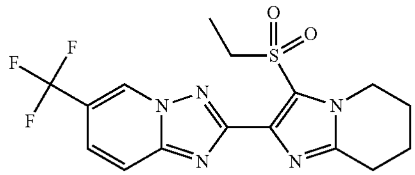 [SMILES: CCS(=O)(=O)c1c(-c2nc3ccc(C(F)(F)F)cn3n2)nc2n1CCCC2] | I-04: $^1$H-NMR(601.6 MHz, CDCl$_3$):<br>δ = 8.9693(1.4); 7.8892(2.1); 7.8734(2.5); 7.6973(2.2); 7.6947(2.2); 7.6817(1.9); 7.6791(1.9); 7.4307(1.5); 7.2595(274.8); 7.0832(1.6); 5.2983(8.7); 4.4169(2.8); 4.4068(4.9); 4.3968(2.8); 3.9110(2.0); 3.8987(6.4); 3.8864(6.5); 3.8739(2.2); 3.0823(1.8); 3.0713(3.4); 3.0605(1.9); 2.8762(0.4); 2.0900(0.6); 2.0801(1.6); 2.0703(2.7); 2.0610(2.2); 2.0506(1.1); 1.9959(0.9); 1.9853(2.3); 1.9751(2.4); 1.9660(1.7); 1.5554(83.1); 1.4911(0.5); 1.4374(0.4); 1.4231(7.4); 1.4108(16.0); 1.3985(7.3); 1.2550(1.0); 0.1570(0.9); 0.0965(1.7); 0.0052(11.9); −0.0002(433.0); −0.0057(13.8); −0.0430(0.4); −0.1001(1.7) |
| I-05 | 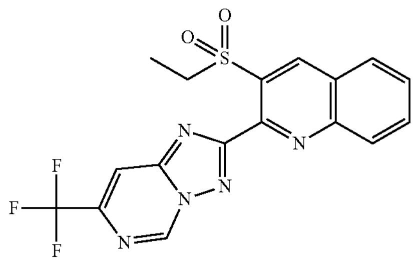 [SMILES: CCS(=O)(=O)c1cc2ccccc2nc1-c1nc2cc(C(F)(F)F)ncn2n1] | I-05: $^1$H-NMR(400.0 MHz, d$_6$-DMSO):<br>δ = 17.6819(0.6); 16.9564(0.5); 13.7146(0.6); 10.1937(6.6); 9.3104(8.8); 8.7809(6.8); 8.6290(0.5); 8.4882(3.4); 8.4683(3.7); 8.2731(3.0); 8.2534(4.3); 8.1474(2.1); 8.1301(3.4); 8.1089(1.7); 7.9645(2.4); 7.9446(3.5); 7.9272(1.9); 7.7559(0.5); 3.9558(2.1); 3.9376(7.0); 3.9194(7.1); 3.9008(2.2); 3.3190(215.3); 2.6703(6.7); 2.6659(5.0); 2.5056(917.8); 2.5012(1166.7); 2.4968(838.2); 2.4313(1.2); 2.3908(0.6); 2.3325(5.1); 2.3280(6.7); 2.0854(2.0); 1.4267(0.6); 1.3977(5.9); 1.2993(7.2); 1.2808(16.0); 1.2623(7.2); 1.2396(0.7); 1.2235(0.6); 1.2042(0.6); 0.1464(3.8); −0.0001(903.2); −0.0083(40.8); −0.1497(4.3); −3.2039(0.6); −3.5374(0.6) |
| I-06 | 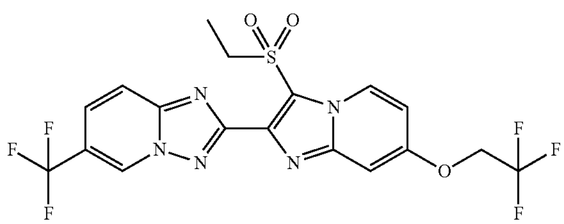 [SMILES: CCS(=O)(=O)c1c(-c2nc3ccc(C(F)(F)F)cn3n2)nc2cc(OCC(F)(F)F)ccn12] | I-06: $^1$H-NMR(400.0 MHz, d$_6$-DMSO):<br>δ = 9.8124(4.7); 8.9723(5.0); 8.9529(5.4); 8.1736(2.9); 8.1502(4.4); 8.0603(3.5); 8.0561(3.6); 8.0368(2.3); 8.0325(2.4); 7.5186(4.7); 7.5120(4.9); 7.1768(3.2); 7.1700(3.2); 7.1574(3.2); 7.1506(3.2); 5.0633(1.6); 5.0416(5.2); 5.0197(5.6); 4.9977(1.9); 3.9630(1.9); 3.9446(6.5); 3.9262(6.7); 3.9078(2.0); 3.3228(176.8); 2.6759(0.7); 2.6714(1.0); 2.6669(0.7); 2.5246(2.3); 2.5111(57.5); 2.5067(120.4); 2.5023(161.6); 2.4978(117.9); 2.4934(58.3); 2.3335(0.7); 2.3289(1.0); 2.3247(0.7); 1.3195(7.0); 1.3012(16.0); 1.2827(6.9); 1.2341(0.7); 0.1460(0.6); 0.0078(4.2); −0.0001(127.2); −0.0083(5.6); −0.1497(0.6) |
| I-07 | 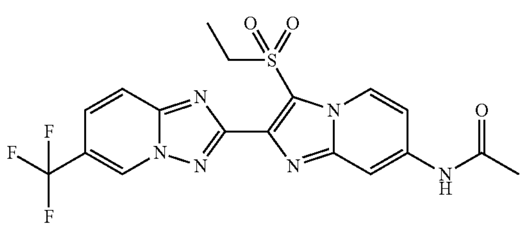 [SMILES: CCS(=O)(=O)c1c(-c2nc3ccc(C(F)(F)F)cn3n2)nc2cc(NC(C)=O)ccn12] | I-07: $^1$H-NMR(400.0 MHz, d$_6$-DMSO):<br>δ = 10.6040(3.2); 9.8073(2.7); 8.9912(2.6); 8.9721(2.8); 8.2647(2.9); 8.2600(2.9); 8.1663(1.7); 8.1428(2.5); 8.0534(2.0); 8.0492(2.0); 8.0298(1.3); 8.0256(1.4); 7.3313(1.7); 7.3259(1.7); 7.3122(1.7); 7.3067(1.7); 3.9432(1.1); 3.9249(3.7); 3.9064(3.8); 3.8879(1.1); 3.3201(51.6); 2.6752(0.6); 2.6709(0.8); 2.6665(0.6); 2.5241(1.8); 2.5104(45.9); 2.5063(95.8); 2.5019(128.6); 2.4974(94.5); 2.4932(47.1); 2.3332(0.5); 2.3286(0.8); 2.3241(0.6); 2.1492(16.0); 2.0746(0.4); 1.7541(2.3); 1.3198(4.0); 1.3015(8.9); 1.2830(3.9); 1.2341(0.3); 0.1458(0.4); 0.0079(2.8); −0.0002(86.7); −0.0083(3.8); −0.1498(0.4) |
| I-08 | 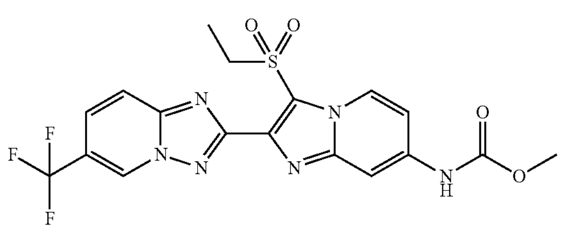 [SMILES: CCS(=O)(=O)c1c(-c2nc3ccc(C(F)(F)F)cn3n2)nc2cc(NC(=O)OC)ccn12] | I-08: $^1$H-NMR(400.0 MHz, d$_6$-DMSO):<br>δ = 10.4127(3.0); 9.8050(2.4); 8.9715(2.3); 8.9522(2.4); 8.1653(1.5); 8.1417(2.2); 8.0527(1.9); 8.0486(1.8); 8.0292(1.3); 8.0249(1.3); 7.9909(2.4); 7.9863(2.4); 7.3351(1.6); 7.3295(1.5); 7.3159(1.5); 7.3103(1.5); 5.7562(5.0); 3.9330(1.0); 3.9145(3.3); 3.8960(3.3); 3.8777(1.0); 3.7584(16.0); 3.4730(0.9); 3.3205(59.6); 2.6757(0.5); 2.6711(0.7); 2.6668(0.5); 2.5244(1.7); 2.5109(41.7); 2.5066(87.2); 2.5021(116.9); 2.4976(84.5); 2.4933(41.2); 2.3335(0.5); 2.3289(0.7); 2.3243(0.5); 1.3166(3.6); 1.2982(8.0); 1.2798(3.5); 1.2342(0.6); 0.0080(0.6); −0.0002(19.4); −0.0083(0.8) |

TABLE 1-continued

| Example | Structure | |
|---|---|---|
| I-09 | 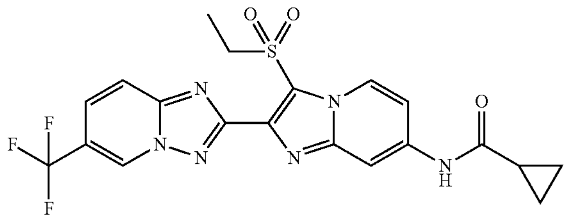 [SMILES: CCS(=O)(=O)c1c(-c2nc3ccc(C(F)(F)F)cn3n2)nc2cc(NC(=O)C3CC3)ccn12] | I-09: $^1$H-NMR(400.0 MHz, d$_6$-DMSO): δ = 16.9449(0.4); 10.8658(6.2); 9.8037(6.2); 8.9956(5.0); 8.9769(5.2); 8.3148(1.2); 8.2609(6.2); 8.1629(3.4); 8.1402(5.0); 8.0496(4.6); 8.0261(3.0); 7.7628(0.5); 7.5745(0.5); 7.3574(3.3); 7.3528(3.4); 7.3386(3.3); 7.3338(3.3); 3.9906(0.5); 3.9637(0.5); 3.9458(2.4); 3.9267(6.7); 3.9086(6.8); 3.8893(2.3); 3.8149(0.4); 3.6060(0.5); 3.5870(0.5); 3.4719(0.5); 3.4359(0.7); 3.4139(0.9); 3.3228(1785.6); 2.6706(9.7); 2.6336(0.6); 2.6097(0.6); 2.5991(0.8); 2.5719(2.6); 2.5016(1669.8); 2.3283(9.6); 1.8704(2.1); 1.8552(2.6); 1.8394(2.2); 1.8247(0.8); 1.4751(0.4); 1.3423(0.5); 1.3215(7.4); 1.3031(15.6); 1.2844(7.4); 1.2365(2.5); 1.2036(0.5); 1.1967(0.5); 1.1601(0.6); 1.1418(1.2); 1.1249(0.6); 0.9085(16.0); 0.8933(12.0); 0.8542(0.7); 0.8431(0.4); 0.1449(0.5); −0.0002(111.2); −0.1490(0.5) |
| I-10 | 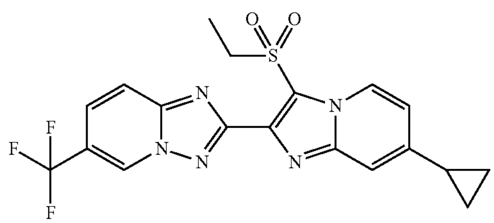 [SMILES: CCS(=O)(=O)c1c(-c2nc3ccc(C(F)(F)F)cn3n2)nc2cc(C3CC3)ccn12] | I-10: $^1$H-NMR(400.0 MHz, d$_6$-DMSO): δ = 9.8048 (4.7); 8.9316 (4.2); 8.9131 (4.4); 8.1671 (2.9); 8.1436 (4.4); 8.0542 (3.5); 8.0499(3.5); 8.0307 (2.3); 8.0264 (2.4); 7.6479 (5.3); 7.0595 (3.1); 7.0550 (3.1); 7.0411 (3.0); 7.0365(3.1); 3.9453 (1.9); 3.9269 (6.7); 3.9084 (6.8); 3.8900 (2.0); 3.3198 (54.2); 2.6758 (0.6); 2.6712 (0.9); 2.6667 (0.7); 2.5243 (2.3); 2.5107 (56.8); 2.5066 (116.0); 2.5021 (153.9); 2.4977 (112.6); 2.4934 (56.4); 2.3332 (0.7); 2.3288 (0.9); 2.3246 (0.7); 2.1877 (0.5); 2.1754 (1.1); 2.1669 (1.3); 2.1549 (2.3); 2.1426 (1.4); 2.1342 (1.2); 2.1215 (0.6); 2.0747 (1.5); 1.3096 (7.1); 1.2912 (16.0); 1.2727 (7.0); 1.1526 (1.3); 1.1411 (3.8); 1.1354 (4.3); 1.1246 (2.4); 1.1204 (4.0); 1.1147 (4.0); 1.1044 (1.6); 0.9384 (1.6); 0.9273 (4.7); 0.9225 (4.6); 0.9156 (4.3); 0.9103 (5.0); 0.8986 (1.3); 0.1458 (0.7); 0.0076 (5.3); −0.0003 (149.7); −0.0084 (7.2); −0.1499 (0.7) |
| I-11 | 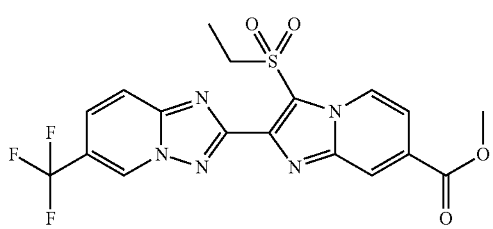 [SMILES: CCS(=O)(=O)c1c(-c2nc3ccc(C(F)(F)F)cn3n2)nc2cc(C(=O)OC)ccn12] | I-11: $^1$H-NMR(400.0 MHz, d$_6$-DMSO): δ = 9.8386 (2.2); 9.2203 (1.8); 9.2020 (1.8); 8.4175 (2.8); 8.1959 (1.4); 8.1724 (2.0); 8.0787 (1.7); 8.0746 (1.7); 8.0552 (1.2); 8.0511 (1.2); 7.7398 (1.8); 7.7354 (1.8); 7.7214 (1.8); 7.7170 (1.8); 4.0553 (1.0); 4.0370 (3.3); 4.0185 (3.3); 4.0000 (1.0); 3.9631 (16.0); 3.3232 (23.8); 2.6724 (0.4); 2.5251 (1.1); 2.5117 (25.4); 2.5075 (51.9); 2.5030 (69.1); 2.4986 (50.4); 2.4943 (25.1); 2.3297 (0.4); 2.0751 (2.8); 1.3518 (3.6); 1.3334 (8.2); 1.3149 (3.6); 0.0078 (2.1); −0.0002 (61.9); −0.0084 (2.7) |
| I-12 | 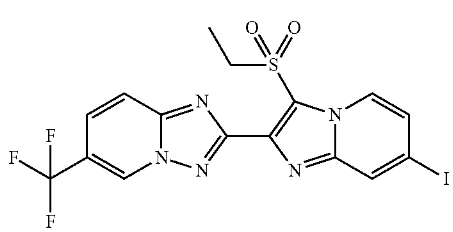 [SMILES: CCS(=O)(=O)c1c(-c2nc3ccc(C(F)(F)F)cn3n2)nc2cc(I)ccn12] | I-12: $^1$H-NMR(400.0 MHz, d$_6$-DMSO): δ = 9.8146 (5.1); 9.0106 (0.4); 8.9915 (0.4); 8.8573 (4.6); 8.8387 (4.9); 8.4372 (5.6); 8.4347 (5.7); 8.3094 (0.4); 8.3050 (0.5); 8.1762 (3.0); 8.1526 (4.6); 8.0643 (3.8); 8.0602 (3.6); 8.0408 (2.6); 8.0368 (2.4); 7.6147 (3.5); 7.6104 (3.5); 7.5963 (3.4); 7.5920 (3.5); 3.9921 (2.1); 3.9739 (6.8); 3.9555 (6.8); 3.9370 (2.0); 3.3214 (295.4); 2.6751 (1.3); 2.6708 (1.8); 2.6662 (1.4); 2.5240 (4.8); 2.5063 (241.6); 2.5019 (317.8); 2.4974 (230.4); 2.3327 (1.4); 2.3287 (1.9); 2.3241 (1.4); 1.3328 (0.8); 1.3230 (7.2); 1.3148 (2.3); 1.3046 (16.0); 1.2861 (7.0); 0.1461 (0.6); 0.0078 (4.6); −0.0002 (136.2); −0.0084 (5.7); −0.1498 (0.6) |

TABLE 1-continued

| Example | Structure | |
|---|---|---|
| I-13 | 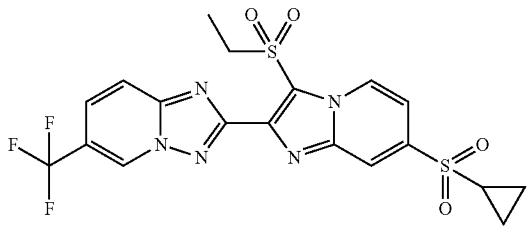 [SMILES: CCS(=O)(=O)c1c(-c2nc3ccc(C(F)(F)F)cn3n2)nc2cc(S(=O)(=O)C3CC3)ccn12] | I-13: ¹H-NMR(400.0 MHz, d₆-DMSO): δ = 9.8475 (4.9); 9.3073 (4.4); 9.2887 (4.6); 8.4372 (5.4); 8.4347 (5.4); 8.3149 (0.3); 8.2032 (3.0); 8.1796 (4.5); 8.0850 (3.5); 8.0809 (3.6); 8.0615 (2.4); 8.0574 (2.5); 7.7513 (3.5); 7.7466 (3.5); 7.7329 (3.4); 7.7281 (3.5); 4.0738 (1.9); 4.0554 (6.6); 4.0369 (6.8); 4.0185 (2.1); 3.3845 (0.4); 3.3226 (443.3); 3.1288 (0.6); 3.1165 (1.3); 3.1087 (1.5); 3.0973 (2.7); 3.0854 (1.6); 3.0775 (1.4); 3.0656 (0.7); 2.6751 (1.7); 2.6709 (2.3); 2.6666 (1.7); 2.5239 (6.0); 2.5103 (141.2); 2.5062 (289.8); 2.5018 (387.0); 2.4973 (284.8); 2.4932 (144.7); 2.3330 (1.7); 2.3284 (2.3); 2.3242 (1.7); 1.3691 (7.1); 1.3507 (16.0); 1.3321 (7.1); 1.2843 (0.9); 1.2721 (3.5); 1.2650 (4.3); 1.2540 (4.6); 1.2448 (1.7); 1.2346 (1.3); 1.2177 (0.7); 1.2060 (0.4); 1.1976 (0.4); 1.1815 (1.3); 1.1698 (3.6); 1.1630 (3.8); 1.1502 (4.0); 1.1444 (3.2); 1.1314 (0.8); 0.1462 (0.8); 0.0079 (6.1); −0.0001 (179.9); −0.0082 (9.1); −0.1494 (0.8) |
| I-14 | 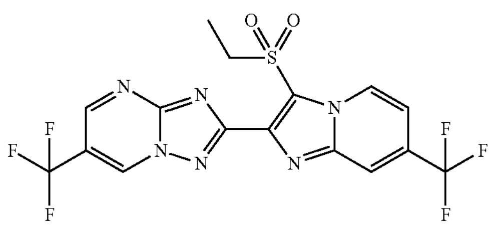 [SMILES: CCS(=O)(=O)c1c(-c2nc3ncc(C(F)(F)F)cn3n2)nc2cc(C(F)(F)F)ccn12] | I-14: ¹H-NMR(400.0 MHz, d₆-DMSO): δ = 9.7603 (0.4); 9.0627 (0.4); 8.9894 (1.2); 8.9549 (0.3); 8.9269 (4.9); 8.9208 (5.1); 8.8563 (0.5); 8.8503 (0.6); 8.6396 (4.0); 8.6366 (3.9); 8.5370 (0.5); 8.3156 (0.4); 8.2861 (1.2); 8.0243 (0.6); 8.0093 (0.3); 7.9918 (6.1); 7.9664 (0.4); 7.4847 (5.1); 7.4815 (5.0); 7.2729 (0.7); 7.2217 (0.6); 3.5130 (0.4); 3.4885 (0.4); 3.4290 (0.6); 3.3293 (8.4); 3.2476 (0.7); 3.2392 (0.6); 3.2283 (0.5); 3.1965 (0.5); 3.1845 (0.7); 3.1772 (0.5); 3.1657 (0.9); 3.1465 (0.7); 3.1232 (0.9); 3.1048 (0.9); 3.0865 (0.4); 2.8270 (0.7); 2.7445 (1.7); 2.7259 (5.4); 2.7075 (5.5); 2.6894 (2.0); 2.6759 (1.0); 2.6712 (1.2); 2.6671 (1.0); 2.5416 (18.9); 2.5068 (151.6); 2.5024 (197.5); 2.4980 (145.7); 2.3291 (1.2); 2.3242 (0.9); 2.2315 (0.6); 1.9904 (0.3); 1.2362 (1.8); 1.2017 (0.4); 1.1925 (0.4); 1.1723 (0.7); 1.1536 (1.2); 1.1399 (0.8); 1.1352 (0.7); 1.1214 (1.1); 1.1030 (0.6); 1.0697 (0.4); 1.0598 (1.0); 1.0416 (1.9); 1.0231 (0.9); 0.8562 (7.6); 0.8377 (16.0); 0.8193 (7.1); 0.1461 (0.5); 0.0079 (4.1); −0.0002 (107.4); −0.1498 (0.5) |
| I-15 | 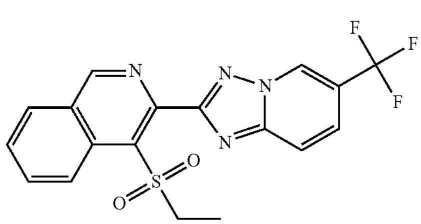 [SMILES: CCS(=O)(=O)c1c(-c2nc3ccc(C(F)(F)F)cn3n2)ncc2ccccc12] | I-15: ¹H-NMR(400.2 MHz, d₆-DMSO): δ = 9.8113 (4.8); 9.7423 (8.5); 8.9192 (3.4); 8.8972 (3.6); 8.4742 (3.1); 8.4543 (3.3); 8.1690 (3.0); 8.1593 (2.0); 8.1562 (2.1); 8.1453 (5.2); 8.1386 (3.5); 8.1200 (2.1); 8.1170 (1.9); 8.0715 (3.6); 8.0674 (3.6); 8.0479 (2.3); 8.0439 (2.3); 8.0148 (2.4); 7.9958 (3.4); 7.9776 (1.8); 6.5362 (0.5); 3.8191 (2.2); 3.8006 (6.9); 3.7821 (6.9); 3.7636 (2.2); 3.3256 (37.6); 2.6762 (0.7); 2.6722 (1.0); 2.6679 (0.7); 2.5074 (112.2); 2.5030 (148.0); 2.4987 (111.0); 2.3297 (0.9); 1.2944 (7.6); 1.2759 (16.0); 1.2574 (7.3); 0.1474 (0.4); 0.0090 (5.5); 0.0012 (93.8); −0.1482 (0.4) |

TABLE 1-continued

| Example | Structure | |
|---|---|---|
| II-16 | 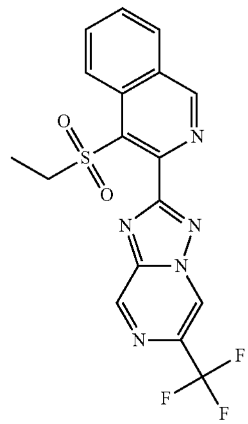 [SMILES: CCS(=O)(=O)c1c(-c2nc3cnc(C(F)(F)F)cn3n2)ncc2ccccc12] | I-16: $^1$H-NMR(400.2 MHz, d$_6$-DMSO): δ = 10.0394 (6.1); 9.7696 (8.4); 9.6779 (6.1); 8.9100 (3.2); 8.8881 (3.5); 8.4955 (3.0); 8.4755 (3.2); 8.1808 (1.5); 8.1777 (1.6); 8.1632 (2.1); 8.1597 (2.8); 8.1560 (1.8); 8.1415 (1.9); 8.1384 (1.8); 8.0373 (2.3); 8.0189 (3.3); 8.0009 (1.7); 3.7943 (2.1); 3.7758 (6.7); 3.7573 (6.8); 3.7389 (2.2); 3.3278 (12.0); 2.5262 (1.9); 2.5216 (2.6); 2.5083 (40.2); 2.5039 (54.3); 2.4995 (40.7); 2.0776 (0.7); 1.2918 (7.4); 1.2734 (16.0); 1.2548 (7.2); 0.0008 (6.6) |

USE EXAMPLES

*Ctenocephalides felis*—In Vitro Contact Tests with Adult Cat Fleas

For the coating of the test tubes, 9 mg of active compound are first dissolved in 1 ml of acetone p.a. and then diluted to the desired concentration with acetone p.a. 250 μl of the solution are distributed homogeneously on the inner walls and the base of a 25 ml glass tube by turning and rocking on an orbital shaker (rocking rotation at 30 rpm for 2 h). With 900 ppm of active compound solution and internal surface area 44.7 cm$^2$, given homogeneous distribution, an area-based dose of 5 μg/cm$^2$ is achieved.

After the solvent has evaporated off, the tubes are populated with 5-10 adult cat fleas (*Ctenocephalides felis*), sealed with a perforated plastic lid and incubated in a horizontal position at room temperature and ambient humidity. After 48 h, efficacy is determined. To this end, the tubes are stood upright and the fleas are knocked to the base of the tube. Fleas which remain motionless at the base or move in an uncoordinated manner are considered to be dead or moribund.

A substance shows good efficacy against *Ctenocephalides felis* if at least 80% efficacy was achieved in this test at an application rate of 5 μg/cm$^2$. 100% efficacy means that all the fleas were dead or moribund. 0% efficacy means that no fleas were harmed.

In this test, for example, the following compounds from the preparation examples show an efficacy of 100% at an application rate of 5 μg/cm$^2$ (=500 g of ai/ha): I-01, I-05, I-12

*Rhipicephalus sanguineus*—In Vitro Contact Tests with Adult Brown Doe Ticks

For the coating of the test tubes, 9 mg of active compound are first dissolved in 1 ml of acetone p.a. and then diluted to the desired concentration with acetone p.a. 250 μl of the solution are distributed homogeneously on the inner walls and the base of a 25 ml glass tube by turning and rocking on an orbital shaker (rocking rotation at 30 rpm for 2 h). With 900 ppm of active compound solution and internal surface area 44.7 cm$^2$, given homogeneous distribution, an area-based dose of 5 μg/cm$^2$ is achieved.

After the solvent has evaporated off, the tubes are populated with 5-10 adult dog ticks (*Rhipicephalus sanguineus*), sealed with a perforated plastic lid and incubated in a horizontal position in the dark at room temperature and ambient humidity. After 48 h, efficacy is determined. To this end, the ticks are knocked to the base of the tube and incubated on a hotplate at 45-50° C. for not more than 5 min. Ticks which remain motionless on the base or move in such an uncoordinated manner that they are unable to deliberately avoid the heat by climbing upwards are considered to be dead or moribund.

A substance shows good activity against *Rhipicephalus sanguineus* if, in this test, an efficacy of at least 80% was achieved at an application rate of 5 μg/cm$^2$. An efficacy of 100% means that all the ticks were dead or moribund. 0% efficacy means that none of the ticks were harmed.

In this test, for example, the following compound from the preparation examples shows an efficacy of 80% at an application rate of 1 μg/cm$^2$ (=100 g of ai/ha): I-05

*Boophilus microplus* Injection Test

Solvent: dimethyl sulfoxide

To produce a suitable active compound formulation, 10 mg of active compound are mixed with 0.5 ml of solvent and the concentrate is diluted to the desired concentration with solvent.

1 μl of the active compound solution is injected into the abdomen of 5 engorged adult female cattle ticks (*Boophilus microplus*). The animals are transferred into dishes and kept in a climate-controlled room.

Efficacy is assessed after 7 days by laying of fertile eggs. Eggs which are not visibly fertile are stored in a climate-controlled cabinet until the larvae hatch after about 42 days. An efficacy of 100% means that none of the ticks has laid any fertile eggs; 0% means that all the eggs are fertile.

In this test, for example, the following compounds from the preparation examples show an efficacy of 100% at an application rate of 20 μg/animal I-09

*Ctenocephalides felis*—Oral Test

Solvent: dimethyl sulfoxide

To produce a suitable active compound formulation, 10 mg of active compound are mixed with 0.5 ml of dimethyl sulfoxide. Dilution with citrated cattle blood gives the desired concentration.

About 20 unfed adult cat fleas (*Ctenocephalides felis*) are placed into a chamber which is closed at the top and bottom with gauze. A metal cylinder whose bottom end is closed with parafilm is placed onto the chamber. The cylinder contains the blood/active compound formulation, which can be imbibed by the fleas through the parafilm membrane.

After 2 days, the kill in % is determined. 100% means that all of the fleas have been killed; 0% means that none of the fleas have been killed.

In this test, for example, the following compounds from the preparation examples show an efficacy of 100% at an application rate of 100 ppm: I-01, I-07

In this test, for example, the following compounds from the preparation examples show an efficacy of 95% at an application rate of 100 ppm: I-05, I-09

In this test, for example, the following compound from the preparation examples shows an efficacy of 90% at an application rate of 100 ppm: I-08

*Lucilia cuprina* Test

Solvent: dimethyl sulfoxide

To produce a suitable active compound formulation, 10 mg of active compound are mixed with 0.5 ml of dimethyl sulfoxide, and the concentrate is diluted with water to the desired concentration.

About 20 L1 larvae of the Australian sheep blowfly (*Lucilia cuprina*) are transferred into a test vessel containing minced horsemeat and the active compound formulation of the desired concentration.

After 2 days, the kill in % is determined. 100% means that all the larvae have been killed; 0% means that no larvae have been killed.

In this test, for example, the following compound from the preparation examples shows an efficacy of 100% at an application rate of 100 ppm: I-01, I-05, I-08, I-12

*Musca domestica* Test

Solvent: dimethyl sulfoxide

To produce a suitable active compound formulation, 10 mg of active compound are mixed with 0.5 ml of dimethyl sulfoxide, and the concentrate is diluted with water to the desired concentration.

Vessels containing a sponge treated with sugar solution and the desired concentration of active compound formulation are populated with 10 adult houseflies (*Musca domestica*).

After 2 days, the kill in % is determined. 100% means that all of the flies have been killed; 0% means that none of the flies have been killed.

In this test, for example, the following compound from the preparation examples shows an efficacy of 90% at an application rate of 100 ppm: I-12

*Myzus persicae* Oral Test

Solvent: 100 parts by weight of acetone

To produce a suitable preparation of active compound, 1 part by weight of active compound is dissolved using the specified parts by weight of solvent and made up with water until the desired concentration is attained.

50 µl of the active compound preparation are transferred into microtitre plates and made up to a final volume of 200 µl with 150 µl of IPL41 insect medium (33%+15% sugar). Subsequently, the plates are sealed with parafilm, which a mixed population of green peach aphids (*Myzus persicae*) within a second microtitre plate is able to puncture and imbibe the solution through.

After 5 days, the efficacy in % is determined. 100% means that all the aphids have been killed; 0% means that no aphids have been killed.

In this test, for example, the following compounds from the preparation examples show an efficacy of 100% at an application rate of 4 ppm: I-01, I-03, I-04, I-05, I-06, I-07, I-08, I-09, I-10, I-11, I-13, I-15, I-16

In this test, for example, the following compounds from the preparation examples show an efficacy of 90% at an application rate of 4 ppm: I-02, I-12

*Myzus persicae* Spray Test

Solvent: 78 parts by weight of acetone 1.5 parts by weight of dimethylformamide

Emulsifier: alkylaryl polyglycol ether

To produce a suitable active compound preparation, 1 part by weight of active compound is dissolved using the stated parts by weight of solvent and made up with water containing an emulsifier concentration of 1000 ppm until the desired concentration is attained. To produce further test concentrations, the formulation is diluted with emulsifier-containing water.

Discs of Chinese cabbage leaves (*Brassica pekinensis*) infested by all stages of the green peach aphid (*Myzus persicae*) are sprayed with an active compound formulation of the desired concentration.

After 5 days, the efficacy in % is determined. 100% means that all the aphids have been killed; 0% means that no aphids have been killed.

In this test, for example, the following compounds from the preparation examples show an efficacy of 100% at an application rate of 100 g/ha: I-02, I-08, I-13, I-16

In this test, for example, the following compounds from the preparation examples show an efficacy of 90% at an application rate of 100 g/ha: I-03, I-05, I-10, I-15

*Phaedon cochleariae*—Spray Test

Solvent: 78.0 parts by weight of acetone 1.5 parts by weight of dimethylformamide Emulsifier: alkylaryl polyglycol ether To produce a suitable active compound preparation, 1 part by weight of active compound is dissolved using the stated parts by weight of solvent and made up with water containing an emulsifier concentration of 1000 ppm until the desired concentration is attained. To produce further test concentrations, the formulation is diluted with emulsifier-containing water.

Discs of Chinese cabbage leaves (*Brassica pekinensis*) are sprayed with an active compound formulation of the desired concentration and, after drying, populated with larvae of the mustard beetle (*Phaedon cochleariae*).

After 7 days, the efficacy in % is determined. 100% means that all the beetle larvae have been killed; 0% means that no beetle larvae have been killed.

In this test, for example, the following compounds from the preparation examples show an efficacy of 100% at an application rate of 100 g/ha: I-01, I-02, I-03, I-05, I-06, I-12, I-13

In this test, for example, the following compounds from the preparation examples show an efficacy of 83% at an application rate of 100 g/ha: I-08

In this test, for example, the following compounds from the preparation examples show an efficacy of 100% at an application rate of 20 g/ha: I-01, I-05, I-06, I-12

In this test, for example, the following compounds from the preparation examples show an efficacy of 83% at an application rate of 20 g/ha: I-10, I-13

*Spodoptera frugiperda*—Spray Test
Solvent: 78.0 parts by weight of acetone
1.5 parts by weight of dimethylformamide
Emulsifier: alkylaryl polyglycol ether To produce a suitable active compound preparation, 1 part by weight of active compound is dissolved using the stated parts by weight of solvent and made up with water containing an emulsifier concentration of 1000 ppm until the desired concentration is attained. To produce further test concentrations, the formulation is diluted with emulsifier-containing water.

Leaf discs of maize (*Zea mays*) are sprayed with an active compound formulation of the desired concentration and, after drying, populated with caterpillars of the fall armyworm (*Spodoptera frugiperda*).

After 7 days, the efficacy in % is determined. 100% means that all the caterpillars have been killed; 0% means that no caterpillar has been killed.

In this test, for example, the following compounds from the preparation examples show an efficacy of 100% at an application rate of 100 g/ha: I-01, I-05, I-12

In this test, for example, the following compounds from the preparation examples show an efficacy of 83% at an application rate of 100 g/ha: I-10

DEPOSITION EXAMPLES

*Aphis gossypii* Spray Test (APHIGO)
Solvent: 14 parts by weight of dimethylformamide
Emulsifier: alkylaryl polyglycol ether To produce a suitable active compound preparation, 1 part by weight of active compound is dissolved using the stated parts by weight of solvent and made up with water containing an emulsifier concentration of 1000 ppm until the desired concentration is attained. To produce further test concentrations, the formulation is diluted with emulsifier-containing water. If the addition of ammonium salts or/and penetrants is required, these are each added in a concentration of 1000 ppm to the formulation solution.

Cotton plants (*Gossypium hirsutum*) heavily infested by the cotton aphid (*Aphis gossypii*) are sprayed with an active compound formulation of the desired concentration.

After the desired time, the kill in % is determined. 100% means that all the aphids have been killed; 0% means that no aphids have been killed.

In this test, for example, the following compounds from the preparation examples show superior efficacy to the prior art: see table.

*Myzus persicae*—Spray Test (MYZUPE S)
Solvent: 14 parts by weight of dimethylformamide
Emulsifier: alkylaryl polyglycol ether To produce a suitable active compound preparation, 1 part by weight of active compound is dissolved using the stated parts by weight of solvent and made up with water containing an emulsifier concentration of 1000 ppm until the desired concentration is attained. To produce further test concentrations, the formulation is diluted with emulsifier-containing water. If the addition of ammonium salts or/and penetrants is required, these are each added in a concentration of 1000 ppm to the formulation solution.

Bell pepper plants (*Capsicum annuum*) severely infested with the green peach aphid (*Myzus persicae*) are treated by spraying with the active compound formulation in the desired concentration.

After the desired time, the kill in % is determined. 100% means that all the animals have been killed; 0% means that no animals have been killed.

In this test, for example, the following compounds from the preparation examples show superior efficacy to the prior art: see table.

*Myzus persicae*—Drench Test (MYZUPE D)
Solvent: 7 parts by weight of dimethylformamide
Emulsifier: 2 parts by weight of alkylaryl polyglycol ether To produce a suitable active compound preparation, 1 part by weight of active compound is mixed with the specified amounts of solvent and emulsifier, and the concentrate is diluted with water to the desired concentration, it being necessary to include the volume of soil which is drenched in the calculation. It should be ensured that a concentration of 40 ppm of emulsifier in the soil is not exceeded. To produce further test concentrations, water is used for dilution.

Savoy cabbage (*Brassica oleracea*) in pots with soil and infested by all stages of the green peach aphid (*Myzus persicae*) is watered with an active compound preparation of the desired concentration.

After the desired period of time, the efficacy in % is determined. 100% means that all the aphids have been killed; 0% means that no aphids have been killed.

In this test, for example, the following compounds from the preparation examples show superior efficacy to the prior art: see table.

*Nilaparvata lugens*—Spray Test (NILALU)
Solvent: 52.5 parts by weight of acetone
7 parts by weight of dimethylformamide
Emulsifier: alkylaryl polyglycol ether To produce a suitable active compound preparation, 1 part by weight of active compound is dissolved using the stated parts by weight of solvent and made up with water containing an emulsifier concentration of 1000 ppm until the desired concentration is attained. To produce further test concentrations, the formulation is diluted with emulsifier-containing water. If the addition of ammonium salts or/and penetrants is required, these are each added in a concentration of 1000 ppm to the formulation solution.

Rice plants (*Oryza sativa*) are sprayed with an active ingredient formulation of the desired concentration and then populated with larvae of the brown planthopper (*Nilaparvata lugens*).

After the desired period of time, the efficacy in % is determined. 100% means that all of the planthoppers have been killed; 0% means that none of the planthoppers have been killed.

In this test, for example, the following compounds from the preparation examples show superior efficacy to the prior art: see table.

| Substance | Structure | Object | Concentration | % efficacy | dat |
|---|---|---|---|---|---|
| Example No. I-34 known from WO2016/162318 | 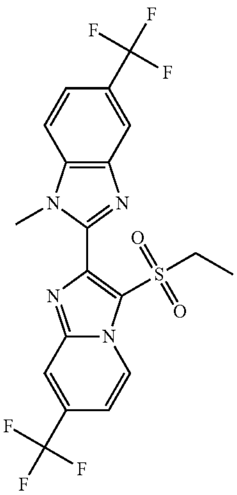 [SMILES: CCS(=O)(=O)c1c(-c2nc3cc(C(F)(F)F)ccc3n2C)nc2cc(C(F)(F)F)ccn12] | MYZUPE S | 20 ppm | 0 | 6 dat |
| | | MYZUPE D | 20 ppm | 0 | 10 dat |
| | | APHIGO | 20 ppm | 0 | 6 dat |
| | | NILALU | 500 g/ha | 0 | 4 dat |
| | | | 100 g/ha | 0 | 4 dat |
| Example No. I-01 according to the invention | 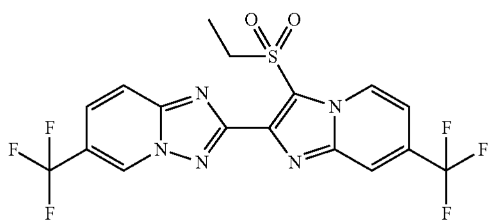 [SMILES: CCS(=O)(=O)c1c(-c2nc3ccc(C(F)(F)F)cn3n2)nc2cc(C(F)(F)F)ccn12] | MYZUPE S | 20 ppm | 95 | 6 dat |
| | | MYZUPE D | 20 ppm | 90 | 10 dat |
| | | APHIGO | 20 ppm | 99 | 6 dat |
| | | NILALU | 500 g/ha | 80 | 4 dat |
| Example No. I-06 according to the invention | 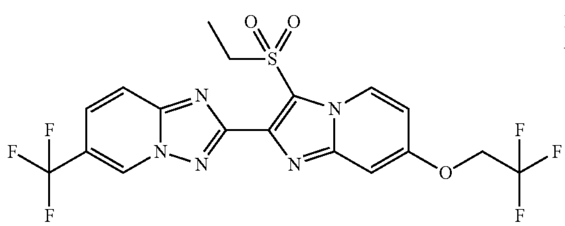 | MYZUPE S | 20 ppm | 99 | 6 dat |
| | | APHIGO | 20 ppm | 95 | 6 dat |
| Example No. I-10 according to the invention | 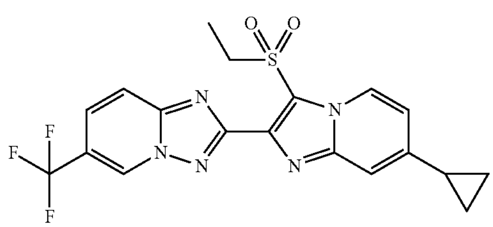 [SMILES: CCS(=O)(=O)c1c(-c2nc3ccc(C(F)(F)F)cn3n2)nc2cc(C3CC3)ccn12] | MYZUPE S | 20 ppm | 100 | 6 dat |
| | | MYZUPE D | 20 ppm | 90 | 10 dat |
| | | APHIGO | 20 ppm | 99 | 6 dat |
| | | NILALU | 100 g/ha | 100 | 4 dat |
| Example No. I-13 according to the invention | 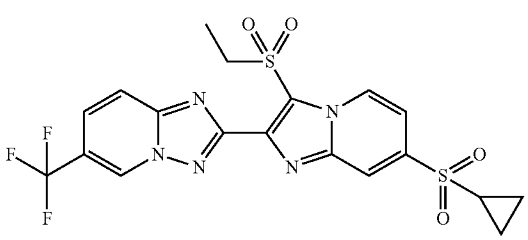 [SMILES: CCS(=O)(=O)c1c(-c2nc3ccc(C(F)(F)F)cn3n2)nc2cc(S(=O)(=O)C3CC3)ccn12] | MYZUPE S | 20 ppm | 95 | 6 dat |
| | | MYZUPE D | 20 ppm | 100 | 10 dat |
| | | APHIGO | 20 ppm | 99 | 6 dat |
| | | NILALU | 100 g/ha | 100 | 4 dat |

The invention claimed is:

1. A compound of formula (I)

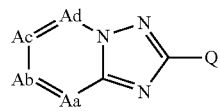

(I)

in which

Aa represents nitrogen or $C(R^1)$,

Ab represents nitrogen or $C(R^2)$,

Ac represents nitrogen or $C(R^3)$,

Ad represents nitrogen or $C(R^4)$, where at most one of the groups Aa, Ab, Ac and Ad represents nitrogen, $R^1$, $R^2$, $R^3$, $R^4$ each independently of one another represent hydrogen, halogen, cyano, $SF_5$, $(C_1-C_4)$-alkyl, $(C_1-C_4)$-haloalkyl, $(C_1-C_4)$-haloalkoxy, $(C_3-C_6)$-cycloalkyl, $(C_1-C_4)$-cyanoalkyl, cyano-$(C_3-C_6)$-cycloalkyl, $(C_1-C_4)$-alkylthio, $(C_1-C_4)$-haloalkylthio, $(C_1-C_4)$-alkylsulfinyl, $(C_1-C_4)$-haloalkylsulfinyl, $(C_1-C_4)$-alkyl sulfonyl or $(C_1-C_4)$-haloalkylsulfonyl, where at most two of the radicals $R^1$, $R^2$, $R^3$ and $R^4$ represent a radical other than hydrogen, Q represents a heteroaromatic 8-, 9- or 10-membered fused bicyclic ring system selected from the group consisting of Q1, Q4, Q5, Q7, Q8 and Q9,

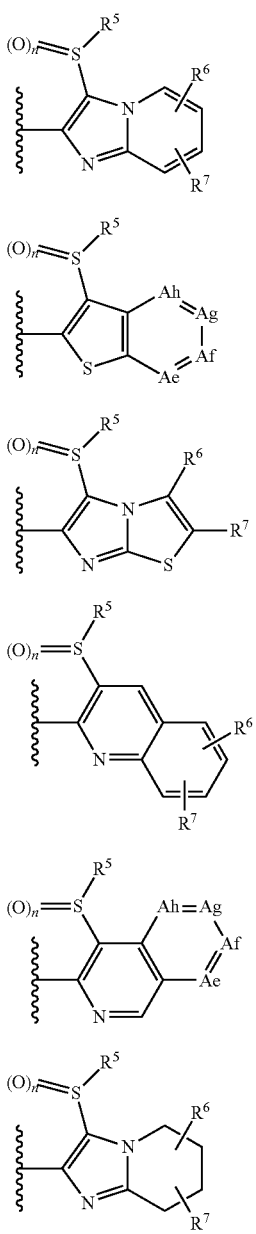

Ae represents nitrogen, $C(R^6)$ or $C(R^7)$,
Af represents nitrogen, $C(R^6)$ or $C(R^7)$,
Ag represents nitrogen, $C(R^6)$ or $C(R^7)$,
Ah represents nitrogen, $C(R^6)$ or $C(R^7)$, where at most one of the groups Ae, Af, Ag and Ah represents nitrogen, $R^5$ represents $(C_1-C_4)$-alkyl, $(C_1-C_4)$-haloalkyl or $(C_3-C_6)$-cycloalkyl, $R^6$ represents hydrogen, $R^7$ represents hydrogen, halogen, cyano, $SF_5$, $(C_1-C_4)$-alkyl, $(C_1-C_4)$-haloalkyl, $(C_1-C_4)$-haloalkoxy, $(C_1-C_4)$-alkoxy, $(C_3-C_6)$-cycloalkyl, $(C_3-C_6)$-halocycloalkyl, $(C_3-C_6)$-cycloalkyl-$(C_1-C_4)$-alkyl, $(C_3-C_6)$-cycloalkyl-$(C_1-C_4)$-haloalkyl, $(C_1-C_4)$-alkyl-$(C_3-C_6)$-cycloalkyl, $(C_1-C_4)$-haloalkyl-$(C_3-C_6)$-cycloalkyl, $(C_1-C_4)$-cyanoalkyl, cyano-$(C_3-C_6)$-cycloalkyl or $R^7$ represents a group selected from —C(=O)—$R^{21}$, —C(=S)—$R^{21}$, —C(=O)—$OR^{21}$, —C(=O)—$NR^{20}R^{21}$, —C(=S)—$NR^{20}R^{21}$, —CH(=N—$OR^{23}$), —CH(=N—$NR^{23}R^{24}$), —$OR^{21}$, —OC(=O)—$NR^{20}R^{21}$, —$NR^{20}R^{21}$, —N($R^{20}$)—$NR^{21}R^{22}$, —N($R^{20}$)—C(=O)—$R^{21}$, —N($R^{20}$)—C(=S)—$R^{21}$, —N($R^{20}$)—C(=O)—$OR^{21}$, —N($R^{20}$)—C(=S)—$OR^{21}$, —N($R^{20}$)—C(=O)—$NR^{21}R^{22}$, —N($R^{20}$)—C(=S)—$NR^{21}R^{22}$ or —S(=O)$_m R^{21}$, where $R^{20}$, $R^{21}$, $R^{22}$ each independently of one another represent hydrogen or represent $(C_1-C_4)$-alkyl, $(C_1-C_4)$-haloalkyl, $(C_1-C_4)$-alkoxy, $(C_1-C_4)$-haloalkoxy, $(C_2-C_6)$-alkenyl, $(C_2-C_6)$-alkynyl, $(C_3-C_6)$-halocycloalkyl or $(C_3-C_6)$-cycloalkyl, each of which is optionally mono- or polysubstituted by identical or different substituents, where the substituents independently of one another may be selected from halogen, cyano, $(C_1-C_4)$-alkyl, $(C_1-C_4)$-haloalkyl, $(C_3-C_6)$-cycloalkyl, $(C_1-C_4)$-alkoxy or $(C_1-C_4)$-haloalkoxy, $R^{23}$, $R^{24}$ each independently of one another represent hydrogen, $(C_1-C_4)$-alkyl, $(C_2-C_6)$-alkenyl, $(C_2-C_6)$-alkynyl, $(C_3-C_6)$-cycloalkyl, $(C_3-C_6)$-halocycloalkyl, $(C_1-C_4)$-haloalkyl, $(C_2-C_6)$-haloalkenyl or $(C_2-C_6)$-haloalkynyl and m represents 0, 1 or 2 and n represents 0, 1 or 2.

2. The compound of formula (I) according to claim 1, wherein

Aa represents nitrogen or $C(R^1)$,
Ab represents nitrogen or $C(R^2)$,
Ac represents nitrogen or $C(R^3)$,
Ad represents nitrogen or $C(R^4)$, where at most one of the groups Aa, Ab, Ac and Ad represents nitrogen, $R^1$, $R^2$, $R^3$, $R^4$ independently of one another represent hydrogen, halogen, cyano, $(C_1-C_4)$-alkyl, $(C_1-C_4)$-haloalkyl, $(C_1-C_4)$-haloalkoxy, $(C_3-C_6)$-cycloalkyl, $(C_1-C_4)$-cyanoalkyl, cyano-$(C_3-C_6)$-cycloalkyl, $(C_1-C_4)$-haloalkylthio, $(C_1-C_4)$-haloalkylsulfinyl or $(C_1-C_4)$-haloalkylsulfonyl, where at most one of the radicals $R^1$, $R^2$, $R^3$ and $R^4$ represents a radical other than hydrogen, Q represents a heteroaromatic 8-, 9- or 10-membered fused bicyclic ring system from the group consisting of Q1, Q4, Q5, Q7, Q8 and Q9,

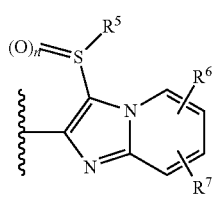

-continued

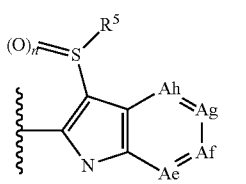
Q4

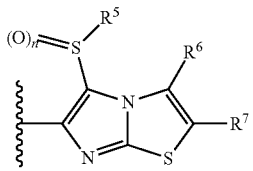
Q5

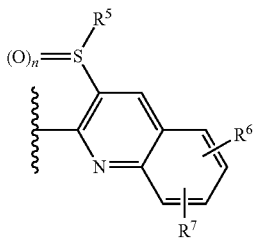
Q7

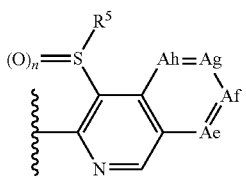
Q8

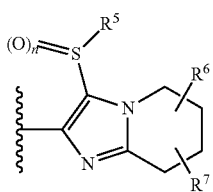
Q9

Ae represents nitrogen, C(R$^6$) or C(R$^7$),
Af represents nitrogen, C(R$^6$) or C(R$^7$),
Ag represents nitrogen, C(R$^6$) or C(R$^7$),
Ah represents nitrogen, C(R$^6$) or C(R$^7$),
where at most one of the groups Ae, Af, Ag and Ah represents nitrogen,
R$^5$ represents (C$_1$-C$_4$)-alkyl or (C$_3$-C$_4$)-cycloalkyl,
R$^6$ represents hydrogen,
R$^7$ optionally represents hydrogen, halogen, cyano, SF$_5$, (C$_1$-C$_4$)-alkyl, (C$_1$-C$_4$)-haloalkyl, (C$_1$-C$_4$)-haloalkoxy, (C$_1$-C$_4$)-alkoxy, (C$_3$-C$_6$)-cycloalkyl, (C$_3$-C$_6$)-halocycloalkyl, (C$_3$-C$_6$)-cycloalkyl-(C$_1$-C$_4$)-alkyl, (C$_3$-C$_6$)-cycloalkyl-(C$_1$-C$_4$)-haloalkyl, (C$_1$-C$_4$)-alkyl-(C$_3$-C$_6$)-cycloalkyl, (C$_1$-C$_4$)-haloalkyl-(C$_3$-C$_6$)-cycloalkyl, (C$_1$-C$_4$)-cyanoalkyl, cyano-(C$_3$-C$_6$)-cycloalkyl or
R$^7$ represents a group selected from —C(=O)—R$^{21}$, —C(=S)—R$^{21}$, —C(=O)—OR$^{21}$, —C(=O)—NR$^{20}$R$^{21}$, —OR$^{21}$, —NR$^{20}$R$^{21}$, —N(R$^{20}$)—C(=O)—R$^{21}$, —S(=O)$_m$—R$^{21}$ or —N(R$^{20}$)—C(=S)—R$^{21}$,
where
R$^{20}$, R$^{21}$, R$^{22}$ each independently of one another represent hydrogen or represent (C$_1$-C$_4$)-alkyl, (C$_1$-C$_4$)-haloalkyl, (C$_1$-C$_4$)-alkoxy, (C$_1$-C$_4$)-haloalkoxy, (C$_2$-C$_6$)-alkenyl, (C$_2$-C$_6$)-alkynyl, (C$_3$-C$_6$)-halocycloalkyl or (C$_3$-C$_6$)-cycloalkyl, each of which is optionally mono- or polysubstituted by identical or different substituents, where the substituents independently of one another may be selected from halogen, cyano, (C$_1$-C$_4$)-alkyl, (C$_1$-C$_4$)-haloalkyl, (C$_3$-C$_6$)-cycloalkyl, (C$_1$-C$_4$)-alkoxy or (C$_1$-C$_4$)-haloalkoxy, and
m represents 2 and
n optionally represents 0, 1 or 2.

3. The compound of formula (I) according to claim 1, wherein
Aa represents nitrogen or CH,
Ab represents nitrogen or C(R$^2$),
Ac represents nitrogen or C(R$^3$),
Ad represents CH,
where at most one of the groups Aa, Ab and Ac represents nitrogen,
R$^2$, R$^3$ independently of one another represent hydrogen or (C$_1$-C$_6$)-haloalkyl,
Q represents a heteroaromatic 8-, 9- or 10-membered fused bicyclic ring system from the group consisting of Q1, Q7, Q8 or Q9,

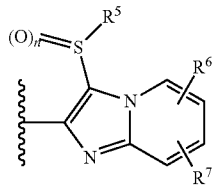
Q1

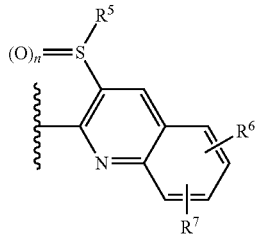
Q7

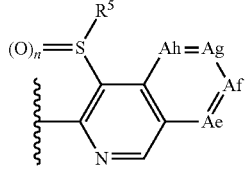
Q8

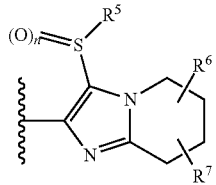
Q9 where
Ae represents CH,
Af represents CH,
Ag represents CH,
Ah represents CH,
R$^5$ represents (C$_1$-C$_4$)-alkyl,
R$^6$ represents hydrogen,
R$^7$ represents hydrogen, halogen, (C$_1$-C$_4$)-alkyl, (C$_1$-C$_4$)-haloalkyl, (C$_3$-C$_6$)-cycloalkyl or —N(R$^{20}$)—C(=O)—R$^{21}$, —C(=O)OR$^{21}$, —S(=O)$_m$—R$^{21}$ or (C$_1$-C$_4$)-haloalkoxy,
where R$^{20}$ represents hydrogen,
R$^{21}$ represents (C$_3$-C$_6$)-cycloalkyl, (C$_1$-C$_4$)-alkyl or (C$_1$-C$_4$)-alkoxy,
m represents 2 and
n represents 2.

4. The compound of formula (I) according to claim 3, wherein $R^7$ in the case that Q=Q1, represents 3-halogen, 3-$(C_1-C_4)$-haloalkyl, 3-$(C_3-C_6)$-cycloalkyl, 3-$(C_1-C_4)$-haloalkoxy, 3-$S(=O)_m$—$R^{21}$, —$C(=O)$—$OR^{21}$ or 3-N($R^{20}$)—$C(=O)$—$R^{21}$,
where $R^{20}$ represents hydrogen,
$R^{21}$ represents $(C_3-C_6)$-cycloalkyl, $(C_1-C_4)$-alkoxy or $(C_1-C_4)$-alkyl
and m represents 2,
or in the case that Q=Q7, Q8 or Q9, represents hydrogen.

5. The compound of formula (I) according to claim 1, wherein
Aa represents nitrogen or CH,
Ab represents nitrogen or $C(R^2)$,
Ac represents nitrogen or $C(R^3)$,
Ad represents CH,
where at most one of the groups Aa, Ab and Ac represents nitrogen,
$R^2$ represents hydrogen or trifluoromethyl,
$R^3$ represents hydrogen or trifluoromethyl,
Q represents a heteroaromatic fused bicyclic ring system from the group consisting of Q1, Q7, Q8 or Q9,

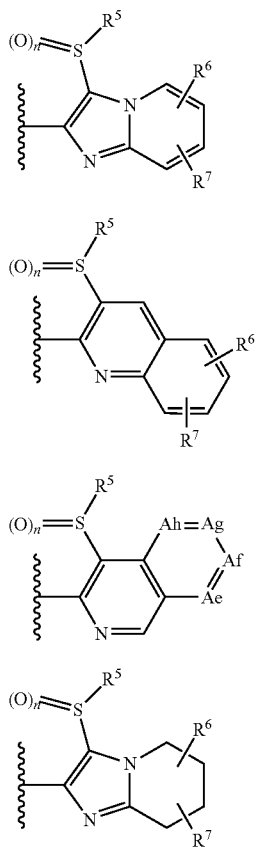

where
Ae represents CH,
Af represents CH,
Ag represents CH,
Ah represents CH,
$R^5$ represents ethyl,
$R^6$ represents hydrogen,
$R^7$ represents hydrogen, iodine, cyclopropyl, —$SO_2$-cyclopropyl, —$OCH_2CF_3$, —NHCOMe, —NHCOOMe, —COOMe, trifluoromethyl or —NHCO-cyclopropyl
and
n represents 2.

6. The compound of formula (I) according to claim 5, wherein $R^7$
in the case that Q=Q1, represents 3-iodine, 3-cyclopropyl, 3-$SO_2$-cyclopropyl, 3-trifluoromethyl, 3-$OCH_2CF_3$, 3-NHCOMe, 3-NHCOOMe, 3-COOMe or 3-NHCO—cyclopropyl, or
in the case that Q=Q7, Q8 or Q9, represents hydrogen.

7. The compound of the formula (I) according to claim 1, wherein
$R^2$, $R^3$ independently of one another represent hydrogen, $(C_1-C_4)$-haloalkylthio, $(C_1-C_4)$-haloalkylsulfinyl, $(C_1-C_4)$-haloalkylsulfonyl or $(C_1-C_4)$-haloalkyl, where only one of the radicals $R^2$ or $R^3$ does not represent hydrogen.

8. The compound of formula (I) according to claim 1, wherein
Aa represents nitrogen or $C(R^1)$,
Ab represents nitrogen or $C(R^2)$,
Ac represents nitrogen or $C(R^3)$ and
Ad represents CH,
where at most one of the radicals Aa, Ab or Ac represents nitrogen and at least one of the radicals $R^2$ or $R^3$ does not represent hydrogen and le does not represent hydrogen only in the case where $R^3$ likewise does not represent hydrogen.

9. The compound of formula (I) according to claim 1, where for Q=Q1 and Q4
at least one of the radicals $R^6$ or $R^7$ does not represent hydrogen, halogen, $(C_3-C_6)$-cycloalkyl, cyano-, —C(O)OH— or —C(O)NH$_2$-substituted $(C_3-C_6)$-cycloalkyl, $(C_1-C_6)$-alkyl, $(C_1-C_6)$-haloalkyl, $(C_1-C_6)$-alkoxy, $(C_1-C_6)$-haloalkoxy, $(C_1-C_6)$-alkylthio, halo-$(C_1-C_6)$-alkylthio, $(C_1-C_6)$-alkyl sulfinyl, halo-$(C_1-C_6)$-alkyl sulfinyl, $(C_1-C_6)$-alkyl sulfonyl, halo-$(C_1-C_6)$-alkylsulfonyl, —$NH_2$, —$NHR^x$, cyano or nitro,
where $R^x$ represents $(C_1-C_6)$-alkyl, $(C_1-C_6)$-haloalkyl, $(C_1-C_6)$-alkylcarbonyl, halo-$(C_1-C_6)$-alkylcarbonyl, $(C_1-C_6)$-alkoxycarbonyl, halo-$(C_1-C_6)$-alkoxycarbonyl, $(C_1-C_6)$-alkylsulfonyl or halo-$(C_1-C_6)$-alkylsulfonyl
and
where for Q=Q5
$R^7$ does not represent hydrogen, halogen, $(C_1-C_6)$-alkyl or $(C_1-C_6)$-haloalkyl.

10. The compound of formula (I) according to claim 1, where if
Aa represents CH,
Ab represents $C(R^2)$,
Ac represents CH and
Ad represents CH
or
Aa represents CH,
Ab represents $C(R^2)$,
Ac represents N and
Ad represents CH
or
Aa represents CH,
Ab represents $C(R^2)$,
Ac represents CH and
Ad represents N,
where $R^2$ represents —$CF_3$, —$SOCF_3$, —$SCF_3$, —$SO_2CF_3$
and for Q=Q1
$R^6$ is located at position 2 or 4 and represents H, F, Cl, Br, I, Me, —$CF_3$, —SMe, —SOMe, —$SO_2$Me, —OMe, —$OCF_3$, —$NO_2$, $NH_2$, CN, —$SOCF_3$, —$SCF_3$ or —$SO_2CF_3$ and R⁷ is located at position 3,
then for Q=Q1 R⁷ does not represent H, F, Cl, Br, I, Me, —CF₃, —SMe, —SOMe, —SO₂Me, —OMe, —OCF₃, —NO₂, NH₂, CN, —SOCF₃, —SCF₃, —SO₂CF₃ or cyclopropyl
or
if
Aa represents CH,
Ab represents C(R²),
Ac represents CH and
Ad represents CH
or
Aa represents CH,
Ab represents C(R²),
Ac represents N and
Ad represents CH
or
Aa represents CH,
Ab represents C(R²),
Ac represents CH and
Ad represents N,
where R² represents —CF₃,
and for Q=Q4
Ae or Ag represents C(R⁶) and R⁶ represents H, F, Cl, Br, I, Me, —CF₃, —SMe, —SOMe, —SO₂Me, —OMe, —OCF₃, —NO₂, NH₂, CN, —SOCF₃, —SCF₃ or —SO₂CF₃
and Af represents C(R⁷),
then for Q=Q4 R⁷ does not represent H, F, Cl, Br, I, Me, —CF₃, —SMe, —SOMe, —SO₂Me, —OMe, —OCF₃, —NO₂, NH₂, CN, —SOCF₃, —SCF₃, —SO₂CF₃ or cyclopropyl
or
if
Aa represents CH,
Ab represents C(R²),
Ac represents CH and
Ad represents CH
or
Aa represents CH,
Ab represents C(R²),
Ac represents N and
Ad represents CH
or
Aa represents CH,
Ab represents C(R²),
Ac represents CH and
Ad represents N,
where R² represents —CF₃,
and for Q=Q5
R⁶ represents H,
then for Q=Q5 R⁷ does not represent H, F, Cl, Br, I, Me or —CF₃.

11. An agrochemical formulation comprising a compound of formula (I) according to claim 1 and one or more extenders and/or surfactants.

12. The agrochemical formulation according to claim 11, additionally comprising a further active compound.

13. A method of controlling one or more animal pests, comprising applying a compound of formula (I) according to claim 1 or an agrochemical formulation comprising a compound of formula I to animal pests and/or a habitat thereof.

14. A product comprising a compound of formula (I) according to claim 1 or agrochemical formulation comprising a compound of formula I for controlling one or more animal pests.

15. A method for protecting seed and/or a germinating plant from one or more pests comprising contacting seed with a compound of formula (I) according to claim 1 or with a formulation comprising a compound of formula I.

* * * * *